(12) United States Patent
Balkovec et al.

(10) Patent No.: US 6,630,510 B1
(45) Date of Patent: Oct. 7, 2003

(54) SUBSTITUTED SUCCINIC ACID METALLO-β-LACTAMASE INHIBITORS AND THEIR USE IN TREATING BACTERIAL INFECTIONS

(75) Inventors: James M. Balkovec, Martinsville, NJ (US); Mark L. Greenlee, Rahway, NJ (US); Steven H. Olson, Metuchen, NJ (US); Gregory P. Rouen, New Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/697,415

(22) Filed: Oct. 26, 2000

Related U.S. Application Data
(60) Provisional application No. 60/162,370, filed on Oct. 28, 1999.

(51) Int. Cl.⁷ .................. C07C 55/10; A61K 31/194; A61P 31/04
(52) U.S. Cl. .................. 514/557; 560/76; 560/155; 560/171; 560/190; 546/235; 546/349; 548/300.1
(58) Field of Search .................. 560/76, 155, 171, 560/190; 544/349, 235; 548/300.1; 514/557

(56) References Cited

U.S. PATENT DOCUMENTS

| | | | |
|---|---|---|---|
| 4,770,799 A | | 9/1988 | Farng et al. |
| 5,414,108 A | * | 5/1995 | Toth et al. .................. 560/105 |
| 5,559,088 A | * | 9/1996 | Severns et al. .............. 560/190 |

FOREIGN PATENT DOCUMENTS

| | | |
|---|---|---|
| WO | WO 97/10225 | 3/1997 |
| WO | WO 97/19681 | 6/1997 |
| WO | WO 97/30027 | 8/1997 |
| WO | WO 98/17639 | 4/1998 |
| WO | WO 98/39311 | 9/1998 |
| WO | WO 98/40056 | 9/1998 |

OTHER PUBLICATIONS

Goto et al., Biol. Pharm. Bull., 20, 1136 (1997).
Payne et al., FEMS Microbiology Letters, 157, 171 (1997).
Payne et al., Antimicrob. Agents Chemother., 41, 135 (1997).
Page et al, Chem. Commun. 1609 (1998).
Page et al., Biochem. J., 331,703 (1998).
Toney et al., Chemistry and Biology, 5, 185 (1998).
Fastrez et al., Tetrahedron Lett., 36, 9313 (1995).
Schofield et al., Tetrahedron, 53, 7275 (1997).
Schofield et al., Bioorg & Med. Chem. Lett., 6, 2455 (1996).
Bush et al., Antimicrob. Agents Chemother, 41, 223 (1997).
D.M. Livermore, J. Antimicrob. Chemother., 1998, 41 (Suppl. D), 25.
K. Bush, Clin. Infect. Dis. 1998, 27 (Suppl 1), 548.
D.M. Livermore, J. Antimicrob. Chemother. 1997, 39, 673.
D.J. Payne, J. Med. Microbiol. 1993, 39, 93.
M.J. Crimmin et al., Syn Lett. 1993, 137.
Suzuki, Chem. Rev. 1995, 95, 2457.
J.L. Belletire and D. F. Fry, J. Org. Chem. 1987, 52, 2549.
N. Kise et al., J. Org. Chem. 1995, 60, 1100.

* cited by examiner

Primary Examiner—Richard L. Raymond
Assistant Examiner—Venkataraman Balasubramanian
(74) Attorney, Agent, or Firm—Sylvia A. Ayler; Mark R. Daniel; Valerie J. Camara

(57) ABSTRACT

This invention relates to novel substituted succinic acid metallo-β-lactamase inhibitors which are useful potentiators of β-lactam antibiotics. Accordingly, the present invention provides a method of treating bacterial infections in animals or humans which comprises administering, together with a b-lactam antibiotic, a therapeutically effective amount of a compound of formula I:

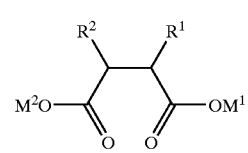

including pharmaceutically acceptable salts, prodrugs, anhydrides, and solvates thereof.

31 Claims, No Drawings

SUBSTITUTED SUCCINIC ACID METALLO-β-LACTAMASE INHIBITORS AND THEIR USE IN TREATING BACTERIAL INFECTIONS

This application claims benefit of U.S. Provisional Application No. 60/162,370 filed on Oct. 28, 1999.

BACKGROUND OF THE INVENTION

The present invention relates to compounds which have metallo-β-lactamase inhibitory characteristics. The invention also relates to methods of preparing, pharmaceutical compositions and uses of the compounds.

Metallo-β-lactamases are bacterial enzymes which confer resistance to virtually all clinically relevant β-lactam antibiotics, including carbapenems and jeopardize the future use of all such agents. The increased treatment of infections with carbapenems and other β-lactam antibiotics may lead to the proliferation of clinical bacterial strains which are able to produce metallo-β-lactamases and thus resist the effects of β-lactam antibiotics. In fact, metallo-β-lactamases have now been identified in a number of pathogenic bacterial species including *Bacillus cereus, Bacteroides fragilis, Aeromonas hydrophila, Klebsiella pneumoniae, Pseudomonas aeruginosa, Serratia marcescens, Stenotrophomonas maltophilia, Shigella flexneri, Legionella gormanii, Chryseobacterium meningosepticum, Chryseobacterium indologenes, Acinetobacter baumannii, Citrobacter freundii,* and *Aeromonas veronii*.

Accordingly, there is an increasing need for agents which when combined with a β-lactam antibiotic, e.g. imipenem, will restore the effectiveness of the β-lactam antibiotics and which are at the same time relatively free from undesirable side effects.

WO 98/17639, 97/30027, 98/40056, 98/39311 and 97/10225 teach certain beta-thiopropionyl-amino acid derivatives and their use as inhibitory agents against metallo-β-lactamases. Goto et. al., *Biol. Pharm. Bull.* 20, 1136 (1997), Payne et. al., *FEMS Microbiology Letters* 157, 171 (1997), Payne et al., *Antimicrob. Agents Chemother.* 41, 135 (1997), Page et. al., *Chem. Commun.* 1609 (1998) and Page et al., *Biochem. J.* 331, 703 (1998) also disclose certain thiols and thioesters as metallo-β-lactamase inhibitors. Additionally, Toney et al., *Chemistry and Biology* 5, 185 (1998), Fastrez et al., *Tetrahedron Lett.* 36, 9313 (1995), Schofield et al., *Tetrahedron* 53, 7275 (1997), Schofield et. al., *Bioorg. & Med. Chem. Lett.* 6, 2455 (1996) and WO 97/19681 disclose other metallo-β-lactamase inhibitors. However, the above noted references do not teach the compounds of the instant invention.

Other references which disclosed the general state of the art are Bush et al., *Antimicrob. Agents Chemother.* 41, 223 (1997); Livermore, D. M. *J. Antimicrob. Chemother.* 1998, 41 (Suppl. D), 25; Bush, K. *Clin. Infect. Dis.* 1998, 27 (Suppl 1), S48; Livermore, D. M. *J. Antimicrob. Chemother.* 1997, 39, 673 and Payne, D. J. *J. Med. Microbiol.* 1993, 39, 93.

SUMMARY OF THE INVENTION

This invention relates to novel substituted succinic acid metallo-β-lactamase inhibitors, which are useful potentiators of β-lactam antibiotics. Accordingly, the present invention provides a method of treating bacterial infections in animals or humans which comprises administering, together with a β-lactam antibiotic, a therapeutically effective amount of a compound of formula I:

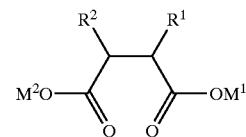

including pharmaceutically acceptable salts, prodrugs, anhydrides, and solvates thereof, wherein:

$M^1$ and $M^2$ are independently selected from:
(a) Hydrogen,
(b) Pharmaceutically acceptable cation,
(c) Pharmaceutically acceptable esterifying group; and
(d) A negative charge;

$R^1$ and $R^2$ are independently selected from the following:
(a) Hydrogen, provided that $R^1$ and $R^2$ are not hydrogen at the same time;
(b) a $C_1$ to $C_{16}$ straight, branched or unsaturated alkyl group substituted with 0 to 2 $R^q$ groups and substituted with 0 to 3 $R_x$ groups and optionally interrupted by one of the following O, S, $SO_2$, —C(O)—, —C(O)—$NR^a$—, —$CO_2$—;
(c) a group of the formula:

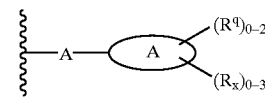

wherein
—A— represents a single bond, $C_1$ to $C_8$ straight, branched or unsaturated alkyl group optionally substituted with 1 to 2 $R_x$ groups and optionally interrupted by one of the following O, S, $SO_2$, —C(O)—, —C(O)—$NR^a$—, —$CO_2$—;

represents:
(1) a $C_6$ to $C_{14}$ aryl group;
(2) a $C_3$ to $C_{10}$ alicyclic group;
(3) a $C_3$ to $C_{14}$ heteroaryl group, which contains 1 to 3 heteroatoms, 0 to 3 of which heteroatoms are nitrogen and 0 to 1 of which are oxygen or sulfur;
(4) a $C_3$ to $C_{10}$ heterocyclic group, which contains 1 to 2 heteroatoms, 0 to 1 of which heteroatoms are nitrogen, and 0 to 2 of which are oxygen or sulfur; or (d) a group of the formula:

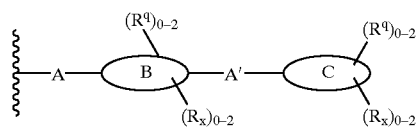

wherein:
—A— is as defined above;
A' is a single bond, O, S, or a $C_1$ to $C_6$ straight, branched or unsaturated alkyl group optionally substituted with 1–2 $R_x$ groups and optionally interrupted by one of the following groups O, S, SO$_2$, —C(O)—, —C(O)—NR$^a$—, —CO$_2$—;

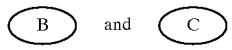

are independently selected from:
(1) a C$_6$ to C$_{10}$ aryl group;
(2) a C$_3$ to C$_8$ alicyclic group;
(3) a C$_2$ to C$_9$ heteroaryl group, which contains 1 to 3 heteroatoms, 0 to 3 of which heteroatoms are nitrogen and 0 to 1 of which are oxygen or sulfur;
(4) a C$_3$ to C$_8$ heterocyclic group, which contains 1 to 2 heteroatoms, 0 to 1 of which heteroatoms are nitrogen, and 0 to 2 of which are oxygen or sulfur;
provided that at least one R$^q$ group is present in R$^1$ or R$^2$ and that when more than one R$^q$ is present the total number of cationic nitrogen atoms does not exceed 8; the total number of cationic nitrogen atoms can be charged balanced by M$^1$ and/or M$^2$ or by M$^1$ and/or M$^2$ in combination with an appropriate number of Y$^-$; wherein:
R$^q$ is —E—Q$^+$Y$^-$;
Y$^-$ is a pharmaceutically acceptable anionic group;
E is —(CH$_2$)$_m$—X—(CH$_2$)$_n$—;
m is 0 to 6;
n is 0 to 6 (but when E is attached to an aromatic ring n is 1–6);
X is a bond, O, S, SO$_2$, —C(O)—, —C(O)—N(R$^a$)—, —C(O)O—, —CH=CH— or —C≡C—, provided that when X is O, S, —C(O)—N(R$^a$)— or —C(O)O—, then n is 2 to 6
and Q$^+$, attached to the (CH$_2$)$_n$ terminus of E is:
(1) a cationic group selected from the following:

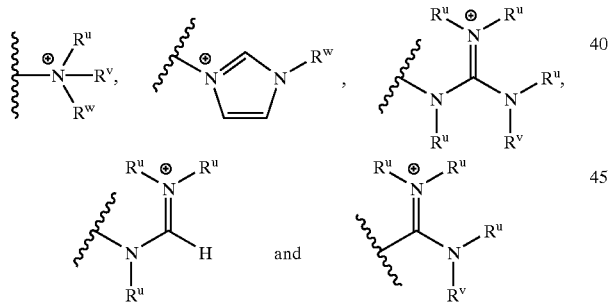

wherein:
R$^u$ and R$^v$ are independently hydrogen or C$_{1-6}$ alkyl optionally substituted with 1 to 2 R$^y$;
R$^w$ is hydrogen or C$_{1-6}$ alkyl optionally substituted with 1 to 2 R$_x$;
R$^u$ and R$^v$ when bonded to the same nitrogen atom may together be a C$_{3-6}$ alkyl radical, which when taken together with the intervening atoms form a ring;
Two R$^u$ groups on separate nitrogen atoms may together comprise a C$_{2-5}$ alkyl radical, which when taken together with the intervening atoms form a ring;
R$^u$, R$^v$ and R$^w$ when bonded to the same nitrogen atom may together form a C$_{6-10}$ tertiary alkyl radical, which with N$^+$ forms a bicyclic ring;

(2) A dicationic group:

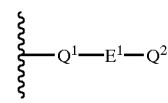

wherein:
E$^1$ is —(CH$_2$)$_p$—Z—(CH$_2$)$_r$—;
p and r are independently 1 to 4;
Z is a bond, O, S, SO$_2$, —C(O)—, —C(O)O—**, —CH=CH—, —C≡C—, or

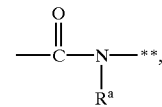

Provided that when Z is O or S, p is 2 to 4 and r is 2 to 4 and when Z is

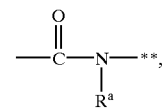

or —C(O)O—**, r is 2 to 4;
wherein ** denotes the atom which is bonded to the —(CH$_2$)$_r$— moiety of E$^1$ above;
Q$^1$ is selected from the following:

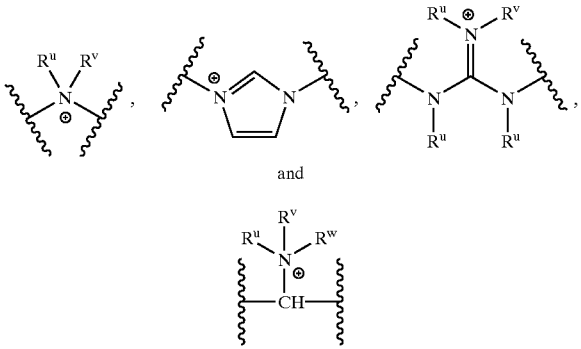

Q$^2$ is selected from the following:

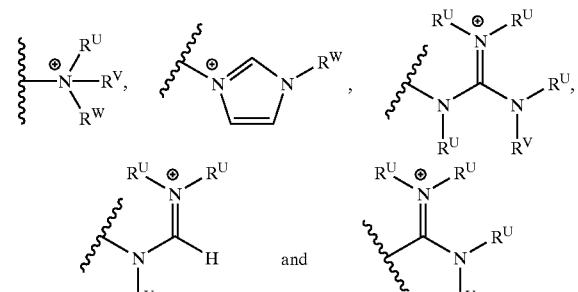

R$^u$, R$^v$ and R$^w$ are independently selected and defined as above,
And in addition, in the case where two R$^u$ groups on separate nitrogen atoms are joined to form a ring as defined above, two R$^v$ groups on the same two separate nitrogen atoms may also comprise a C$_{1-5}$ alkyl radical to form together with the intervening atoms a bicyclic ring; an example of such is:

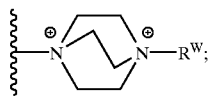

(3) A tricationic group selected from the following:

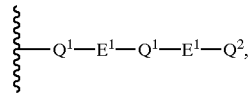 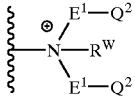

wherein:
Each $E^1$ is as defined above, but selected independently;
Each $Q^1$ is as defined above, but selected independently;
Each $Q^2$ is as defined above, but selected independently;
$R^u$, $R^v$ and $R^w$ are defined as in the definition of $Q^+$ item (2) above and selected independently; or (4) A tetracationic group selected from the following:

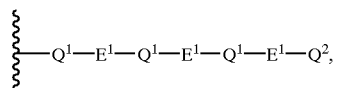 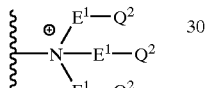

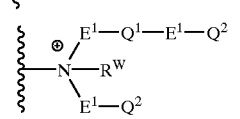 and 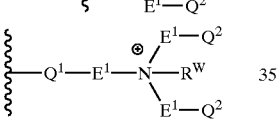

wherein:
Each $E^1$ is as defined above, but selected independently;
Each $Q^1$ is as defined above, but selected independently;
Each $Q^2$ is as defined above, but selected independently;
$R^u$, $R^v$ and $R^w$ are defined as in the definition of $Q^+$ item (2) above and selected independently;

where each $R_x$ is independently selected from the group consisting of:
(a) F, Cl, Br, I,
(b) $CF_3$,
(c) $OR^b$,
(d) CN,
(e) —C(O)—$R^c$,
(f) —S($O_2$)—$R^f$,
(g) —C(O)—$OR^a$,
(h) —O—C(O)—$R^c$,
(i) —S—$R^b$,
(j) —N($R^a$)—C(O)—$R^c$, (k) 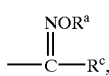

(l) 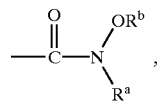

(m) 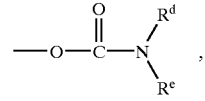

(n) 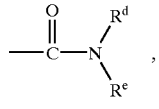

(o) 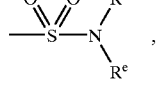

(p) 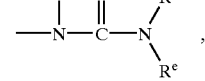

(q) —N($R^a$)—C(O)—$OR^f$,
(r) —S(O)—$R^f$,
(s) —N($R^a$)—S($O_2$)—$R^f$,
(t) $NO_2$, and
(u) $C_1$ to $C_8$ straight, branched or unsaturated alkyl optionally substituted with one of the substituents (a) through (t) above;
(v) —$CH_2$-aryl wherein the aryl is optionally substituted with one of the substituents (a) through (t) above;
or two adjacent $R_x$ groups on an aromatic ring may consist of the following divalent moiety, —O—$CH_2$—O—; wherein:
$R^a$ is H, $C_1$ to $C_6$ alkyl optionally substituted with $R^y$;
$R^b$ is H, $C_1$ to $C_6$ alkyl optionally substituted with $R^y$, $CH_2$-aryl, or aryl, said aryls optionally substituted with 1–2 $R^y$ groups;
$R^c$ is H, $C_1$ to $C_6$ alkyl optionally substituted with $R^y$, $CF_3$, or aryl, said aryl optionally substituted with 1–2 $R^y$ groups;
$R^d$ and $R^e$ are independently hydrogen, $C_1$ to $C_4$ alkyl optionally substituted with $R^y$, or $R^d$ and $R^e$ taken together may represent a 3 to 5-membered alkyl radical to form a ring, or $R^d$ and $R^e$ taken together may represent a 2 to 4-membered alkyl radical interrupted by O, S, SO or $SO_2$ to form a ring;
$R^f$ is $C_1$ to $C_6$ alkyl optionally substituted with $R^y$, or aryl, said aryl optionally substituted with 1–2 $R^y$ groups; and
$R^y$ is —OH, —$OCH_3$, $OCONH_2$, $OCOCH_3$, CHO, $COCH_3$, $CO_2CH_3$, $CONH_2$, CN, $SOCH_3$, $SO_2CH_3$, $SO_2NH_2$, F, Cl, Br, I or $CF_3$.

The invention is intended to include all of the isomeric forms of the compounds of formula I, including racemic, enantiomeric and diastereomeric forms.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 16 carbon atoms unless otherwise defined. It may be straight or branched. Preferred alkyl groups include methyl, ethyl, propyl, isopropyl, butyl and hexyl. When substituted, alkyl groups may be substituted with up to 3 substituent groups selected from $R_x$, as defined, and up to 2 substituent groups selected from $R^q$, as defined, at any available point of attachment. When the alkyl group is said to be substituted with an alkyl group, this is used interchangeably with "branched alkyl group". When the alkyl chain is interrupted by a group, e.g. O, this may occur between any two saturated carbons of the alkyl chain.

The term unsaturated alkyl refers to "alkenyl" or "alkynyl". The term "alkenyl" refers to an unsaturated alkyl such as a hydrocarbon radical, straight or branched containing from 2 to 16 carbon atoms and at least one carbon to carbon double bond. Preferred alkenyl groups include propenyl, hexenyl and butenyl. The term "alkynyl" refers to an unsaturated alkyl such as a hydrocarbon radical straight or branched, containing from 2 to 16 carbon atoms and at least one carbon to carbon triple bond. Preferred alkynyl groups include propynyl, hexynyl and butynyl.

The term "alicyclic" refers to non-aromatic monocyclic or bicyclic $C_3$–$C_{10}$ hydrocarbons, including unsaturated, which can be substituted with 0–3 groups of $R_x$. Examples of said groups include cycloalkyls such as cyclohexyl, cyclopentyl, bicyclo[2.2.1]heptyl, bicyclo[2.2.1]hepta-2,5-dienyl, bicyclo[2.2.2]octyl, bicyclo[2.2.2]octa-2,5-dienyl.

The term "alkylidene" refers to an alkyl group which is attached through two bonds on the same carbon atom of the alkyl group to a single attachment atom Examples of said groups include methylene, ethylidene, isopropylidene and the like.

Examples of when $R^d$ and $R^e$ are taken together along with the adjacent nitrogen atom to represent a 3 to 5 membered alkyl radical forming a ring or a 2 to 4 membered alkyl radical interrupted by O, S, SO, $SO_2$, to form a ring are pyrrolidinyl, piperidinyl, morpholinyl and the like.

The term "heterocyclic" refers to a monocyclic non-aromatic moiety containing 3–8 ring atoms or a bicyclic non-aromatic moiety containing 6–10 ring atoms, at least one of which ring atoms is a heteroatom selected from nitrogen, oxygen and sulfur and where one additional ring atom may be oxygen or sulfur. Examples of heterocyclic groups are furanyl, pyranyl, morpholinyl, dioxanyl and quinuclidinyl:

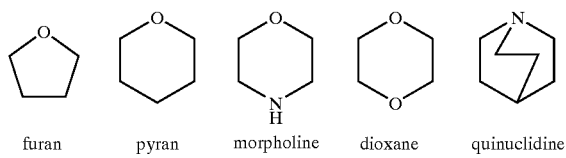

furan    pyran    morpholine    dioxane    quinuclidine

Aryl refers to aromatic rings e.g., phenyl, substituted phenyl and the like, as well as rings which are fused, e.g., naphthyl, phenanthrenyl fluorenonyl and the like. An aryl group thus contains at least one ring having at least 6 atoms, with up to three such rings being present, containing up to 14 atoms therein, with alternating (resonating) double bonds between adjacent carbon atoms. The preferred aryl groups are phenyl, naphthyl, and fluorenone. Aryl groups may likewise be substituted as defined. Preferred substituted aryls include phenyl, fluorenonyl and naphthyl.

The term "heteroaryl" (Het) refers to a monocyclic aromatic group having 5 or 6 ring atoms, a bicyclic aromatic group having 8 to 10 atoms, or tricyclic having 12–14 ring atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole, dibenzofuran, dibenzothiophene, carbazole, phenanthrene, anthracene, dibenzothiophene sulfone, fluorenone, quinoline and oxazine. Additional nitrogen atoms may be present together with the first nitrogen and oxygen or sulfur, giving, e.g., thiadiazole. Examples include the following:

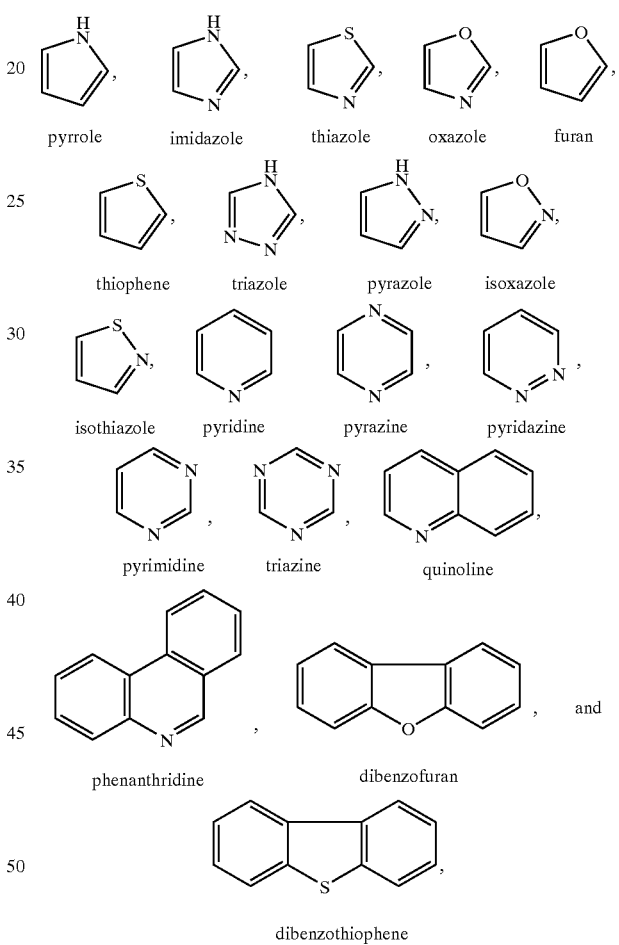

Heteroarylium refers to heteroaryl groups bearing a quaternary nitrogen atom and thus a positive charge. Non-limiting examples include the following:

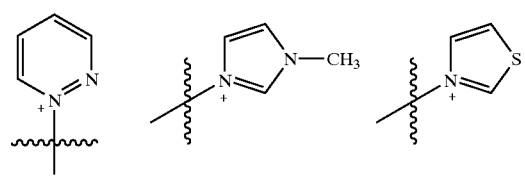

-continued

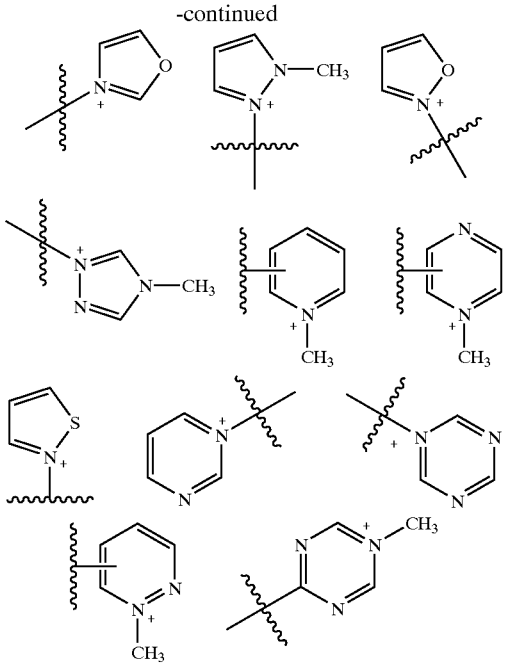

When a charge is shown on a particular nitrogen atom in a ring which contains one or more additional nitrogen atoms, it is understood that the charge may reside on a different nitrogen atom in the ring by virtue of charge resonance that occurs.

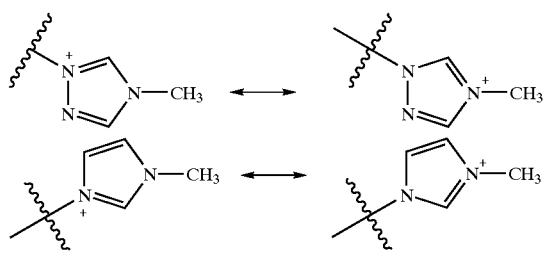

Similar charge resonance may occur in amidinium and guanidinium groups:

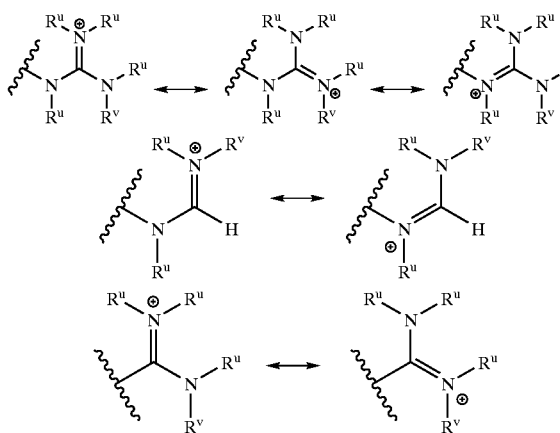

The term "heteroatom" means O, S or N, selected on an independent basis.

Halogen and "halo" refer to bromine, chlorine, fluorine and iodine.

The term "pro-drug" refers to compounds with a removable group attached to one or both of the carboxyl groups of compounds of formula I (e.g. biolabile esters). Groups which are useful in forming pro-drugs should be apparent to the medicinal chemist from the teachings herein. Examples include pivaloyloxymethyl, acetoxymethyl, phthalidyl, indanyl and methoxymethyl, and others described in detail in U.S. Pat. No. 4,479,947. These are also referred to as "biolabile esters".

The term "hydrate" is used in the conventional sense to include the compounds of formula I in physical association with water.

When a group is termed "substituted", unless otherwise indicated, this means that the group contains from 1 to 3 substituents thereon.

A bond terminated by a wavy line is used herein to signify the point of attachment of a substituent group. This usage is illustrated by the following example:

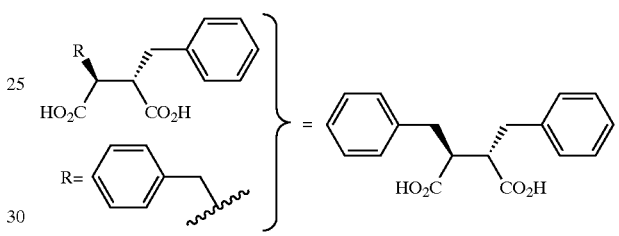

The terms "quaternary nitrogen" and "cationic nitrogen" refer to tetravalent, positively charged nitrogen atoms including, e.g., the positively charged nitrogen in a tetraalkylammonium group (e. g. $-N^+R''R^vR^w$), heteroarylium, (e.g., N-methyl-imidazolium), amidinium, guanidinium, basic nitrogens which are protonated at physiological pH, and the like. A "cationic group" is a moiety which contains at least one such quaternary nitrogen atom. Cationic groups thus encompass positively charged nitrogen-containing groups, as well as basic nitrogens which are protonated at physiologic pH. The terms dicationic, tricationic and tetracationic refer to groups which contain 2, 3 or 4 positively charged nitrogen atoms, respectively.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the compounds of the present invention suitable protecting groups represents hydroxyl-protecting, amine-protecting or carboxyl-protecting groups. Such conventional protecting groups consist of groups, which are used to protectively block the hydroxyl, amine or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable amine protecting groups include 9-fluorenylmethoxycarbonyl, p-nitrobenzyloxycarbonyl, benzyloxycarbonyl, allyloxycarbonyl, t-butyloxycarbonyl, 2,2,2-trichloroethyloxycarbonyl and the like.

Examples of suitable hydroxyl protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

With respect to $M^1$ and/or $M^2$, this represents a carboxylic hydrogen, a carboxylate anion (M represents a negative charge), a pharmaceutically acceptable ester (M represents an ester forming group) or a pharmaceutically acceptable cation. When $M^1$ and/or $M^2$ is a negative charge it can be used to provide the necessary charge balance in a compound with one or more positive charges. Likewise, when $M^1$ and/or $M^2$ is a negative charge it can be balanced by the appropriate number of counterions, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

For the purposes of this invention, all compounds have at least one Rq substituent containing at least one cationic nitrogen. Preferably 2 to 8 cationic nitrogens, more preferably 2 to 4 cationic nitrogens and most preferably 3 to 4 cationic nitrogens are present. The compounds are balanced with one or more, as necessary, of a charge balancing group $Y^-$. Alternatively, the compounds can be balanced using $M^1$ and/or $M^2$ as the charge balancing group with or without the use of $Y^-$. Examples of cases where a charge balancing group is required are quaternized substituents such as heteroarylium, $-N^+R''R^v-E^1-Q^1$, $-N^+R''R^vR^w$, and the like. Additionally, all compounds having one or more anions are counter balanced with one or more, as necessary, charge balancing cations.

The compounds of the present invention are useful per se and in their pharmaceutically acceptable salt and ester forms are potentiators for the treatment of bacterial infections in animal and human subjects. The term "pharmaceutically acceptable ester, salt or hydrate", refers to those salts, esters and hydrated forms of the compounds of the present invention which would be apparent to the pharmaceutical chemist. For example, those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers, Thus, the present invention is also concerned with pharmaceutical compositions and methods of treating bacterial infections utilizing as an active ingredient the novel carbapenemase compounds.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Acid addition salts of the compounds of formula I include compounds that contain a protonated, basic moiety in $R^q$. Compounds containing a basic moiety in $R^q$ are capable of protonation in aqueous media near pH 7, so that the basic moiety can exist as an equilibrium mixture of its neutral form and acid addition (protonated) form. The more basic the group, the greater the degree of protonation near pH 7. All such compounds are included in the present invention.

The pharmaceutically acceptable cations which can form a salt with one or both of the carboxyls ($CO_2M^1$ and $CO_2M^2$) of the compounds of formula I are known to those skilled in the art. Examples include those where $M^1$ and $M^2$ independently can be alkali metals such as sodium, potassium and the like, ammonium and the like.

The pharmaceutically acceptable esterifying groups are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intestinal mucosa, resistance to gastric acid degradation and other factors. Examples of biolabile esters include compounds in which $M^1$ and/or $M^2$ represents an alkoxyalkyl, alkylcarbonyloxyalkyl, alkoxycarbonyloxyalkyl, cycloalkoxylalkyl, alkenyloxyalkyl, aryloxyalkyl, alkoxyaryl, alkylthioalkyl, cycloalkylthioalkyl, alkenylthioalkyl, arylthioalkyl or alkylthioaryl group. The following $M^1$ and/or $M^2$ species are examples of biolabile ester forming moieties: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

$Y^-$ can be present or absent as necessary to maintain the appropriate charge balance. When present, these represent pharmaceutically acceptable counterions. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when more than one negative charge is necessary to maintain charge neutrality, the counterion indicator may represent a specie with more than one negative charge, such as malonate, tartrate or ethylenediaminetetraacetate (EDTA), or two or more monovalent anions, such as chloride, etc. When a multivalent negatively charged counterion is present with a compound of formula I which bears a net single positive charge, an appropriate number of molar equivalents of the anionic species can be found in association therewith to maintain the overall charge balance and neutrality.

Some of the compounds of formula I may be crystallized or recrystallized from solvents such as organic solvents. In such cases solvates may be formed. This invention includes within its cope stoichiometric solvates including hydrates as well as compounds containing variable amounts of solvents such as water that may be produced by processes such as lyophilization. The compounds of formula I may be prepared in crystalline form by for example dissolution of the compound in water, preferably in the minimum quantity thereof, followed by admixing of this aqueous solution with a water miscible organic solvent such as a lower aliphatic ketone such as a di-($C_{1-6}$) alkyl ketone, or a ($C_{1-6}$) alcohol, such as acetone or ethanol.

A subset of compounds of formula I which is of interest relates to those compounds where $M^1$ and $M^2$ are independently hydrogen or negative charge, said negative charge(s) balanced by the appropriate number of counter balancing ions, and all other variables are as described above.

Another subset of compounds of formula I which is of interest relates to those compounds where $R^1$ and/or $R^2$ represents a $C_1$ to $C_{16}$ straight, branched or unsaturated alkyl group substituted with 0 to 2 $R^q$, and substituted with 0 to 3 $R_x$ groups and optionally interrupted by one of the following O, S, $SO_2$, —C(O)—, —C(O)—$NR^a$— and —$CO_2$—, provided that at least one of $R^1$ or $R^2$ contains an $R^q$ and all other variables are described as above.

Another subset of compounds of formula I which is of interest relates to those compounds where $R^1$ and/or $R^2$ represents $C_{4-12}$ straight, branched or unsaturated alkyl group optionally substituted with 1–2 $R_x$ and optionally substituted with 1–2 $R^q$ groups, provided that at least one of $R^1$ or $R^2$ contains an $R^q$, wherein all other variables are as described above.

Another subset of compounds of formula I which is of interest relates to those compounds where $R^1$ and/or $R^2$ represents a group of the formula:

(c)

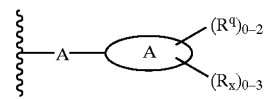

wherein at least one $R^q$ is present on $R^1$ or $R^2$ and all other variables are defined as above.

Another subset of compounds of formula I which is of interest relates to those compounds where $R^1$ and/or $R^2$ represents a group of the formula:

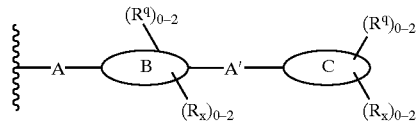

wherein at least one $R^q$ group is present on $R^1$ or $R^2$ and all other variables are defined as above.

Another subset of compounds of formula I which is of interest relates to those compounds where the relative and absolute stereochemistry is:

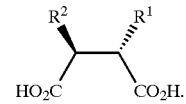

Still another subset of compounds of formula I which is of interest relates to those compounds where $R^1$ and/or $R^2$ represents a group of the formula:

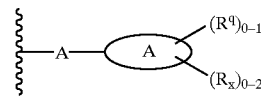

wherein A is $(CH_2)_{1-5}$ and

is phenyl, naphthyl, cyclohexyl or dibenzofuranyl, provided that at least one of $R^1$ or $R^2$ contains an $R^q$ and all other variables are as originally defined.

Still another subset of compounds of formula I that is of interest relates to those compounds where $R^1$ or $R^2$ represents a group of the formula:

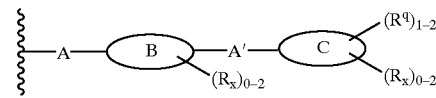

wherein

A is $(CH_2)_{1-3}$, A' is a single bond, —O— or $(CH_2)_{1-2}$ and

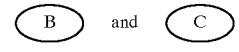

independently represent phenyl, thienyl, pyridyl, furanyl or cyclohexyl.

Yet another subset of compounds of formula I, that is of interest relates to those compounds where one of $R^1$ or $R^2$ is $C_{4-8}$ straight, branched or unsaturated alkyl optionally substituted with 1 to 2 $R_x$ or a group of the formula:

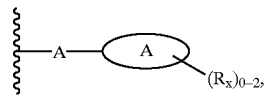

where A is $(CH_2)_{1-2}$ and

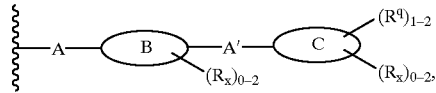

is phenyl, cyclopentyl or cyclohexyl and the other of $R^1$ or $R^2$ is
i) a $C_{7-12}$ alkyl group substituted with $R^q$,
ii) a group of the formula:

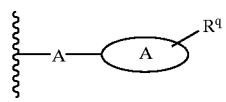

where A is $(CH_2)_{1-2}$, A' is a single bond,

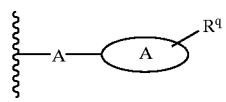

is phenyl, thienyl or cyclohexyl and

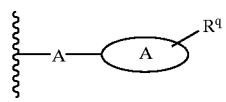

is phenyl, thienyl or pyridyl, or
iii) a group of the formula:

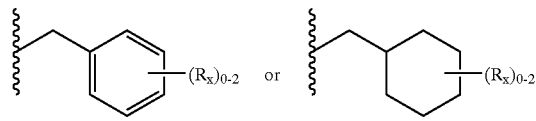

where A is $(CH_2)_{1-3}$,

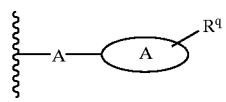

is phenyl or thienyl and $R^q$ is $-(CH_2)_{2-6}-Q^+Y^-$ and all other variables are as originally defined.

Still another subset of compounds of formula I that is of interest relates to those compounds where:
$R^1$ is $C_{5-7}$ alkyl substituted with 0 to 2 $R_x$ goups,

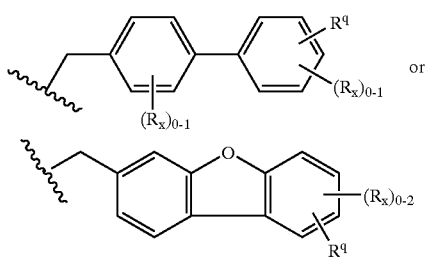

$R^2$ is $C_{7-10}$ alkyl substituted with 1 $R^q$ group and 0 to 2 $R_x$ groups,

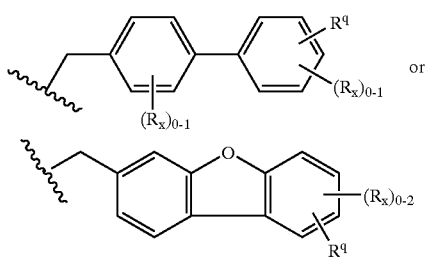

and all other variables are as described above.

Still another subset of compounds of formula I that is of interest relates to those compounds where:
$R^1$ is:

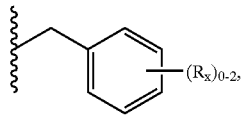

$R^2$ is:

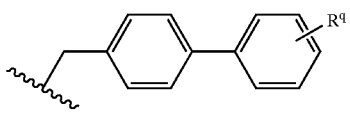

and all other variables are as described above.

A preferred subset of $R_x$ is $R^y$.

It is preferred that a total of one or two $R^q$ groups are present in $R^1$ and $R^2$ containing a total of 2 to 6 cationic nitrogen atoms. It is more preferred that a single $R^q$ substituent is present containing a tricationic or tetracationic $Q^+$ group. A more preferred $R^q$ is $-E-Q^+Y^-$ wherein E is $(CH_2)_{0-6}$ or $-C(O)-N(R^a)-(CH_2)_{2-4}-$, and $Q^+$ is a tricationic or tetracationic group.

Preferred tricationic $Q^+$ groups are:

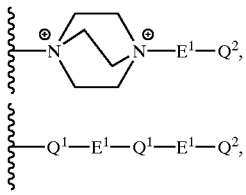

wherein $E^1$ is $(CH_2)_{2-4}$ or $-(CH_2)-C(O)-N(R^a)-(CH_2)_{2-4}-$ and $R^a$, $Q^1$ and $Q^2$ are as previously defined.

More preferred tricationic $Q^+$ groups are:

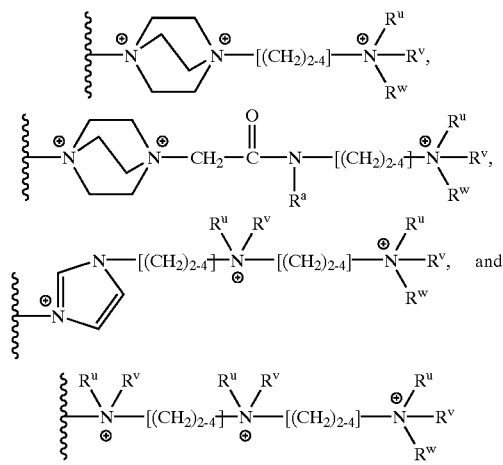

wherein $R^a$, $R^u$, $R^v$, and $R^w$ are independently selected as defined above.

Preferred tetracationic $Q^+$ groups are:

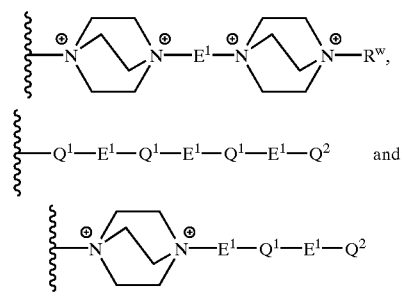

wherein $E^1$ is $(CH_2)_{2-4}$ or $-(CH_2)-C(O)-N(R^a)-(CH_2)_{2-4}-$ and $R^a$, $Q^1$, $Q^2$, and $R^w$ are as defined above.

More preferred tetracationic $Q^+$ groups are:

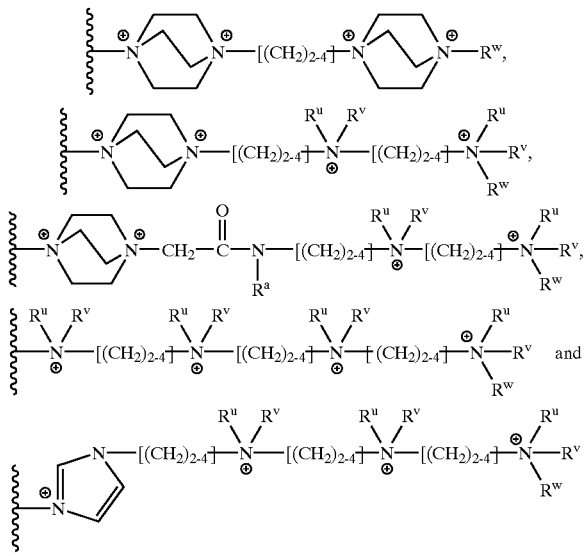

wherein $R^a$, $R^u$, $R^v$, and $R^w$ are as defined above.

Preferred $Y^-$ groups are chloride, bromide, acetate, citrate, succinate, phosphate, maleate, tartrate and sulfate.

The compounds of the invention, which are succinic acids or derivatives thereof, can be formulated in pharmaceutical compositions by combining the compound with a pharmaceutically acceptable carrier. Examples of such carriers are set forth below. The compounds of formula I have metallo-β-lactamase inhibitory properties, and are useful when combined with a β-lactam antibiotic for the treatment of infections in animals, especially mammals, including humans. The compounds may be used, for example, in the treatment of infections of, amongst others, the respiratory tract, urinary tract and soft tissues and blood.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral composions may utilize carriers such as conventional formulating agents, and may include sustained release properties as well as rapid delivery forms.

The compounds of the instant invention are metallo-β-lactamase inhibitors, which are intended for use in pharmaceutical compositions. Accordingly, it is preferable that the metallo-β-lactamase inhibitors are provided in substantially pure form, for example at least about 60% to about 75% pure, preferably about 85% to about 95% pure and most preferably about 98% or more pure (% are on a weight for weight basis). Impure preparations of the compounds may be used for preparing the more pure forms used in pharmaceutical compositions.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in conjunction with a β-lactam antibiotic such as a carbapenem, penicillin or cephalosporin in an effective combination.

The preferred methods of administration of the Formula I compounds include oral and parenteral, e.g., i.v. infusion, i.v. bolus and i.m. injection.

The compounds of formula I may suitably be administered to the patient at a daily dosage of from 0.7 to 50 mg/kg of body weight. For an adult human (of approximately 70 kg body weight), from 50 to 3000 mg, preferably from 100 to 1000 mg, of a compound according to the invention may be administered daily, suitably in from 1 to 6, preferably from 2 to 4, separate doses. Higher or lower dosages may, however, be used in accordance with clinical practice.

The compounds may be used in combination with antibiotic agents for the treatment of infections caused by metallo-β-lactamase producing strains, in addition to those infections which are subsumed within the antibacterial spectrum of the antibiotic agent. Metallo-β-lactamase producing strains include: *Bacillus cereus, Bacteroides fragilis, Aeromonas hydrophila, Klebsiella pneumoniae, Pseudomonas aeruginosa, Serratia marcescens, Stenotrophomonas maltophilia, Shigellaflexneri, Legionella gormanii, Chryseobacterium meningosepticum, Chryseobacterium indologenes, Acinetobacter baumannii, Citrobacterfreundii,* and *Aeromonas veronii.*

In accordance with the instant invention, it is generally advantageous to use a compound of formula I in admixture or conjuction with a carbapenem, penicillin, cephalosporin or other β-lactam antibiotic or prodrug. It also advantageous to use a compound of formula I in combination with one or more β-lactam antibiotics, because of the metallo-β-lactamase inhibitory properties of the compounds. In this case, the compound of formula I and the β-lactam antibiotic can be administered separately or in the form of a single composition containing both active ingredients.

Carbapenems, penicillins, cephalosporins and other β-lactam antibiotics suitable for co-administration with the compounds of Formula I, whether by separate administration or by inclusion in the compositions according to the invention, include both those known to show instability to or to be otherwise susceptible to metallo-β-lactamases and also known to have a degree of resistance to metallo-β-lactamase.

When the compounds of Formula I are combined with antibiotics such as carbapenems dehydropeptidase (DHP) inhibitors may also be combined. Many carbapenems are susceptible to attack by a renal enzyme known as DHP. This attack or degradation may reduce the efficacy of the carbapenem antibacterial agent. Inhibitors of DHP and their use with carbapenems are disclosed in, e.g., (European Patent 0007614, filed Jul. 24, 1979 and application number 82107174.3, filed Aug. 9, 1982. A preferred DHP inhibitor is 7-(L-2-amino-2-carboxyethylthio)-2-(2,2-dimethylcyclopropanecarboxamide)-2-heptenoic acid or a useful salt thereof. Thus, compounds of the present invention in combination with a carbapenem such as imipenem and a DHP inhibitor such as, cilastatin is contemplated within the scope of this invention.

A serine β-lactamase inhibitor such as clavulanic acid, sulbactam or tazobactam may also be co-administered with the compound of the invention and β-lactam antibiotics, either by separate administration, or co-formulation with one, other or both of the compounds of the invention and the β-lactam antibiotic.

Examples of carbapenems that may be co-administered with the compounds of formula I include imipenem, meropenem, biapenem, (4R,5S,6S)-3-[3S,5S)-5-(3-carboxyphenyl-carbamoyl)pyrrolidin-3-ylthio]-6-(1R)-1-hydroxyethyl]-4-methyl-7-oxo-1-azabicyclo[3.2.0]hept-2-ene-2-carboxylic acid, (1S,5R,6S)-2-(4-(2-(((carbamoylmethyl)-1,4-diazoniabicyclo[2.2.2]oct-1-yl)-ethyl(1,8-naphthosultam)methyl)-6-[1(R)-hydroxyethyl]-1-methylcarbapen-2-em-3-carboxylate chloride, BMS181139 ([4R-[4alpha,5beta,6beta(R*)]]-4-[2-[(aminoiminomethyl) amino]ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*,5S*(R*)], 4alpha,5beta,6beta(R*)]]-6-(1-hydroxyethyl)-3-[[5-[1-hydroxy-3-(methylamino) propyl]-3-pyrrolidinyl]thio]-4-methyl-7-oxo-1-azabicyclo [3.2.0] hept-2-ene-2-carboxylic acid monohydrochloride), E1010 ((1R,5S,6S)-6-[1(R)-hydroxymethyl]-2-[2(S)-[1(R)-hydroxy-1-[pyrrolidin-3(R)-yl]methyl]pyrrolidin-4(S)-ylsulfanyl]-1-methyl-1-carba-2-penem-3-carboxylic acid hydrochloride), S4661((1R,5S,6S)-2-[(3S,5S)-5-(sulfamoylaminomethyl)pyrrolidin-3-yl]thio-6-[(1R)-1-hydroxyethyl]-1-methylcarbapen-2-em-3-carboxylic acid) and (1S,5R,6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)-carbapen-2-em-3-carboxylate chloride.

Examples of penicillins suitable for co-administration with the compounds according to the invention include benzylpenicillin, phenoxymethylpenicillin, carbenicillin, azidocillin, propicillin, ampicillin, amoxycillin, epicillin, ticarcillin, cyclacillin, pirbenicillin, azloccillin, mezlocillin, sulbenicillin, piperacillin, and other known penicillins. The penicillins may be used in the form of pro-drugs thereof; for example as in vivo hydrolysable esters, for example the acetoxymethyl, pivaloyloxymethyl, α-ethoxycarbonyloxyethyl and phthalidyl esters of ampicillin, benzylpenicillin and amoxycillin; as aldehyde or ketone adducts of penicillins containing a 6-α-aminoacetamido side chain (for example hetacillin, metampicillin and analogous derivatives of amoxycillin); and as a-estsers of carbenicillin and ticarcillin, for example the phenyl and indanyl α-esters.

Examples of cephalosporins that may be co-administered with the compounds according to the invention include, cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefinetazole, cefotaxime, ceftriaxone, and other known cephalosporins, all of which may be used in the form of pro-drugs thereof.

Examples of β-lactam antibiotics other than penicillins and cephalosporins that may be co-administered with the compounds according to the invention include aztreonam, latamoxef (Moxalactam-trade mark), and other known β-lactam antibiotics such as carbapenems like imipenem, meropenem or (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, all of which may be used in the form of pro-drugs thereof.

Preferred carbapenems are imipenem, meropenem and (4R,5S,6S)-3-[(3S,5S)-5-(3-carboxyphenylcarbamoyl) pyrrolidin-3-ylthio]-6-(1R)-1-hydroxyethyl]-4-methyl-7-oxo-1-azabicyclo[3.2.0]hept-2-ene-2-carboxylic acid.

Particularly suitable penicillins for co-administration with the compounds according to the invention include ampicillin, amoxycillin, carbenicillin, piperacillin, azlocillin, mezlocillin, and ticarcillin. Such penicillins may be used in the form of their pharmaceutically acceptable salts, for example their sodium salts. Alternatively, ampicillin or amoxycillin may be used in the form of fine particles of the zwitterionic form (generally as ampicillin trihydrate or amoxycillin trihydrate) for use in an injectable or infusable suspension, for example, in the manner described herein in relation to the compounds of formula I. Amoxycillin, for example in the form of its sodium salt or the trihydrate, is particularly preferred for use in compositions according to the invention.

Particularly suitable cephalosporins for co-administration with the compounds according to the invention include cefotaxime, ceftriaxone and ceftazidime, which may be used in the form of their pharmaceutically acceptable salts, for example their sodium salts.

When the compositions according to this invention are presented in unit dosage form, each unit dose may suitably comprise from about 25 to about 1000 mg, preferably about from 50 to about 500 mg, of a compound according to the invention. Each unit dose may, for example, be 62.5, 100, 125, 150, 200 or 250 mg of a compound according to the invention.

When the compounds of formula I are co-administered with a penicillin, cephalosporin, carbapenem or other β-lactam antibiotic, the ratio of the amount of the compounds of formula I to the amount of the other β-lactam antibiotic may vary within a wide range. The said ratio may, for example, be from 100:1 to 1:100; more particularly, it may for example, be from 2:1 to 1:30. The amount of carbapenem, penicillin, cephalosporin or other β-lactam antibiotic according to the invention will normally be approximately similar to the amount in which it is conventionally used.

The claimed invention also includes the use of a compound of formula I, a pharmaceutically acceptable salt, ester, prodrug, anhydride or solvate thereof, in the manufacture of a medicament for the treatment of bacterial infections.

The claimed invention also includes the use of a compound of formula I as a metallo-β-lactamase inhibitor.

The claimed invention further includes a method of treating bacterial infections in humans or animals which comprises administering, in combination with a β-lactam antibiotic, a therapeutically effective amount of a metallo-β-lactamase inhibitor of formula I.

The claimed invention further includes a method of treating bacterial infections in humans or animals which comprises administering, in combination with a carbapenem antibiotic, a therapeutically effective amount of a metallo-β-lactamase inhibitor of formula I.

The claimed invention also includes a composition comprising a metallo-β-lactamase inhibitor of formula I together with a β-lactam antibiotic and a pharmaceutically acceptable carrier.

The claimed invention also includes a composition comprising a metallo-β-lactamase inhibitor of formula I together with a carbapenem antibiotic and a pharmaceutically acceptable carrier.

The compositions discussed above may optionally include a serine β-lactamase inhibitor as described above as well as a DHP inhibitor.

Using standard susceptibility tests the compounds of the instant invention were found to be active against metallo-β-lactamase enzymes produced by a range of organisms.

The compounds of the present invention are synthesized using the general conditions shown in the accompanying flow charts (A through F).

FLOW SHEET A

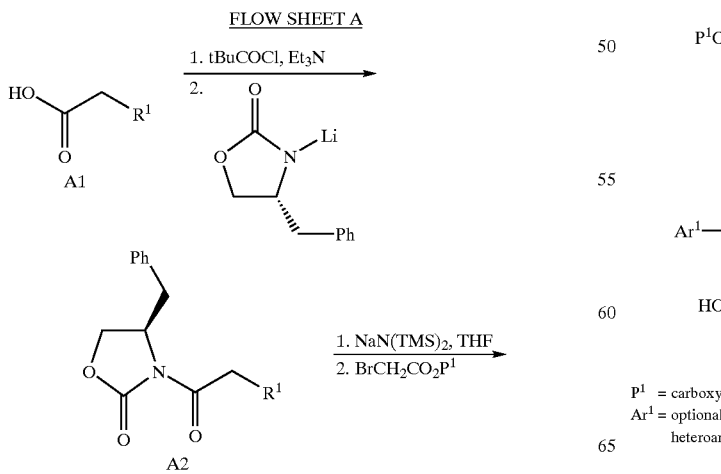

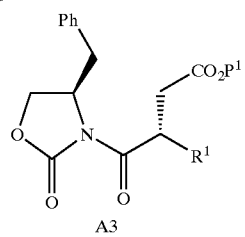

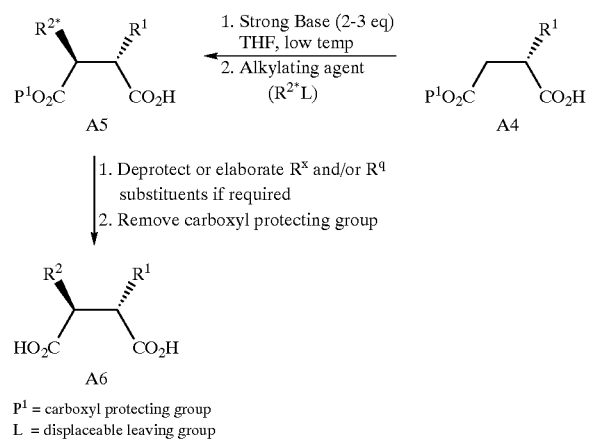

$P^1$ = carboxyl protecting group
L = displaceable leaving group

FLOW SHEET B

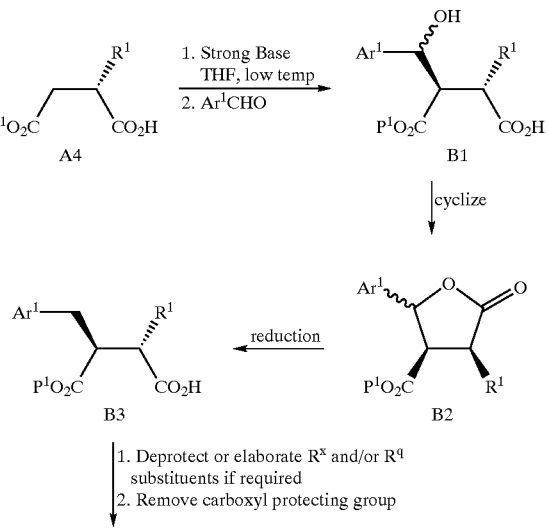

$P^1$ = carboxyl protecting group
$Ar^1$ = optionally substituted aryl or heteroaryl group

FLOW SHEET C

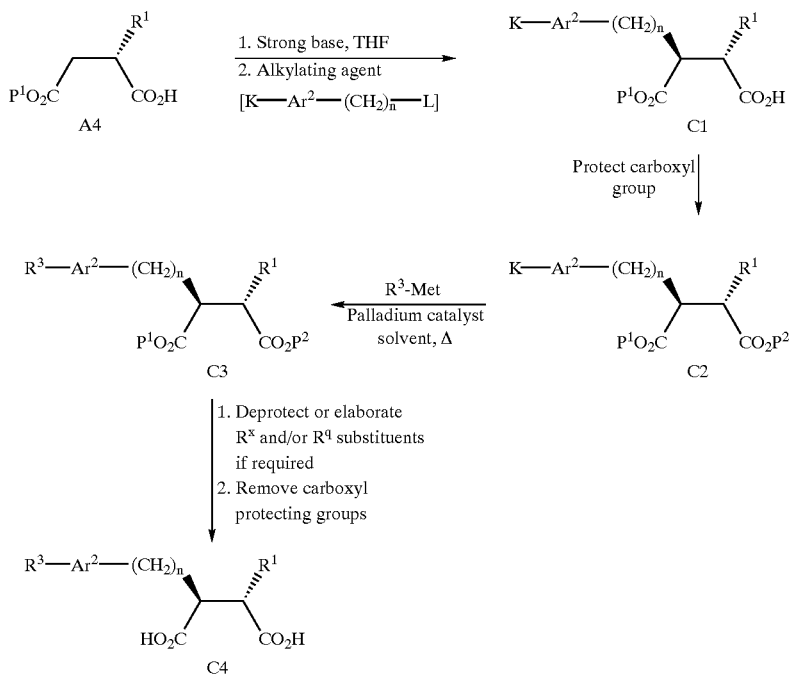

L = displaceable leaving group
Ar² = optionally substituted aryl or heteroaryl group
K = iodide, bromide, chloride, protected hydroxy
n = 1, 2, 3 or 4
R³ = optionally substituted alkenyl, alkenyl,
    aryl or heteroaryl group
Met = boronic acid or trialkyltin moiety
P¹ = carboxyl protecting group
P² = carboxyl protecting group

FLOW SHEET D

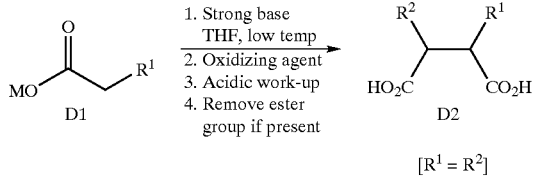

M = H or esterifying group

FLOW SHEET E

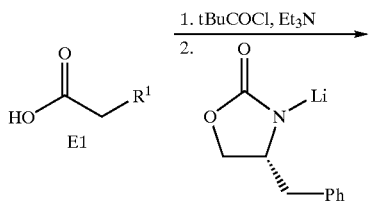

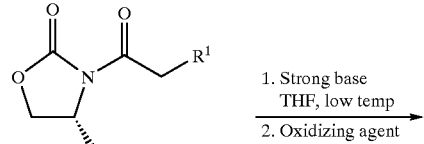

-continued

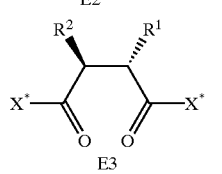

FLOW SHEET F

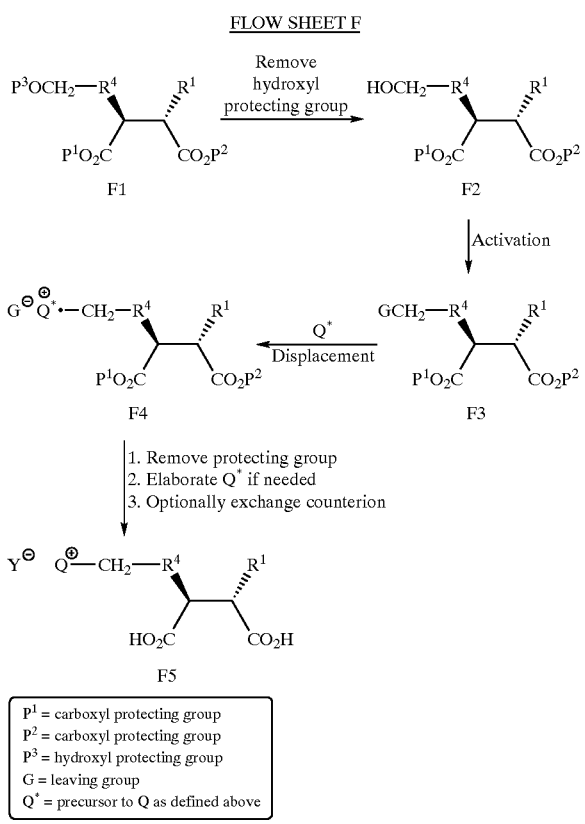

$P^1$ = carboxyl protecting group
$P^2$ = carboxyl protecting group
$P^3$ = hydroxyl protecting group
G = leaving group
$Q^*$ = precursor to Q as defined above The 2,3-disubstituted succinic acid compounds of the present invention can be prepared as described in Flow Sheets A–F. The cationic $R^q$ substituents of the compounds of the present invention are generally carried through the syntheses in protected or precursory form and are then deprotected or elaborated near or at the end of the synthesis. Introduction of the $R^q$ substituent from a precursor group is described in detail in Flow Sheet F.

The synthesis of Flow Sheet A is based on a known literature procedure (M. J. Crimmin et. al., *SynLett* 1993, 137). Referring to Flow Sheet A, the $R^1$-substituted acetic acid starting materials A1 are readily available from commercial sources or are readily prepared by a variety of methods known in the art. Briefly, the starting material A1 is alkylated with an ester derivative of bromoacetic acid, employing a chiral auxiliary group to achieve stereoselectivity in the reaction. After removal of the chiral auxiliary to give A4, the $R^{2*}$ group is introduced stereoselectively by an alkylation reaction to give A5. The $R^{2*}$ group may be $R^2$ as defined above, or may contain $R_x$ and $R^q$ substituents in precursory or protected form which require elaboration. Such elaboration may be carried-out at this point. Removal of the carboxyl protecting group of A5 then provides the final compound A6.

The first step of Flow Sheet A is introduction of the chiral auxiliary. A suggested method is as follows. A mixed anhydride is formed between the starting carboxylic acid A1 and pivalic acid by treating A1 with a tertiary amine base such as triethylamine and pivaloyl chloride in a suitable ethereal solvent such as tetrahydrofuran at reduced temperature such as between −78° C. and 0° C. After a suitable reaction time, such as from 30 min to 3 hours, the resulting activated intermediate is then reacted with a freshly prepared solution of lithio-(4R)-benzyl-2-oxazolidinone in tetrahydrofuran at reduced temperature such as between −78° C. and 0° C. After conventional isolation and purification, intermediate A2 is obtained. Intermediate A2 is deprotonated with a strong base such as sodium hexamethyldisilazide in a solvent such as tetrahydrofuran at reduced temperature such as between −78° C. and −70° C. The resulting enolate is alkylated by addition of $BrCH_2CO_2P^1$, where $P^1$ is a removable carboxyl protecting group. After an appropriate reaction period, such as from 1 to 3 hours, compound A3 is obtained by conventional isolation and purification techniques. Suitable removable ester derivatives of bromoacetic acid for this alkylation reaction are t-butyl bromoacetate, allyl bromoacetate or benzyl bromoacetate.

The oxazolidinone chiral auxiliary group of A3 is removed by a hydrolysis reaction. Aqueous lithium hydroxide and aqueous hydrogen peroxide are employed for this reaction along with an organic co-solvent such as tetrahydrofuran. The reaction is carried-out at a temperature of from 0° C. to 30° C. for a reaction time of from 30 min to 4 hours. After acidification, conventional isolation and purification provides intermediate A4.

An alternative method of removing the chiral auxilliary consists of reacting A3 with lithium benzyloxide ($LiOCH_2Ph$) followed by cleavage of the resulting benzyl ester to give A4. The reaction of A3 with lithium benzyloxide is carried-out in tetrahydrofuran as solvent at a temperature of from −78° C. to 30° C. for a reaction time of from 30 min to 4 hours. Cleavage of the resulting benzyl ester is accomplished in conventional fashion, eg by hydrogenolysis employing a suitable catalyst such as palladium on carbon in an appropriate solvent such as ethanol at 1–2 atmospheres pressure of hydrogen. After conventional isolation and purification, compound A4 is obtained.

Alkylation of A4 to give A5 is accomplished by deprotonating A4 with >2 equivalents of a strong hindered base to give a dianion which is then reacted with an alkylating agent $R^{2*}L$ to give A5, where $R^{2*}$ is as defined above and L is a displaceable leaving group such as iodide, bromide or trifluoromethanesulfonate. The reaction proceeds with high stereoselectivity to give predominately the stereoisomer shown in Flow Sheet A. The deprotonation reaction is carried-out in a suitable solvent such as tetrahydrofuran at a temperature of from −78° C. to −70° C. for a reaction time of from 30 min to 3 hours. Preferred bases for this reaction are lithium bis(trimethylsilyl)amide and lithium diisopropylamide. After addition of the alkylating agent, the reaction is allowed to proceed at a temperature of from −78° C. to 25° C. for a reaction time of from 1 to 12 hours. Progress of the reaction can be monitored by conventional analytical methods, eg HPLC and TLC. Preferred alkylating agents for this reaction are alkyl iodides and alkyl bromides. Other suitable alkylating agents are well known in the art and include alkyl trifluoromethanesulfonates, alkyl methanesulfonates and alkyl tosylates. After conventional isolation and purification, intermediate A5 is obtained. The minor stereoisomer produced in this reaction can often be separated from A5 at this stage by conventional chromatographic techniques. However, it is often preferable to carry-out this separation at the stage of A6, after removal of the carboxyl protecting group as described below.

Deprotection of any $R_x$ or $R^q$ groups which are present in protected form may be accomplished at this point. For example, if compound A5 contains a protected hydroxyl or amino group, said protecting group may conveniently be removed at the stage of A5. Alternatively, depending on the nature of the protecting group it may be removed concurrent with or subsequent to the removal of the carboxyl protecting group as described immediately below. Introduction of the cationic $R^q$ group may also be accomplished at this point from a precursor substituent. This procedure is described in detail in Flow Sheet F further below.

Removal of the carboxyl protecting group of A5 by standard methods gives the final compound A6. When $P^1$ is t-butyl, this is accomplished by treating A5 with a strong acid such as trifluoroacetic acid in a suitable solvent such as dichloromethane. The reaction is carried-out at a temperature of from 0° C. to 30° C. for a reaction time of from 1 to 8 hours. The final compound A6 is then isolated by conventional techniques. Other methods of removing tert-butyl ester groups are known in the art and may also be employed (see e.g. Greene, T. W., et al. *Protective Groups in Organic Synthesis*, John Wiley & Sons. Inc., 1991).

It will be apparent to one skilled in the art that employing a chiral auxiliary of the opposite absolute configuration [e.g. lithio-(4S)-benzyl-2-oxazolidinone] in the first step of Flow Sheet A will make possible the synthesis of compound A3 with the alternative stereochemistry at the newly created stereocenter. This will in turn make possible the synthesis of the final compounds A6 of Flow Sheet A, with the opposite absolute configuration. Other chiral auxiliary groups are also known in the art and may also be employed.

Flow Sheet B illustrates a variation of Flow Sheet A which is preferred in certain cases, for example when $Ar^1$ is a heteroaryl group such as pyridyl. In this synthesis the second substituent on the succinic acid is introduced by an aldol reaction instead of an alkylation reaction. The synthesis begins with compound A4, which is prepared as described in Flow Sheet A. Compound A4 is deprotonated with >2 equivalents of a strong hindered base to give a dianion which is then reacted with an aldehyde $Ar^1CHO$ to give B1, where $Ar^1$ is an optionally substituted aryl or heteroaryl group, terms which are defined above. The deprotonation reaction is carried-out in a suitable solvent such as tetrahydrofuran at a temperature of from −78° C. to −70° C. for a reaction time of from 30 min to 3 hours. Preferred bases for this reaction are lithium bis(trimethylsilyl)amide and lithium diisopropylamide. After addition of the aldehyde, the reaction is allowed to proceed at a temperature of from −78° C. to 25° C. for a reaction time of from 1 to 12 hours. After conventional isolation and purification, intermediate B1 is obtained.

Compound B1 is next cyclized to the lactone B2. Suitable conditions for this cyclization reaction would be exposure of B1 to acetic anhydride and triethylamine in an inert solvent such as dichloromethane. Reductive opening of lactone B2, such as by hydrogenolysis over palladium on carbon in a suitable solvent such as methanol, provides compound B3. Deprotection of any $R_x$ or $R^q$ groups which are present in protected form may be accomplished at this point. In addition, introduction of a cationic $R^q$ group from a precursor substituent may be carried-out at the stage of B3. This procedure is described in detail in Flow Sheet F further below. Removal of the carboxyl protecting group of B3 by conventional methods then gives the final compound B4.

Flow Sheet C illustrates an extension of the synthesis of Flow Sheet A which makes possible the introduction of a variety of preferred biaryl-type $R^2$ substituents. Briefly, starting with compound A4 from Flow Sheet A, alkylation with K—$Ar^2$—$(CH_2)_n$—L by the method described in Flow Sheet A gives intermediate C1; where L is a displaceable leaving group such as iodide, bromide or trifluoromethanesulfonate, n is 1,2,3 or 4, $Ar^2$ is an optionally substituted aryl or heteroaryl group as defined above, and K is iodide, bromide, chloride or a protected hydroxyl group which can be converted to a trifluoromethanesulfonate group by known methods. Protection of the free carboxyl group of C1 with a removable protecting group $P^2$ gives C2. When K is a protected hydroxyl group it is deprotected and converted to a trifluoromethanesulfonate group at this point. A palladium catalyzed organometallic cross-coupling reaction between C2 and an organometallic reagent $R^3$-Met gives compound $C_3$; where Met is a boronic acid or trialkyltin moiety and $R^3$ is an optionally substituted alkenyl, alkynyl, aryl or heteroaryl group as defined above. Deprotection or elaboration of any $R_x$ or $R^q$ groups which are present in protected or precursor form is accomplished at this point. Removal of the two carboxyl protecting groups of C3 then provides the final compound C4.

The $P^2$ carboxyl protecting group is introduced in conventional fashion. A preferred $P^2$ group is p-methoxybenzyl which can be introduced employing p-methoxybenzyl alcohol, a carbodiimide reagent such as 1,3-diisopropylcarbodiimide and N,N-dimethylaminopyridine catalyst in a suitable inert solvent such as dichloromethane. Other suitable ester protecting groups known in the art could also be employed (see e.g. Greene, T. W., et al. *Protective Groups in Organic Synthesis*, John Wiley & Sons. Inc., 1991).

The palladium catalyzed cross-coupling reaction between C2 and $R^3$-Met is carried-out by procedures known in the scientific and patent literature. When Met is a boronic acid moiety [—$B(OH)_2$] the reaction is commonly known as a Suzuki reaction (see Suzuki, *Chem. Rev.* 1995, 95, 2457). Compound C2 is combined with the boronic acid $R^3$—B(OH)$_2$ in a coupling solvent such as 1,2-dimethoxyethane, N,N-dimethylformamide or toluene, optionally with water as a co-solvent, with a base such as sodium carbonate and a palladium catalyst such as tetrakis(triphenylphosphine)-palladium(0). The reaction is carried-out at a temperature of from 20° C. to 125° C. for a reaction time of from 1 to 48 hours. The coupled product C3 is then isolated by conventional techniques. When Met is a trialkyltin moiety, the reaction is commonly known as a Stille reaction and the cross-coupling is carried-out by procedures well known in the literature (T. N. Mitchell, *Synthesis* 1992, 803).

Deprotection of any $R_x$ or $R^q$ groups which are present in protected form may be accomplished at this point. In addition, introduction of a cationic $R^q$ group from a precursor substituent may be carried-out at the stage of C3. This procedure is described in detail in Flow Sheet F further below.

Removal of the carboxyl protecting groups of C3 by standard methods provides the final compound C4. It is often convenient for the protecting groups $P^1$ and $P^2$ to be selected such that they can both be removed under the same reaction conditions. For example, when $P^1$ is tert-butyl and $P^2$ is p-methoxybenzyl, both esters of C3 can be removed in a single step by treating C3 with a strong acid such as trifluoroacetic acid in a suitable solvent such as dichloromethane. It is sometimes advantageous to include a trapping agent such as triethylsilane or anisole in the reaction mixture. The reaction is carried-out at a temperature of from 0° C. to 30° C. for a reaction time of from 1 to 8 hours. The final compound C4 is then isolated by conventional techniques. Other methods of removing tert-butyl and p-methoxybenzyl ester groups are known in the art and may also be employed (see e.g. Greene, T. W., et al. *Protective Groups in Organic Synthesis*, John Wiley & Sons. Inc., 1991). Flow Sheet D illustrates an alternative synthesis of compounds of the present invention. The $R^1$-substituted acetic acid starting materials D1 (M=H) and the esterified derivatives thereof (M=esterifying group) are readily available from commercial sources or are readily prepared by a variety of methods known in the art. The synthesis of Flow Sheet D is based on known literature procedures (see for example J. L. Belletire and D. F. Fry, *J. Org. Chem.* 1987, 52, 2549). Briefly, starting material D1 is deprotonated with a strong base and the resulting dianion (M=H) or anion (M=esterifying group) is oxidatively coupled with a suitable oxidizing reagent. In the case of M=H, acidic work-up and conventional isolation and purification gives the final compound D2. In the case of M=esterifying group, an additional deprotection step is also needed. A preferred strong base for the deprotonation reaction is lithium diisopropylamide. Suitable oxidizing agents for the synthesis of Flow Sheet D include iodine, copper(II) salts such as $CuBr_2$, and titanium tetrachloride.

In the synthesis of Flow Sheet D, protection or elaboration of any $R^x$ or $R^q$ groups which are present in protected or precursory form is best accomplished where M=esterifying group, prior to removal of said esterifying group. In addition, introduction of a cationic $R^q$ group from a precursor substituent may be carried-out as described in detail in Flow Sheet F further below.

Since the synthesis of Flow Sheet D is based on a dimerization-type reaction, it is best suited for the synthesis of symmetrically 2,3-disubstituted succinic acids ($R^1=R^2$). For this reason, it is generally less preferred than the syntheses of Flow Sheets A, B and C. The synthesis of Flow Sheet D also generally produces a racemic mixture of stereoisomers. However, it is possible to employ a chiral auxiliary in the synthesis of Flow Sheet D in order to achieve high stereoselectivity and optical purity (see for example N. Kise et. al. *J. Org. Chem.* 1995, 60, 1100). Such use of a chiral auxiliary is illustrated in Flow Sheet E.

Flow Sheet F illustrates a suggested method for the introduction of the cationic substituents of the compounds of the present invention from a precursor substituent. The starting material F1 of Flow Sheet F is substituted with a precursor substituent which can be elaborated into the desired cationic substitutent, $R^q$. A preferred precursor substituent is a protected hydroxymethyl group, $P^3OCH_2$—, where $P^3$ is a removable hydroxyl protecting group. In Flow Sheet F, $R^4$ is defined such that the moiety [—$R^4$—$CH_2$—$Q^+Y^-$] represents an $R^2$ group as defined above. Examples of representative $R^4$ groups are shown in Table 1.

The starting material F1 of Flow Sheet F is synthesized by one of the methods described in Flow Sheets A, B, C, D, and E. When F1 is synthesized according to Flow Sheet A, it is derived from intermediate A5, through protection of the free carboxyl group with an appropriate carboxyl protecting group $P^2$. In this case, the precursor substituent is present in the $R^1$ or $R^{2*}$ substituent of A5. When F1 is synthesized according to Flow Sheet B, it is derived from intermediate B3, through protection of the free carboxyl group with an appropriate carboxyl protecting group $P^2$. In this case, the precursor substituent is present in the $R^1$ or $Ar^1$ substituent of B3. When F1 is synthesized according to Flow Sheet C, it is derived from or corresponds to, intermediate C3. In this case, the precursor substituent is present in the $R^1$, $Ar^2$ or $R^3$ substituent of C3. Starting material F1 may also be prepared by appropriate modification of the syntheses of Flow Sheets D and E as would be apparent to those skilled in the art.

Referring to Flow Sheet F, the first step is removal of the hydroxyl protecting group $P^3$. This is accomplished by conventional methods. Hydroxyl protecting group $P^3$ is generally selected such that it may be selectively removed in the presence of the carboxyl protecting groups $P^1$ and $P^2$. A preferred $P^3$ is t-butyldimethylsilyl. Removal of the preferred t-butyldimethylsilyl $P^3$ is accomplished by treating F1 with tetra-n-butylammonium fluoride and acetic acid in tetrahydrofuran as solvent. Other hydroxyl protecting groups are well known in the art and may also be employed (see e.g. Greene, T. W., et al. *Protective Groups in Organic Synthesis*, John Wiley & Sons. Inc., 1991).

Introduction of the cationic substituent is accomplished by an activation-dispacement process. Briefly, the hydroxyl group of F2 is converted into a suitable leaving group, G, which is thereafter displaced with a nucleophilic nitrogen compound Q*, to yield F4. With certain Q* groups, additional steps may also be needed such as removal of amino protecting groups or conversion of an amine precursor such azide into an amino group. The protecting groups are removed from F4 in conventional fashion and then in an optional step a pharmaceutically acceptable counterion $Y^-$ may be introduced to provide compound F5.

The following are examples of suitable leaving groups G: alkyl and substituted alkylsulfonates, aryl and substituted arylsulfonates and halides. The common sulfonate leaving groups are: methanesulfonyloxy, trifluoromethanesulfonyloxy, fluorosulfonyloxy, p-toluenesulfonyloxy, and 2,4,6-triisopropylbenzenesulfonyloxy. The preferred halogen leaving groups are bromide and iodide.

Compound Q* represents a precursor group to the cationic group $Q^+$ as defined above. As such, it may require further modification after its reaction with F3. The nucleophilic nitrogen moiety of Q* is generally the nitrogen of a primary, secondary or tertiary amino group or a ring nitrogen of a heteroaryl group such as a 1-substituted-imidazole. In addition to its nucleophilic nitrogen atom, Q* may include 1,2 or 3 of the following moieties: positively charged nitrogen atoms, protected amino groups, amine precursor groups such as azido. Suitable protecting groups for amino groups present in Q* would be t-butyloxycarbonyl-, allyloxycarbonyl- and p-nitrobenzyloxycarbonyl-. The Q* groups may be prepared by standard methods known in the scientific and patent literature. Suitable Q* groups are listed in Table 2.

Referring to Flow Sheet F, the hydroxyl group of F2 may be converted into a suitable alkyl- or arylsulfonate leaving group by treating with an appropriate agent such as an alkyl- or arylsulfonyl chloride or an alkyl- or arylsulfonic anhydride in the presence of a hindered organic base such as triethylamine or 2,6-lutidine. A suitable solvent such as dichloromethane is employed and the reaction is carried out at reduced temperature, such as from about −70° C. to 0° C.

The preferred halogen leaving groups may be introduced by displacing an alkyl- or arylsulfonate leaving group with an appropriate metal halide. Thus, compound F3, where G is an alkyl- or arylsulfonate group, is reacted with a suitable metal halide such as sodium iodide or potassium bromide in a suitable solvent such as acetone, acetonitrile, tetrahydrofuran, 1-methyl-2-pyrrolidinone and the like, at from about 0° C. to 50° C. Alternatively, the hydroxyl group of F2 may be directly converted into an iodide group by reaction with an appropriate reagent, e.g. by treatment of F2 with methyl triphenoxyphosphonium iodide in a suitable solvent, such as N,N-dimethylformamide, at reduced or ambient temperatures. Introduction of the cationic substituent is accomplished by reacting F3 with a nucleophilic nitrogen compound Q* in a suitable solvent, such as acetonitrile, tetrahydrofuran, 1-methyl-2-pyrrolidinone and the like, at about 0° C. to 50° C. to provide F4. When the leaving group, G, is iodide or bromide, this displacement reaction may also be facilitated by the addition of silver trifluoromethanesulfonate to the reaction mixture.

When the hydroxyl group of F2 is located at a benzylic position, and the reactive trifluoromethanesulfonate group is employed as the leaving group G in F3, the activation and displacement steps must be carried-out in situ, since in this case F3 cannot be isolated by conventional techniques due to its instability. Thus, treatment of F2 with a slight excess of trifluoromethanesulfonic anhydride in the presence of a hindered, non-nucleophilic base such as 2,6-lutidine, 2,4,6-collidine, or 2,6-di-tert-butyl-4-methyl-pyridine in a suitable solvent, such as dichloromethane or acetonitrile, at from about −78° C. to −20° C. provides for the generation of the trifluoromethanesulfonate activating group. Introduction of the cationic group is then accomplished by reacting the above trifluoromethanesulfonate intermediate in situ with Q* at reduced temperature. It is also possible in certain instances to use the nucleophilic nitrogen compound Q* as the base for the formation of the trifluoromethanesulfonate activating group. In this case, treatment of F2 with trifluoromethanesulfonic anhydride in the presence of at least two equivalents of Q* at reduced temperature such as from −78° C. to 0° C. provides intermediate F4. Examples of Q* which are suitable for use in this manner are 1-methylimidazole and 1,4-diazabicyclo(2.2.2)octane.

Removal of the carboxyl protecting groups of F4 by standard methods provides the final compound F5. If Q* includes one or more protected amino groups, these are removed either before, after or simultaneous with the carboxyl protecting groups depending on the exact nature of the protecting groups. If Q* includes one or more amine precursor groups, these may be converted to the desired amine or amines either before or after removal of the carboxyl protecting groups depending on the nature of the protecting groups. In the case of an azido amine precursor group, this may be accomplished by hydrogenation over a suitable catalyst such as rhodium on carbon. After the protecting groups are removed from F4, and the cationic group Q+ has been fully elaborated, the final compound F5 is isolated by conventional techniques. As an optional final step, a pharmaceutically acceptable counterion Y−, which may differ from G−, may be introduced by standard techniques, e.g. by employing an anion exchange resin. Suitable negatively charged counterions are listed above under the description of pharmaceutically acceptable salts.

Compound F5 is electronically balanced. If more than one positive charge is present in the cationic Q+ group of F5, it is understood that an appropriate amount of negative counterion is Y− present to result in overall electronic balance in the final compound F5. Likewise, it is understood that when the counterion Y− is an anionic species possessing more than one negative charge, then an appropriate amount of Y− is present to result in overall electronic balance in the final compound of Formula I. For example, when Y− is a dianionic species, then one-half of a molar equivalent of Y− is present relative to the succinate moiety.

Representative examples of $R^4$ and Q* are found below in Tables 1 and 2 respectively:

TABLE 1

Representative $P^3OCH_2$—$R^4$ Groups

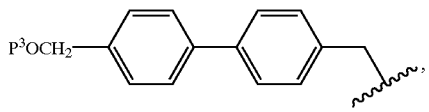

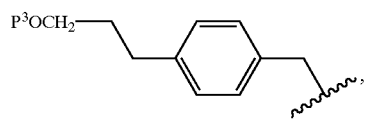

TABLE 1-continued

Representative $P^3OCH_2$—$R^4$ Groups

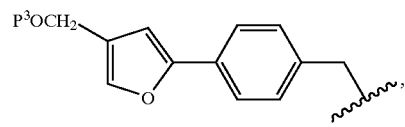

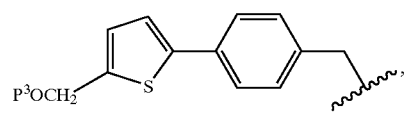

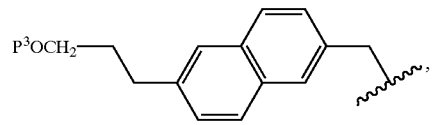

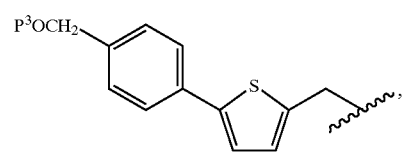

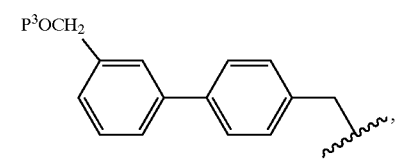

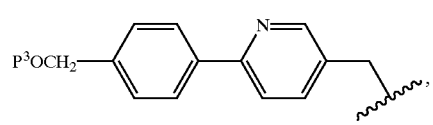

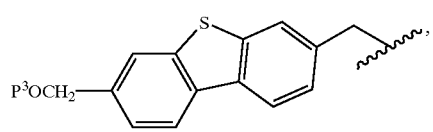

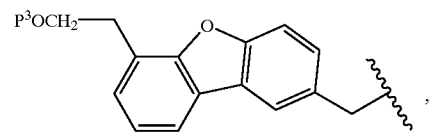

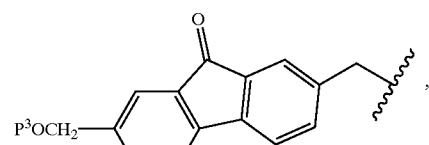

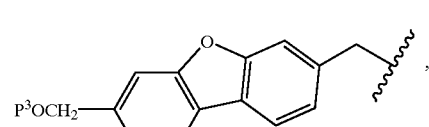

TABLE 1-continued
Representative P³OCH₂—R⁴ Groups
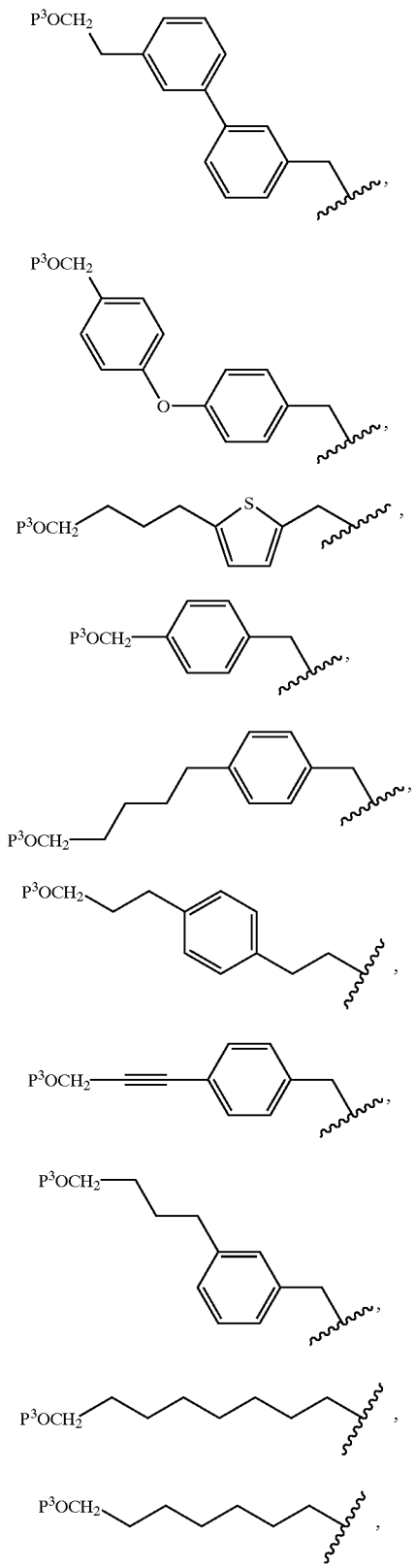
TABLE 1-continued
Representative P³OCH₂—R⁴ Groups
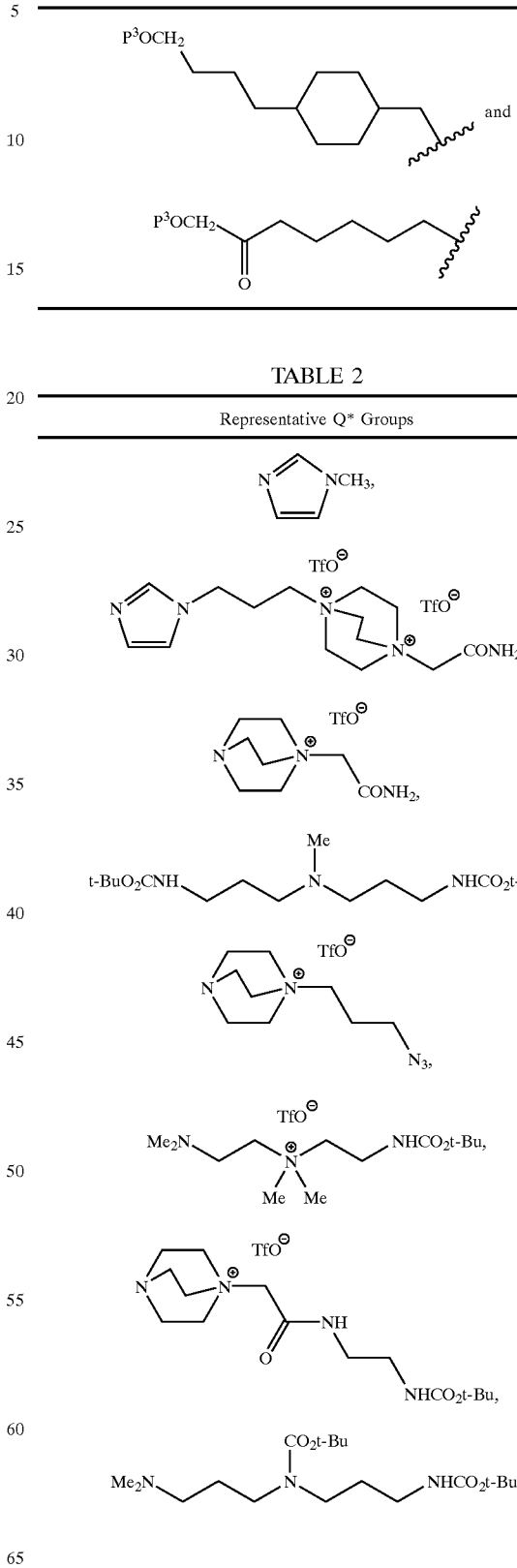

TABLE 2-continued

Representative Q* Groups

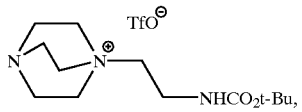

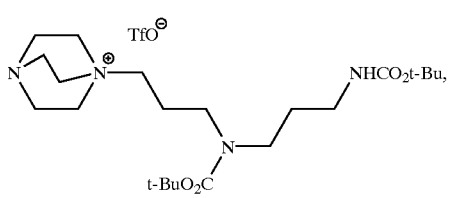

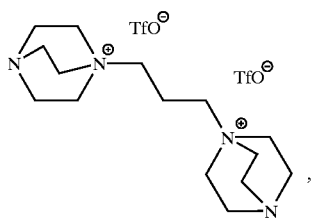

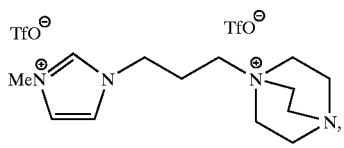

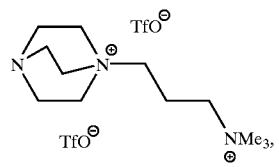

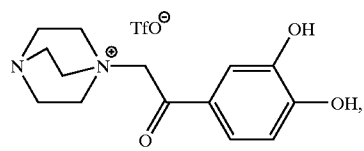

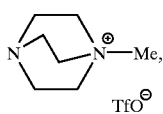

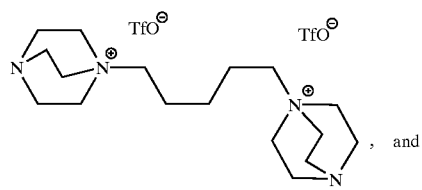, and

The invention is further described in connection with the following non-limiting examples.

PREPARATION 1

Compound 1

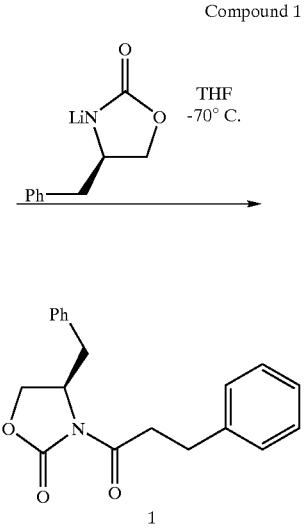

A solution of (4R)-benzyl-2-oxazolidinone (2.44 g, 13.77 mmol) in 100 mL of THF was cooled to −70° C. and metalated by the dropwise addition of a 2.5M solution of n-butyllithium in hexanes (5.52 mL, 13.77 mmol). After 20 min, neat hydrocinnamoyl chloride (2.05 ml, 13.79 mmol) was added. After 15 min, the reaction mixture was warmed by placing in an ice bath and kept at 0° C. C for 1 hr. The reaction was hydrolyzed by the addition of sat. aqueous NH$_4$Cl and most of the THF was removed by rotary evaporation. The residue was partitioned between ethyl acetate and sat. aqueous NH$_4$Cl and the organic phase was washed with sat. aqueous NaHCO$_3$, water and brine. The organic layer was dried over Na$_2$SO$_4$ and evaporated in vacuo to give a solid. Flash chromatography through 500 g of silica gel (50:40:10 hexane/CH$_2$Cl$_2$/EtOAc) yielded 3.89 g of the title compound as a white solid.

$^1$H-NMR (500 Mz, CDCl$_3$): δ 2.79 (dd, J=13.5, 9.4 Hz, 1H), 3.02–3.13 (m, 2H), 3.24–3.41 (m, 3H), 4.16–4.21 (m, 2H), 4.65–4.74 (m, 1H), 7.16–7.40 (m, 10H).

MS (CI): m/z=385.2 (MH$^+$).

PREPARATION 2

Compound 2

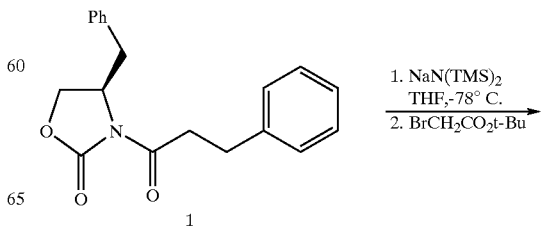

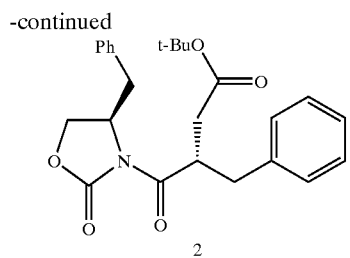

2

A stirred solution of compound 1 (3.283 g, 10.612 mmol) in 35 mL of THF was cooled to −78° C. and a 1.0M solution of NaN(TMS)₂ in THF (11.67 mL, 11.67 mmol) was added dropwise during 15 min. After 30 min, a solution of t-butyl bromoacetate (2.04 mL, 13.82 mmol) in 2 mL of THF was added dropwise during 5 min. The solution was stirred at −78° C. for 1 h and then the ice bath was removed and stirring was continued for 1 h. The reaction was hydrolyzed by the addition of sat. aqueous NH₄Cl and most of the THF was removed by rotary evaporation. The residue was partitioned between ethyl acetate and sat. aqueous NH₄Cl and the organic phase was washed with water and brine. The organic layer was dried over Na₂SO₄ and evaporated in vacuo to give a solid. Flash chromatography through 410 g of silica gel (35:60:5 hexane/CH₂Cl₂/EtOAc) yielded 2.86 g of the title compound as a white foam.

¹H-NMR (500 Mz, CDCl₃): δ 1.43 (s, 9H), 2.41 (dd, J=17.0, 4.1 Hz, 1H), 2.64–2.80 (m, 2H), 2.88 (dd, J=17.0, 11.0 Hz, 1H), 3.04 (dd, J=13.0, 6.3 Hz, 1H), 3.34 (dd, J=13.5, 3.2 Hz, 1H), 3.95 (t, J=8.4 Hz, 1H), 4.08–4.12 (m, 1H), 4.5–4.6 (m, 2H), 7.21–7.40 (m, 10H).

MS (ESI): m/z=441.3 (M+NH₄⁺).

PREPARATION 3

Compound 3

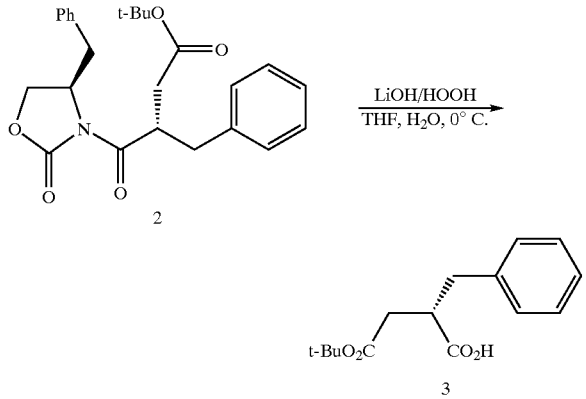

A stirred solution of compound 2 (2.860 g, 6.753 mmol) in 70 mL of 4:1 THF/H₂O was cooled to 0° C. and 30% aq. hydrogen peroxide (2.8 mL, 27.01 mmol) was added dropwise during 5 min. After 5 min, a 1.0M solution of LiOH.H₂O in H₂O (13.51 ml, 13.51 mmol) was added dropwise during 10 min. The reaction was kept at 0° C. for 1.75 hr. and then a 1.5M solution of Na₂SO₃ in H₂O (18.0 ml, 27.01 mmol) was added. The ice bath was removed and the reaction mixture was allowed to warm towards room temperature over 30 min. A solution of 1.0N NaHCO₃ in H₂O was added until the reaction mixture had a pH=9 by pH paper (~5 ml). Most of the THF was removed by rotary evaporation and the residue was partitioned between CH₂Cl₂ and H₂O. The aqueous layer was washed 3×CH₂Cl₂ and then acidified with 2N HCl until pH=3 by pH paper. The aqueous layer was extracted 4×CH₂Cl₂ and the combined organic extracts were dried over Na₂SO₄ and evaporated in vacuo to give an oil. Flash chromatography through 100 g of silica gel (94:6 CH₂Cl₂/MeOH+0.5% HOAc) yielded 1.74 g of the title compound as a white solid.

¹H-NMR (500 Mz, CDCl₃): δ 1.45 (s, 9H), 2.38 (dd, J=16.6, 4.4 Hz, 1H), 2.58 (dd, J=16.6, 8.5 Hz, 1H), 2.80 (dd, J=15.3, 10.3 Hz, 1H), 3.10–3.20 (m, 2H), 7.20–7.40 (m, 5H), 11.99 (bs, 1H).

MS (ESI): m/z=430.2 (M+NH₄⁺).

PREPARATION 4

Compound 4

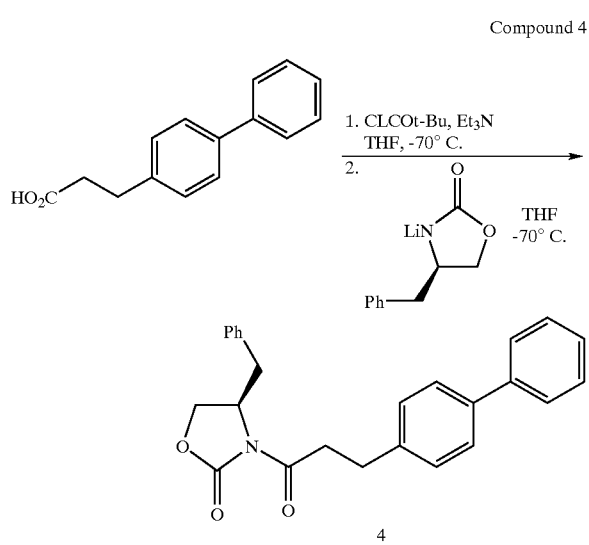

To a stirred solution of 3-(4-biphenyl)-propionic acid (1.805 g, 7.977 mmol) in 40 mL of THF was added Et₃N (1.28 mL, 9.17 mmol) and the solution was cooled to −70° C. Neat pivaloyl chloride (1.0 ml, 8.1 mmol) was added and a thick white suspension resulted. After 15 min, the reaction mixture was warmed by placing in an ice bath and kept at 0° C. for 40 min. The mixture was then re-cooled to −70° C. In a separate flask, a solution of (4R)-benzyl-2-oxazolidinone (1.44 g, 8.13 mmol) in 35 mL of THF was cooled to −70° C. and metalated by the dropwise addition of a 2.5M solution of n-butyllithium in hexanes (3.25 mL, 8.13 mmol). The resulting anion solution was added to the re-cooled suspension via a cannula, rinsing with an additional 3 mL of THF. After 15 min, the reaction mixture was warmed by placing in an ice bath and kept at 0° C. for 30 min. The reaction was hydrolyzed by the addition of sat. aqueous NH₄Cl and most of the THF was removed by rotary evaporation. The residue was partitioned between ethyl acetate and sat. aqueous NH₄Cl and the organic phase was washed with sat. aqueous NaHCO₃, water and brine. The organic layer was dried over Na₂SO₄ and evaporated in vacuo to give a solid. Flash chromatography through 240 g of silica gel (CH₂Cl₂) yielded 2.45 g of the title compound as a white solid.

¹H-NMR (500 Mz, CDCl₃): δ 2.79 (dd, J=13.3, 9.4 Hz, 1H), 3.05–3.15 (m, 2H), 3.25–3.41 (m, 3H), 4.15–4.25 (m, 2H), 4.65–4.75 (m, 1H), 7.15–7.65 (m, 14H).

MS (EI): m/z=385.2 (M⁺).

PREPARATION 5

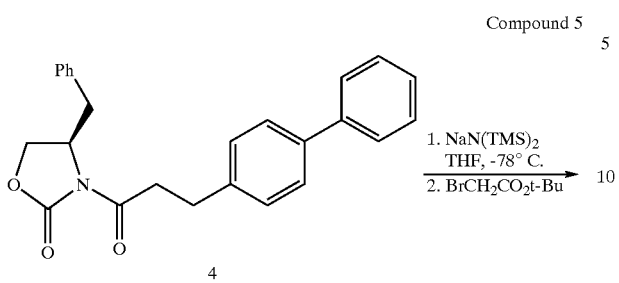

Compound 5

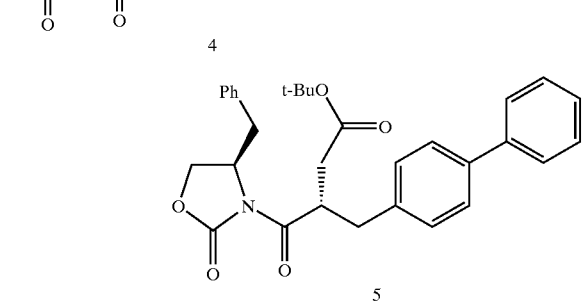

A stirred solution of compound 4 (1.000 g, 2.594 mmol) in 40 mL of THF was cooled to −78° C. and a 1.0M solution of NaN(TMS)$_2$ in THF (2.85 mL, 2.85 mmol) was added dropwise during 5 min. After 30 min, a solution of t-butyl bromoacetate (0.500 mL, 3.37 mmol) in 4 mL of THF was added dropwise during 5 min. The solution was stirred at −78° C. for 1 h and then the reaction was hydrolyzed by the addition of sat. aqueous NH$_4$Cl. The reaction mixture was partitioned between ethyl acetate and sat. aqueous NH$_4$Cl and the organic phase was washed with water and brine. The organic layer was dried over Na$_2$SO$_4$ and evaporated in vacuo to give a solid. Flash chromatography through 150 g of silica gel (65:30:5 hexane/CH$_2$Cl$_2$/EtOAc) yielded 1.12 g of the title compound as a white solid.

$^1$H-NMR (500 Mz, CDCl$_3$): δ 1.43 (s, 9H), 2.45 (dd, J=16.9, 4.1 Hz, 1H), 2.65–2.80 (m, 2H), 2.89 (dd, J=16.9, 10.8 Hz, 1H), 3.07 (dd, J=13.0, 6.1 Hz, 1H), 3.34 (dd, J=13.5, 3.0 Hz, 1H), 3.94 (t, J=8.4 Hz, 1H), 4.08–4.11 (m, 1H), 4.5–4.6 (m, 2H), 7.25–7.60 (m, 14H).

MS (ESI): m/z=517.5 (M+NH$_4{}^+$).

PREPARATION 6

Compound 6

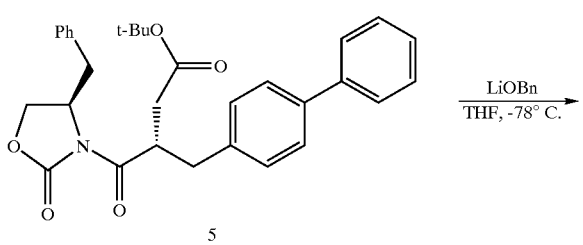

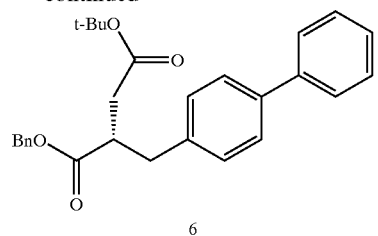

A stirred solution of compound 5 (0.907 g, 1.815 mmol) in 10 mL of THF was cooled to −70° C. and a freshly prepared 0.27 M solution of LiOBn in THF (10 mL, 2.7 mmol) was added dropwise during 10 min. The reaction was allowed to warm gradually to −10° C. during 2 h and was then placed in an ice bath and kept at 0° C. for 50 min. The reaction mixture was partitioned between ethyl acetate and sat. aqueous NH$_4$Cl and the organic phase was washed with water and brine. The organic layer was dried over Na$_2$SO$_4$ and evaporated in vacuo to give an oil. Flash chromatography through 125 g of silica gel (75:20:5 hexane/CH$_2$Cl$_2$/EtOAc) yielded 0.696 g of the title compound as a white solid.

$^1$H-NMR (500 Mz, CDCl$_3$): δ 1.42 (s, 9H), 2.43 (dd, J=16.6, 5.1 Hz, 1H), 2.67 (dd, J=16.6, 9.1 Hz, 1H), 2.85 (dd, J=13.6, 7.9 Hz, 1H), 3.07 (dd, J=13.5, 6.9 Hz, 1H), 3.15–3.25 (m, 1H), 5.09 (d, J=12.4 Hz, 1H), 5.15 (d, J=12.4 Hz, 1H), 7.20–7.65 (m, 14H).

MS (EI): m/z=430.2 (M$^+$).

PREPARATION 7

Compound 7

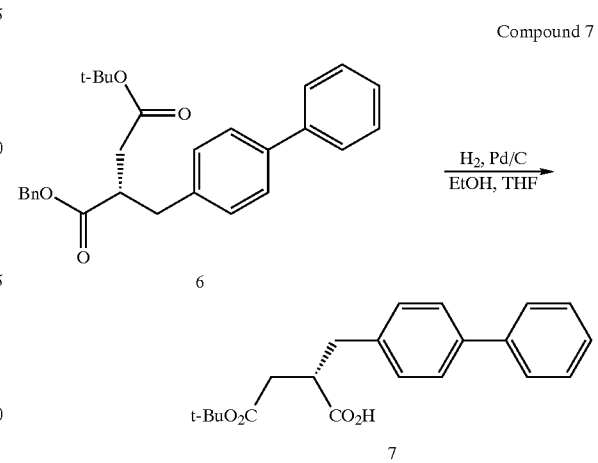

A solution of compound 6 (0.696 g, 1.617 mmol) in 10 mL of EtOH and 5 mL of THF was hydrogenated at atmospheric pressure at room temperature over 70 mg of 10% Pd/C. After 20 h, the mixture was filtered and evaporated to give a solid. Flash chromatography through 50 g of silica gel (5:2:2:1 hexane/CH$_2$Cl$_2$/EtOAc/MeOH+0.05% HOAc) yielded 0.540 g of the title compound as a white solid.

$^1$H-NMR (500 Mz, CDCl$_3$): δ 1.45 (s, 9H), 2.43 (dd, J=16.6, 5.1 Hz, 1H), 2.62 (dd, J=16.8, 8.6 Hz, 1H), 2.84 (dd, J=15.5, 10.4 Hz, 1H), 3.1–3.2 (m, 2H), 7.25–7.60 (m, 9H).

MS (EI): m/z=340.2 (M$^+$).

PREPARATION 8

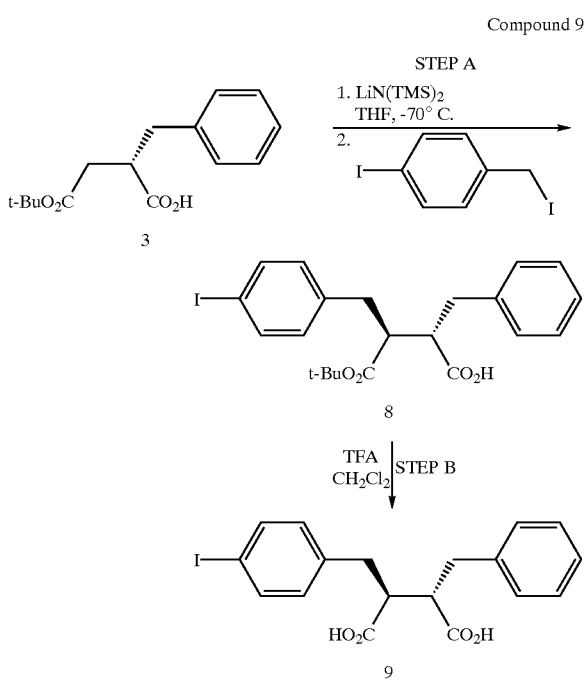

Compound 9

Step A

A stirred solution of compound 3 from Preparation 3 (1.011 g, 3.825 mmol) in 15.5 mL of THF was cooled to −70° C. and a 1.0M solution of LiN(TMS)$_2$ in hexane (8.42 mL, 8.42 mmol) was added dropwise. After 1 h, a freshly prepared 1.14M solution of p-iodobenzyl iodide in THF (6.0 mL, 6.84 mmol) was added dropwise. The solution was stirred at −70° C. for 30 min and was then allowed to warm gradually to 10° C. during 90 min. The reaction was hydrolyzed by the addition of sat. aqueous NH$_4$Cl and most of the THF was removed by rotary evaporation. The residue was partitioned between ethyl acetate and sat. aqueous NH$_4$Cl and the organic phase was washed with water and brine. The organic layer was dried over Na$_2$SO$_4$ and evaporated in vacuo to give a solid. Flash chromatography through 450 g of silica gel (98:2 CH$_2$Cl$_2$/MeOH+0.1% HOAc) yielded 1.78 g of compound 8 as a ~6:1 mixture of (S,S:R,S) diastereomers (major isomer depicted).

$^1$H-NMR (500 Mz, CDCl$_3$): δ 1.32 (s, 9H), 2.74–3.05 (m, 6H), 6.89 (d, J=8.2 Hz, 2H), 7.12–7.28 (m, 5H), 7.56 (d, J=8.4 Hz, 2H).

MS (EI): m/z=480.4 (M$^+$).

Step B

To a solution of compound 8 (182.0 mg, 0.3789 mmol) in 0.6 mL of CH$_2$Cl$_2$ was added neat trifluoroacetic acid (0.2 mL). The solution was stirred at room temperature for 4 h, and was then evaporated in vacuo to give an oil. Separation by reverse phase medium pressure chromatography on RP-18 (40:60 MeCN/0.1% aqueous TFA) gave after lyophilization 103.7 mg of the title compound as a white solid.

$^1$H-NMR (500 Mz, CD$_3$OD): 2.84–2.91 (m, 2H), 2.96–3.06 (m, 4H), 6.89 (d, J=8.2 Hz, 2H), 7.11–7.25 (m, 5H), 7.55 (d, J=8.2 Hz, 2H).

MS (EI): m/z=424.2 (M$^+$).

PREPARATION 9

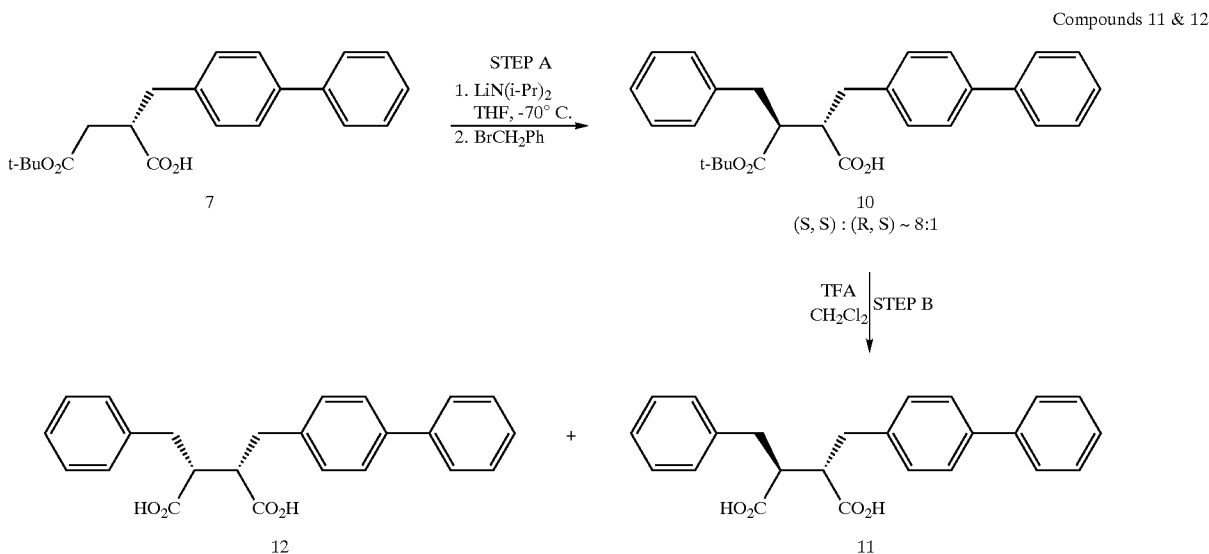

Compounds 11 & 12

Step A

A stirred solution of compound 7 (26.2 mg, 0.0770 mmol) in 0.7 mL of THF was cooled to −70° C. and a freshly prepared 1.0M solution of LiN(i-Pr)$_2$ in THF (0.17 mL, 0.17 mmol) was added dropwise. After 1 h, neat benzyl bromide (0.015 mL, 0.12 mmol) was added dropwise. The solution was stirred at −70° C. for 20 min and was then allowed to warm gradually to 10° C. during 90 min. The reaction was hydrolyzed by the addition of sat. aqueous NH$_4$Cl. The reaction mixture was partitioned between ethyl acetate and sat. aqueous NH$_4$Cl and the organic phase was washed with water and brine. The organic layer was dried over Na$_2$SO$_4$ and evaporated in vacuo to give an oil. Purification by preparative layer chromatography on silica gel (93:7 CH$_2$Cl$_2$/MeOH+0.1% HOAc) yielded 28 mg of compound 10 as an ~8:1 mixture of (S,S:R,S) diastereomers (major isomer depicted).

$^1$H-NMR (500 Mz, CDCl$_3$): 1.33 (s, 9H, isomer B, minor), 1.37 (s, 9H, isomer A, major), 2.85–3.20 (m, 6H, isomers A & B), 7.10–7.65 (m, 14H, isomers A & B).

MS (EI): m/z=430.3 (M$^+$).

Step B

To a solution of compound 10 from Step A (10.3 mg, 0.0239 mmol) in 0.3 mL of CH$_2$Cl$_2$ was added neat trifluoroacetic acid (0.1 mL). The solution was stirred at room temperature for 4 h, and was then evaporated in vacuo to give an oil. Separation by reverse phase medium pressure liquid chromatography on RP-18 (45:55 MeCN/0.1% aqueous TFA) gave after lyophilization 5.0 mg of compound 11 and 0.7 mg of compound 12 as white solids.

Compound 11

$^1$H-NMR (500 Mz, CD$_3$OD): 2.90–2.97 (m, 2H), 3.0–3.1 (m, 4H), 7.14 (d, J=7.1 Hz, 3H), 7.15–7.25 (m, 5H), 7.41 (t, J=7.7 Hz, 2H), 7.52 (d, J=8.0 Hz, 2H), 7.58 (d, J=7.8 Hz, 2H).

MS (EI): m/z=374.2 (M$^+$).

Compound 12

$^1$H-NMR (500 Mz, CD$_3$OD): 2.85–3.00 (m, 6H), 7.19 (d, J=6.8 Hz, 3H), 7.24–7.32 (m, 5H), 7.30 (t, J=7.4 Hz, 1H), 7.41 (dd, J=7.5, 8.0 Hz, 2H), 7.49 (d, J=8.0 Hz, 2H), 7.58 (d, J=7.6 Hz, 2H).

MS (EI): m/z=374.2 (M$^+$).

PREPARATION 10

Compound 10

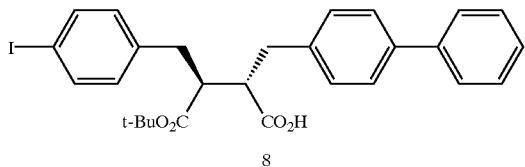
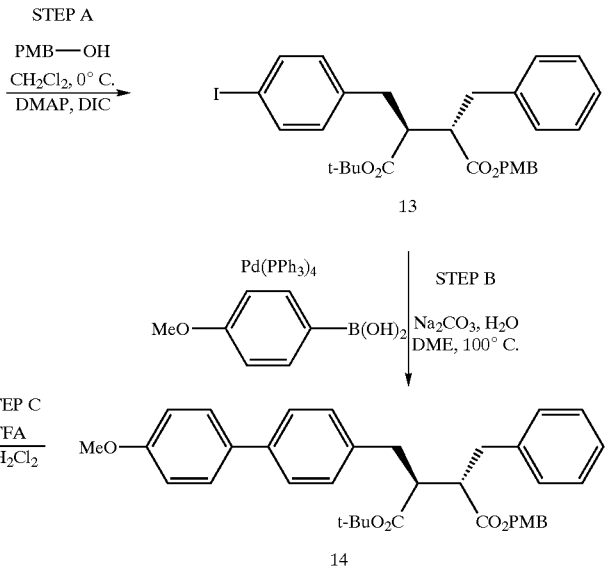
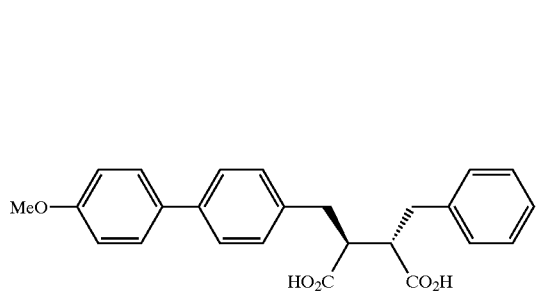

Step A

A stirred solution of compound 8 (830.1 mg, 1.728 mmol) and p-methoxybenzyl alcohol (0.54 ml, 4.33 mmol) in 14 mL of CH$_2$Cl$_2$ was cooled to 0° C., and a 1.0M solution of N,N-dimethylaminopyridine in CH$_2$Cl$_2$ (0.259 ml, 0.259 mmol) was added, followed by neat 1,3-diisopropylcarbodiimide (0.541 ml, 3.46 mmol). After 1 hr, the cooling bath was removed. The reaction mixture was stirred an additional 180 min, and was then hydrolyzed by the addition of sat. aqueous NH$_4$Cl. The reaction mixture was partitioned between ethyl acetate and sat. aqueoues NH$_4$Cl and the organic phase was washed with water and brine. The organic layer was dried over Na$_2$SO$_4$ and evaporated in vacuo to give a semi-solid. This crude material was triturated with 10 ml CH$_2$Cl$_2$ and filtered through a sintered-glass funnel. Evaporation of the filtrate in vacuo gave an oil. Flash chromatography through 160 g of silica gel (73:20:7 hexane/CH$_2$Cl$_2$/EtOAc) yielded 921.6 mg of compound 13 as a white solid.

$^1$H-NMR (500 Mz, CDCl$_3$): 1.37 (s, 9H), 2.8–3.1 (m, 6H), 3.83 (s, 3H), 4.98 (dd, J=43.5, 11.9 Hz, 2H), 6.76 (d, J=8.0 Hz, 2H), 6.86 (d, J=8.4 Hz, 2H), 7.07 (d, J=6.6 Hz, 2H), 7.16–7.27 (m, 5H), 7.53 (d, J=8.1 Hz, 2H).

MS (ESI: m/z=623.2 (M+Na$^+$).

Step B

To a stirred solution of compound 13 (76.6 mg, 0.1276 mmol) and tetrakis(triphenylphosphine)palladium(0) (7.4 mg, 0.0064 mmol) in 1.1 ml DME was added a solution of 4-methoxybenzeneboronic acid (29.1 mg, 0.192 mmol) in 0.2 ml DME. After 10 min, a 2.0M solution of Na$_2$CO$_3$ in H₂O (0.130 ml, 0.260 mmol) was added and the reaction mixture was heated to 100° C. for 3.5 hr. The reaction mixture was allowed to cool to RT and then hydrolyzed by the addition of sat. aqueous NH₄Cl. The reaction mixture was partitioned between ethyl acetate and sat. aqueous NH₄Cl and the organic phase was washed with sat. aqueous NaS₂O₃, water, and brine. The organic layer was dried over Na₂SO₄ and evaporated in vacuo to give an oil. Flash chromatography through 18 g of silica gel (73:20:7 hexane/CH₂Cl₂/EtOAc) yielded 37.1 mg of compound 14 as a white solid.

¹H-NMR (500 Mz, CDCl₃): 1.36 (s, 9H), 2.90–3.07 (m, 6H), 3.82 (s, 3H), 3.87 (s, 3H), 4.98 (dd, J=34.8, 11.9 Hz, 2H), 6.86 (d, J=8.7 Hz, 2H), 6.99 (d, J=8.7 Hz, 2H), 7.09 (d, J=7.8 Hz, 4H), 7.16–7.26 (m, 5H), 7.42 (d, J=8.0 Hz, 2H), 7.52 (d, J=8.5 Hz, 2H).

MS (ESI): m/z=603.3 (M+Na⁺).

Step C

To a solution of compound 14 (37.1 mg, 0.064 mmol) in 0.6 mL of CH₂Cl₂ was added neat trifluoroacetic acid (0.2 mL). The solution was stirred at room temperature for 4 h, and was then evaporated in vacuo to give an oil. Separation by reverse phase medium pressure chromatography on RP-18 (45:55 MeCN/0.1% aqueous TFA) gave after lyophilization 9.3 mg of the title compound as a white solid.

¹H-NMR (500 Mz, CD₃OD): 2.89–2.96 (m, 2H), 3.01–3.07 (m, 4H), 3.81 (s, 3H), 6.97 (d, J=8.9 Hz, 2H), 7.11–7.25 (m, 7H), 7.43 (d, J=8.2 Hz, 2H), 7.51 (d, J=8.7 Hz, 2H).

MS (ESI): m/z=427.1 (M+Na⁺).

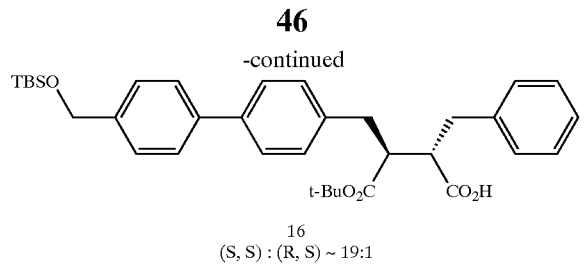

16
(S, S) : (R, S) ~ 19:1

A stirred solution of compound 3 (0.253 g, 0.957 mmol) in 7 mL of THF was cooled to −78° C. and a 1.0M solution of LiN(TMS)₂ in hexanes (2.2 mL, 2.2 mmol) was added dropwise during 5 min. After 65 min, a solution of 4-(iodomethyl)-4'-(t-butyldimethylsilyloxymethyl)biphenyl (0.630 g, 1.44 mmol) in 1 mL of THF was added dropwise during 5 min. The solution was stirred at −78° C. for 35 min and was then allowed to warm gradually to −20° C. during 2 h, at which point the reaction was judged to be complete by HPLC analysis. The reaction was hydrolyzed by the addition of sat. aqueous NH₄Cl. The reaction mixture was then partitioned between ethyl acetate and sat. aqueous NH₄Cl and the organic phase was washed with water and brine. The organic layer was dried over Na₂SO₄ and evaporated in vacuo to give a solid. Flash chromatography on silica gel (95:3:2 CH₂Cl₂/EtOAc/MeOH) yielded 0.479 g of compound 16 as an ~19:1 mixture of (S,S:R,S) diastereomers (major isomer depicted).

¹H-NMR (500 Mz, CDCl₃): δ 0.15 (s, 6H), 0.99 (s, 9H), 1.39 (s, 9H), 2.85–2.95 (m, 1H), 2.95–3.20 (m, 5H),4.81 (s, 2H), 7.13 (d, J=6.9 Hz, 2H), 7.17 (d, J=8.1 Hz, 2H), 7.20–7.35 (m, 3H), 7.42 (d, J=8.0 Hz, 2H), 7.49 (d, J=8.0 Hz, 2H), 7.57 (d, J=8.0 Hz, 2H).

MS (EI): m/z=574.3 (M⁺).

STEP B:

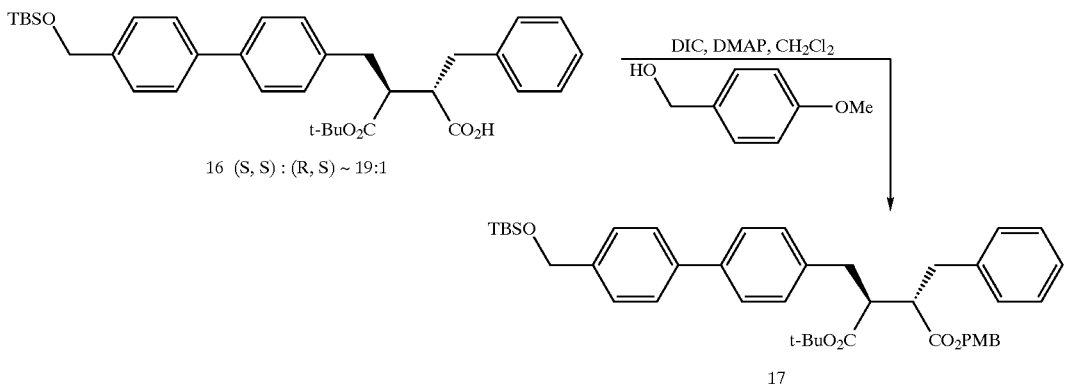

17

EXAMPLE 1

STEP A:

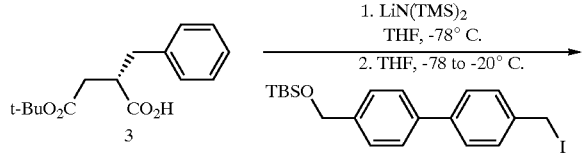

A stirred solution of compound 16 (0.479 g, 0.835 mmol) and p-methoxybenzyl alcohol (0.260 mL, 2.08 mmol) in 7.5 mL of CH₂Cl₂ was cooled to 0° C. and a 1.0 M solution of N,N-dimethylaminopyridine in CH₂Cl₂ (0.125 mL, 0.125 mmol) was added followed by neat 1,3-diisopropylcarbodiimide (0.260 mL, 1.66 mmol). After 40 min, the cooling bath was removed. The reaction mixture was stirred for an additional 140 min, and was then hydrolyzed by the addition of sat. aqueous NH₄Cl. The reaction mixture was partitioned between ethyl acetate and sat. aqueous NH₄Cl and the organic phase was washed with water and brine. The organic layer was dried over Na₂SO₄ and evaporated in vacuo to give a semi-solid. Flash chromatography on silica gel (75:21.5:3.5 to 75:20:5 hexane/

CH$_2$Cl$_2$/EtOAc) yielded 0.486 g of compound 17 as an oil. The diastereomeric ratio was >100:1 (S,S): (R,S).

$^1$H-NMR (500 Mz, CDCl$_3$): δ 0.16 (s, 6H), 0.99 (s, 9H), 1.37 (s, 9H), 2.90–3.10 (m, 6H), 3.83 (s, 3H), 4.81 (s, 2H), 4.96 (d, J=11.9 Hz, 1H), 5.04 (d, J=11.9 Hz, 1H), 6.87 (d, J=8.2 Hz, 2H), 7.07–7.15 (m, 4H), 7.18–7.28 (m, 5H), 7.41 (d, J=7.8 Hz, 2H), 7.47 (d, J=7.7 Hz, 2H), 7.56 (d, J=8.0 Hz, 2H).

MS (ESI): m/z=712.6 (M+NH$_4^+$).

water and brine. The organic layer was dried over Na$_2$SO$_4$ and evaporated in vacuo to give an oil. Flash chromatography on silica gel (4:3:3 hexane/CH$_2$Cl$_2$/EtOAc) yielded 0.389 g of compound 18 as an oil.

$^1$H-NMR (500 Mz, CDCl$_3$): δ 1.37 (s, 9H), 2.90–3.10 (m, 6H), 3.82 (s, 3H), 4.77 (s, 2H), 4.96 (d, J=11.9 Hz, 1H), 5.03

STEP C:

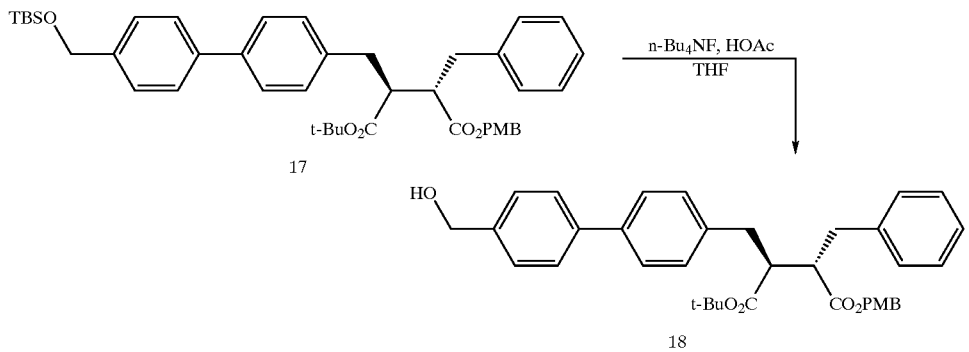

(d, J=11.9 Hz, 1H), 6.87 (d, J=8.5 Hz, 2H), 7.05–7.30 (m, 9H), 7.4–7.5 (m, 4H), 7.59 (d, J=8.0 Hz, 2H).

MS (ESI): m/z=598.5 (M+NH$_4^+$).

STEP D:

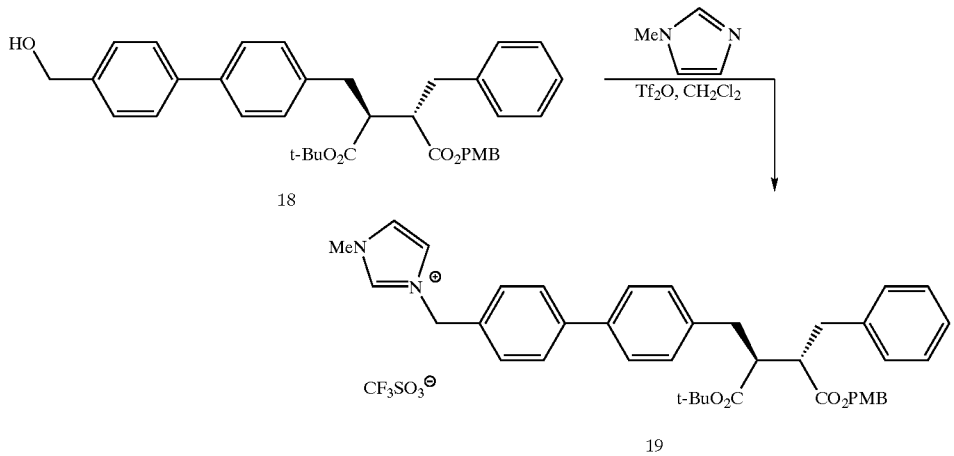

A stirred solution of compound 17 (0.482 g, 0.694 mmol) in 4.5 mL of THF was cooled to 0° C. and neat acetic acid (0.120 mL, 2.1 mmol) was added followed by a 1.0 M solution of tetrabutylammonium fluoride in THF (2.1 mL, 2.1 mmol). After 50 min, the cooling bath was removed. After stirring at room temperature for 22 h, the reaction was judged to be complete by TLC on silica gel. The reaction mixture was partitioned between ethyl acetate and sat. aqueous NH$_4$Cl and the organic phase was washed with A stirred solution of compound 18 (20.0 mg, 0.0344 mmol) in 0.35 mL of CH$_2$Cl$_2$ was cooled to −70° C. and neat 1-methylimidazole (0.0090 mL, 0.11 mmol) was added followed by trifluoromethanesulfonic anhydride (0.0090 mL, 0.053 mmol). The temperature was allowed to gradually rise and after 45 min was −15° C. TLC on silica gel showed some remaining starting material, so additional 1-methylimidazole (0.0050 mL, 0.063 mmol) was added. After 25 min more, the temperature was 5° C. and TLC showed no starting material. The reaction mixture was partitioned between ethyl acetate and water and the organic phase was washed once with water. The organic layer was dried over $Na_2SO_4$ and evaporated in vacuo to give an oil. Preparative layer chromatography on silica gel (1:1 MeCN/$CH_2Cl_2$) yielded 19.0 mg of compound 19 as an oil.

$^1$H-NMR (500 Mz, $CDCl_3$): δ 1.36 (s, 9H), 2.88–3.08 (m, 6H), 3.81 (s, 3H), 3.94 (s, 3H), 4.95 (d, J=12 Hz, 1H), 5.02 (d, J=12 Hz, 1H), 5.39 (s, 2H), 6.86 (d, J=8.6 Hz, 2H), 7.05–7.35 (m, 11H), 7.43 (d, J=8.3 Hz, 2H), 7.48 (d, J=8.0 Hz, 2H), 7.60 (d, J=8.3 Hz, 2H), 9.23 (s, 1H).

MS (ESI): m/z=645.5 (M$^+$).

$^1$H-NMR (500 Mz, $CD_3OD$): δ 2.88–2.98 (m, 2H), 3.0–3.1 (m, 4H), 3.93 (s, 3H), 5.44 (s, 2H), 7.10–7.25 (m, 7H), 7.45–7.55 (m, 4H), 7.59 (s, 1H), 7.65 (s, 1H), 7.68 (d, J=8.2 Hz, 2H), 8.99 (s, 1H).

MS (ESI): m/z=469.4 (M$^+$).

STEP E:

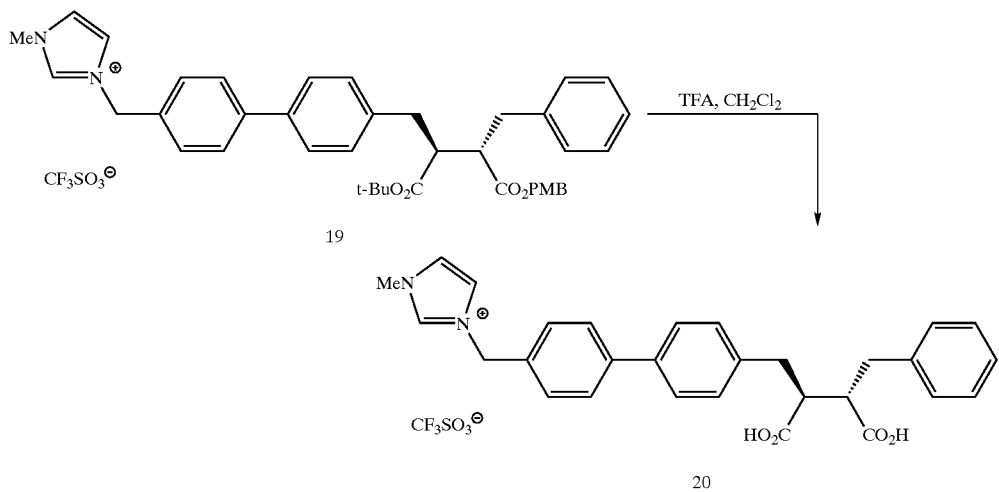

EXAMPLE 2

STEP A:

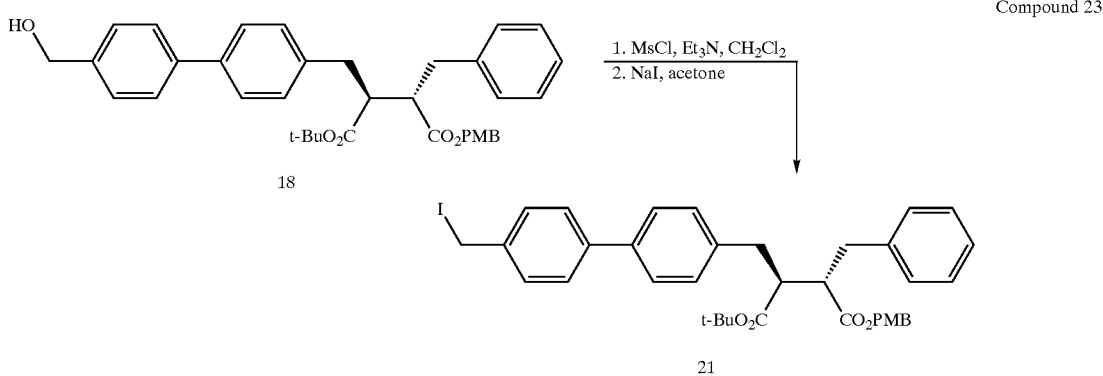

To a solution of compound 19 (18.5 mg, 0.0233 mmol) in 0.3 mL of $CH_2Cl_2$ was added neat trifluoroacetic acid (0.1 mL). The solution was stirred at room temperature for 110 min, and was then evaporated in vacuo to give a solid. Purification by reverse phase medium pressure liquid chromatography on RP-18 (40:60 MeCN/0.1% aqueous TFA) gave after lyophilization 10.4 mg of compound 20 as a white solid.

A stirred solution of compound 18 (0.262 g, 0.451 mmol) in 4.5 mL of $CH_2Cl_2$ was cooled to −60° C. and triethylamine (0.107 mL, 0.768 mmol) was added followed by neat methanesulfonyl chloride (0.0490 mL, 0.633 mmol). The temperature was allowed to gradually rise and after 45 min was −25° C. The reaction was hydrolyzed by the addition of sat. aqueous $NH_4Cl$. The reaction mixture was partitioned between ethyl acetate and sat. aqueous $NH_4Cl$ and the organic phase was washed with water and brine. The organic layer was dried over Na$_2$SO$_4$ and evaporated in vacuo to give a solid.

The crude mesylate was dissolved in acetone and cooled to 0° C. Solid sodium iodide was added (0.135 g, 0.901 mmol) and the mixture was stirred in the dark. After 30 min, the cooling bath was removed. After stirring for 2 h more, the reaction mixture was partitioned between ethyl acetate and water. The organic phase was washed with 5% aqueous Na$_2$S$_2$O$_3$, water and brine. The organic layer was dried over Na$_2$SO$_4$ and evaporated in vacuo to give 313 mg of compound 21 as a solid.

$^1$H-NMR (500 Mz, CDCl$_3$): δ 1.36 (s, 9H), 2.9–3.1 (m, 6H), 3.82 (s, 3H), 4.54 (s, 2H), 4.96 (d, J=11.9 Hz, 1H), 5.03 (d, J=11.9 Hz, 1H), 6.87 (d, J=8.5 Hz, 2H), 7.06–7.14 (m, 4H), 7.17–7.28 (m, 5H), 7.42–7.50 (m, 4H), 7.51 (d, J=8.2 Hz, 2H).

MS (ESI): m/z=708.1 (M+NH$_4^+$).

To a stirred solution of compound 21 (0.0212 g, 0.0307 mmol) and 1-(aminocarbonylmethyl-4-aza-1-azoniabicyclo (2.2.2)octane trifluoromethanesulfonate (0.011 g, 0.034 mmol) in 0.35 mL of acetonitrile and 0.1 mL of THF was added a solution of silver trifluoromethanesulfonate in acetonitrile (0.845 M, 0.036 mL, 0.030 mmol). A precipitate formed immediately. The mixture was stirred in the dark for 55 min and was then filtered and evaporated in vacuo to give 37 mg of compound 22 as a solid.

$^1$H-NMR (500 Mz, d$_6$-acetone): δ 1.32 (s, 9H), 2.9–3.1 (m, 6H), 3.80 (s, 3H), 4.38–4.48 (m, 6H), 4.50–4.60 (m, 6H), 4.65 (s, 2H), 4.93 (d, J=12 Hz, 1H), 5.02 (d, J=12 Hz, 1H), 5.14 (s, 2H), 6.90 (d, J=8.7 Hz, 2H), 7.16 (d, J=6.9 Hz, 2H), 7.2–7.3 (m, 8H), 7.63 (d, J=8.0 Hz, 2H), 7.69 (bs, 1H), 7.80 (d, J=8.2 Hz, 2H), 7.86 (d, J=8.2 Hz, 2H).

MS (ESI): m/z=732.5 (M$^{+2}$−H$^+$).

STEP B:

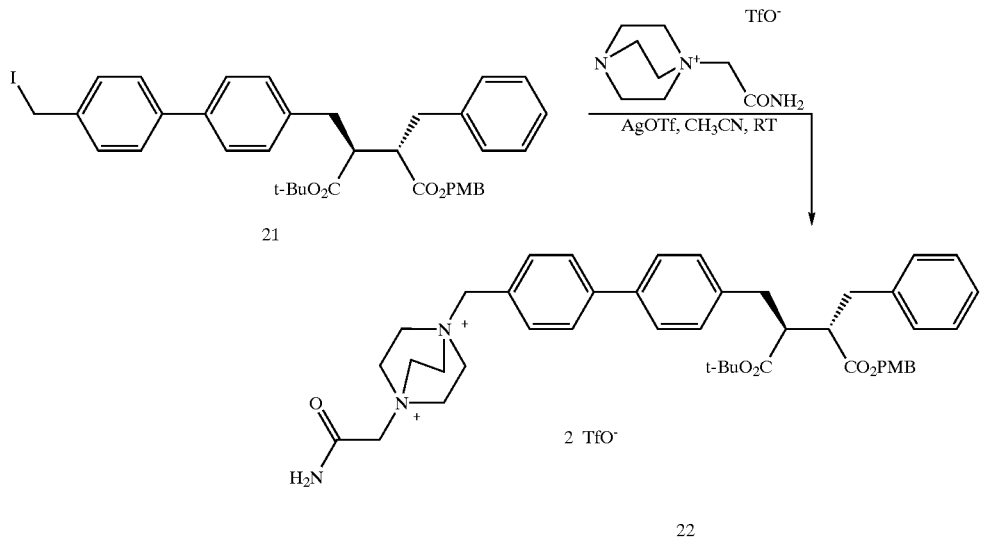

STEP C:

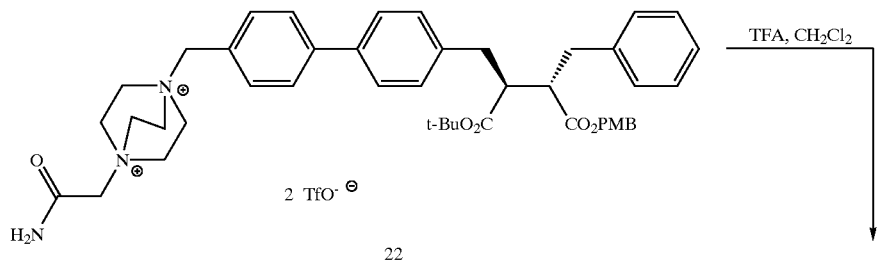

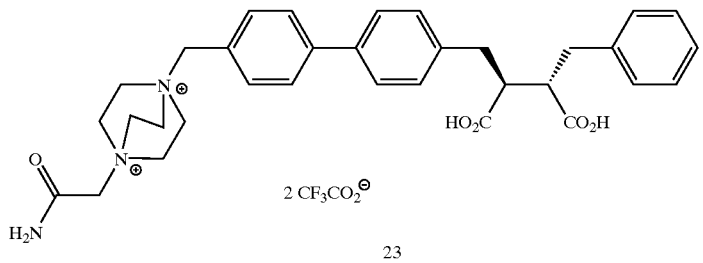

A solution of compound 22 (37 mg) in 0.3 mL of $CH_2Cl_2$ and 0.1 mL of trifluoroacetic acid was stirred at room temperature for 150 min, and was then evaporated in vacuo to give a film. Purification by reverse phase medium pressure liquid chromatography on RP-18 (25:75 MeCN/0.1% aqueous TFA) gave after lyophilization 21.8 mg of compound 23 as a white solid.

$^1$H-NMR (500 Mz, $CD_3OD$): δ 2.88–2.98 (m, 2H), 3.00–3.15 (m, 4H), 3.18–4.08 (m, 6H), 4.2–4.3 (m, 6H), 4.36 (s, 2H), 4.82 (s, 2H), 7.14 (d, J=7.1 Hz, 2H), 7.15–7.30 (m, 5H), 7.56 (d, J=8.0 Hz, 2H), 7.63 (d, J=8.2 Hz, 2H), 7.82 (d, J=8.3 Hz, 2H).

MS (ESI): m/z=556.4 ($M^{+2}-H^+$).

EXAMPLE 3

To a stirred solution of compound 21 (0.194 g, 0.281 mmol) in 0.75 mL of THF was added a solution of 1-(1-azidoprop-3-yl)-4-aza-1-azoniabicyclo(2.2.2)octane trifluoromethanesulfonate (0.107 g, 0.310 mmol) in 2.25 mL of acetonitrile. To the resulting solution was added a solution of silver trifluoromethanesulfonate in acetonitrile (0.845 M, 0.332 mL, 0.281 mmol). A precipitate formed immediately. The mixture was stirred in the dark for 45 min and was then filtered and evaporated in vacuo to give 312 mg of compound 24 as a solid.

$^1$H-NMR (500 Mz, d6-acetone): δ 1.32 (s, 9H), 2.25–2.35 (m, 2H), 2.90–3.15 (m, 6H), 3.55–3.65 (m, 2H), 3.80 (s, 3H), 3.93–4.00 (m, 2H), 4.37 (s, 12H), 4.93 (d, J=12 Hz, 1H), 5.02 (d, J=12 Hz, 1H), 5.14 (s, 2H), 6.90 (d, J=8.4 Hz, 2H), 7.16 (d, J=6.6 Hz, 2H), 7.2–7.3 (m, 7H), 7.63 (d, J=8.2 Hz, 2H), 7.80 (d, J=8.5 Hz, 2H), 7.85 (d, J=8.2 Hz, 2H).

MS (ESI): m/z=872.1 ($M^{+2}+CF_3CO_2-$).

STEP A:

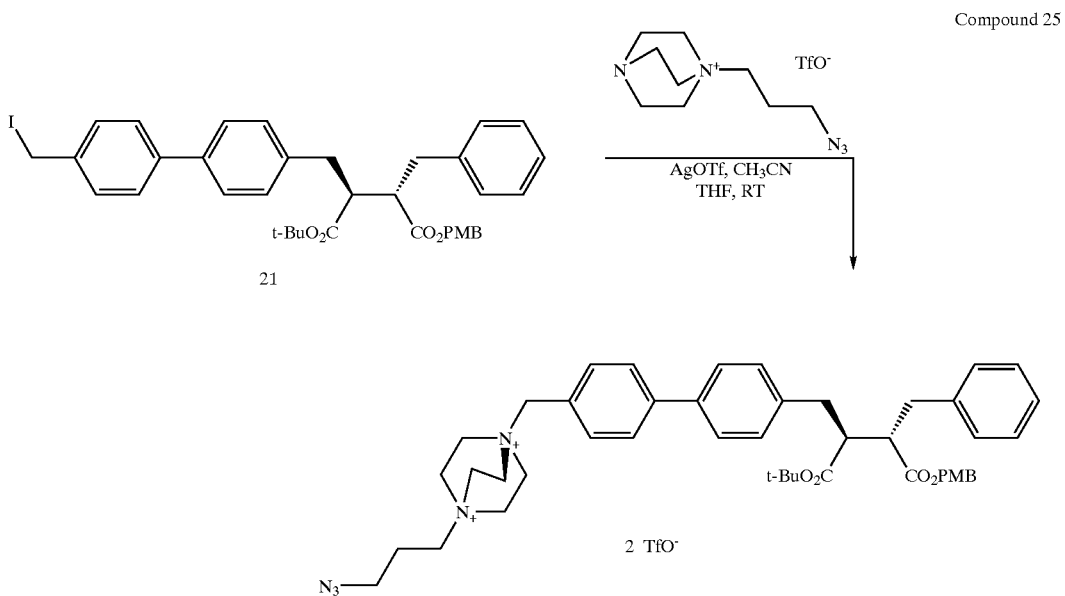

STEP B:

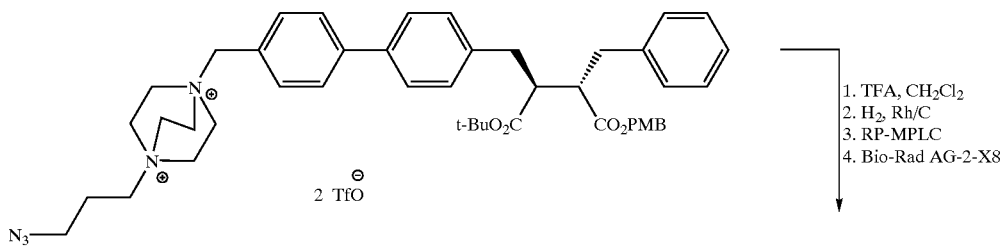

A solution of compound 24 (312 mg) in 2.1 mL of $CH_2Cl_2$ and 0.7 mL of trifluoroacetic acid was stirred at room temperature for 125 min, and was then evaporated in vacuo. The resulting dry film was dissolved in 3 mL of THF, 1 mL of MeOH and 1 mL of water and hydrogenated at atmospheric pressure over 55 mg of 5% rhodium on carbon. After 3 h, the mixture was filtered through a pad of Celite®. The tan filtrate was concentrated by rotary evaporation until it became hazy, and was then frozen and lyophilized to give a brown solid. Purification by reverse phase medium pressure liquid chromatography on RP-18 (20:80 MeCN/0.1% aqueous TFA) gave after lyophilization 164 mg of a white solid. A portion of this solid (151.4 mg) was dissolved in 2 mL of methanol and eluted with methanol through a 12 g column of Bio-Rad® AG-2-X8 chloride form resin (~3 meq/g). Evaporation of the collected fractions gave a colorless oil which was lyophilized from water/MeCN to give 109 mg of compound 25 as a white solid.

$^1$H-NMR (500 Mz, $CD_3OD$): δ 2.18–2.30 (m, 2H), 2.9–3.0 (m, 2H), 3.00–3.15 (m, 6H), 3.7–3.8 (m, 2H), 4.08 (s, 12H), 4.89 (s, 2H), 7.14 (d, J=7.0 Hz, 2H), 7.15–7.30 (m, 5H), 7.56 (d, J=8.0 Hz, 2H), 7.67 (d, J=8.0 Hz, 2H), 7.82 (d, J=8.0 Hz, 2H).

MS (ESI): m/z=556.4 ($M^{+3}$–2$H^+$).

EXAMPLE 4

STEP A:

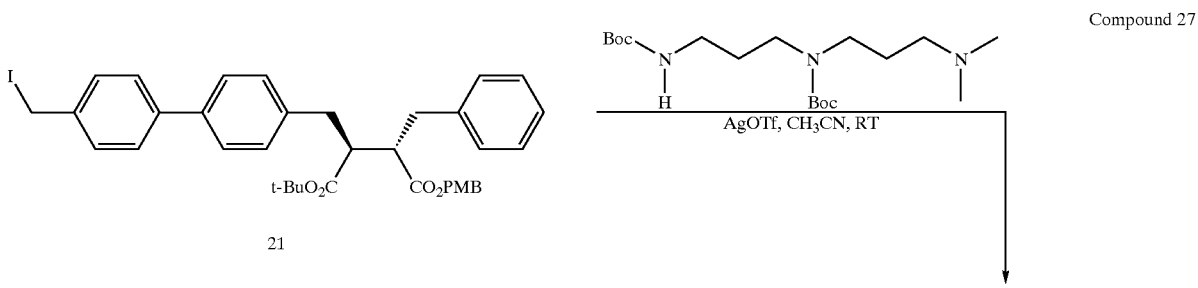

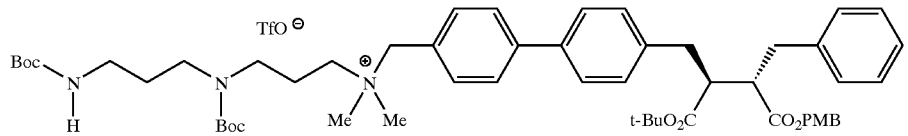

26

To a stirred solution of compound 21 (41.2 mg, 0.0597 mmol) and [3-(dimethylamino)propyl][3-[(1,1-dimethylethoxy)carbonyl amino]propyl]carbamic acid, 1,1-dimethylethyl ester (24.7 mg, 0.0687 mmol) in 1.2 mL of acetonitrile was added a solution of silver trifluoromethane-sulfonate in acetonitrile (0.845 M, 0.066 mL, 0.0564 mmol). A precipitate formed immediately. The mixture was stirred in the dark for 85 min and was then filtered and evaporated in vacuo to give 66.7 mg of compound 26 as a solid.

$^1$H-NMR (500 Mz, d$_6$-acetone): δ 1.33 (s, 9H), 1.40 (s, 9H), 1.45 (s, 9H), 1.74 (bs, 2H), 2.37 (bs, 2H), 2.9–3.2 (m, 8H), 3.26–3.33 (m, 2H), 3.35 (s, 6H), 3.42 (bs, 2H), 3.61 (bs, 2H), 3.80 (s, 3H), 4.85 (s, 2H), 4.97 (dd, J=43.5, 11.9 Hz, 2H), 5.99 (bs, 1H), 6.91 (d, J=8.0 Hz, 2H), 7.16 (d, J=7.3 Hz, 2H), 7.19–7.30 (m, 7H), 7.63 (d, J=7.5 Hz, 2H), 7.8 (dd, J=37.1, 7.9 Hz, 4H).

MS (ESI): m/z=922.5 (M$^+$).

To a solution of compound 26 (66.7 mg) in 0.6 mL of CH$_2$Cl$_2$ was added neat trifluoroacetic acid (0.2 mL). The solution was stirred at room temperature for 5.5 h, and was then evaporated in vacuo to give an oil. Purification by reverse phase medium pressure chromatography on RP-18 (30:70 MeCN/0.1% aqueous TFA) gave after lyophilization 36 mg of a white solid. A portion of this solid (31.5 mg) was dissolved in 2 mL of methanol and eluted with methanol through a 3 g column of Bio-Rad® AG-2-X8 chloride form resin (~3 meq/g). Evaporation of the collected fractions gave a colorless oil which was lyophilized from water/MeCN to give 22.2 mg of compound 27 as a white solid.

$^1$H-NMR (500 Mz, CD$_3$OD): δ 2.07–2.16 (m, 2H), 2.30–2.40 (m, 2H), 2.90–2.97 (m, 2H), 3.03–3.22 (m, 16H), 3.43–3.50 (m, 2H), 4.60 (s, 2H), 7.12–7.28 (m, 7H), 7.56 (d, J=8.2 Hz, 2H), 7.63 (d, J=8.2 Hz, 2H), 7.78 (d, J=8.2 Hz, 2H).

MS (ESI): m/z=546.4 (M$^{+3}$–2H$^+$).

EXAMPLES 5–29

Employing the procedures described herein, additional compounds of the present invention were prepared. These are described in Tables 3–7, which additionally include characterizing data.

STEP B:

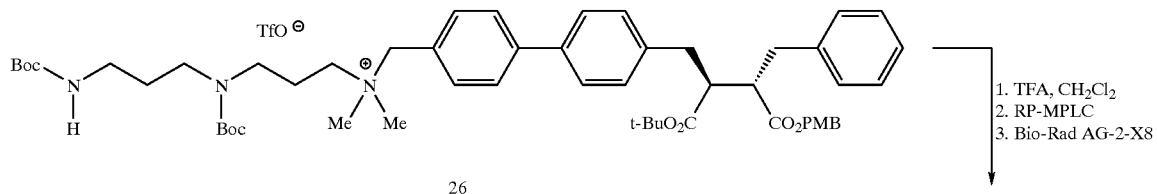

26

1. TFA, CH$_2$Cl$_2$
2. RP-MPLC
3. Bio-Rad AG-2-X8

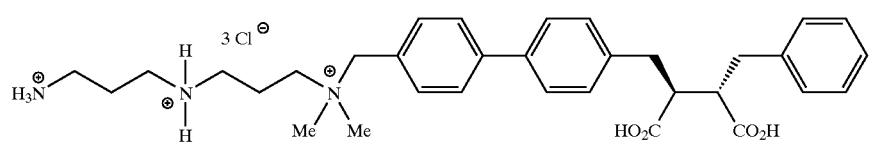

27

TABLE 3

[Structure: Q⊕ — CH2 — (4,4'-biphenyl) — CH2 — CH(CO2H) — CH(CO2H) — CH2 — phenyl; Y⊖]

| Example No. | Q⊕ | Y⊖ | m/z |
|---|---|---|---|
| 5 | H3N⊕—CH2CH2—N⊕(DABCO)N⊕— | 3 Cl⊖ | 542.5 (M+3 − 2H+); ESI |
| 6 | H3N⊕—CH2CH2—N⊕(Me)(Me)—CH2CH2—N⊕(Me)(Me)— | 3 Cl⊖ | 660.4 (M+3 − H+ + CF3CO2−); ESI |
| 7 | (H3N⊕—CH2CH2CH2—)2N⊕(Me)— | 3 Cl⊖ | 532.3 (M+3 − 2H+); ESI |
| 8 | (H3N⊕—CH2CH2CH2—)2N⊕—CH2CH2CH2—N⊕(DABCO)N⊕— | 4 Cl⊖ | 613.4 (M+4 − 3H+); ESI |
| 9 | Me—N⊕(DABCO)N⊕—CH2CH2CH2—N⊕(DABCO)N⊕— | 4 Cl⊖ | |
| 10 | (3,4-diHO-C6H3)—C(=O)—CH2—N⊕(DABCO)N⊕— | 3 Cl⊖ | 649.5 (M+2 − H+); ESI |
| 11 | Me3N⊕—CH2CH2CH2—N⊕(DABCO)N⊕— | 3 Cl⊖ | 712.3 (M+3 − H+ + CF3CO2-); ESI |
| 12 | N⊕(DABCO)N—CH2CH2CH2—N⊕(DABCO)N⊕— | 3 Cl⊖ | 765.5 (M+3 − H+ + CF3CO2−); ESI |
| 13 | H3N⊕—CH2CH2CH2—NH—C(=O)—CH2—N⊕(DABCO)N⊕— | 3 Cl⊖ | 599.3 (M+3 − 2H+); ESI |

TABLE 3-continued

[Structure: biphenyl compound with Q⊕ CH2- group and Y⊖, with HO2C and CO2H substituents on chain bearing benzyl group]

| Example No. | Q⊕ | Y⊖ | m/z |
|---|---|---|---|
| 14 | [triazabicyclic-N⊕-(CH2)n-N⊕-triazabicyclic structure] | 3 Cl⊖ | 793.5 (M$^{+3}$ − H$^+$ + CF$_3$CO$_2^-$); ESI |

TABLE 4

[Structure: similar compound with biphenyl on right side]

| Example No. | Q⊕ | Y⊖ | m/z |
|---|---|---|---|
| 15 | [MeN-imidazolium] | CF$_3$CO$_2^\ominus$ | 393.3 (M$^+$); EI |
| 16 | H$_3$N⊕− | CF$_3$CO$_2^\ominus$ | 328.1 (M$^+$); EI |
| 17 | Me−N⊕(DABCO)N⊕− | 2 Cl$^\ominus$ | 437.8 (M$^+$); ESI |
| 18 | H$_2$N−C(O)−CH$_2$−N⊕(DABCO)N⊕− | 2 CF$_3$CO$_2^\ominus$ | 480.6 (M$^{+2}$ − H$^+$); ESI |
| 19 | H$_3$N⊕−(CH$_2$)$_3$−N⊕(DABCO)N⊕− | 3 CF$_3$CO$_2^\ominus$ | 480.5 (M$^{+3}$ − 2H$^+$); ESI |
| 20 | H$_3$N⊕−(CH$_2$)$_2$−NH−C(O)−CH$_2$−N⊕(DABCO)N⊕− | 3 CF$_3$CO$_2^\ominus$ | 523.4 (M$^{+3}$ − 2H$^+$); ESI |

TABLE 5

[Structure: Q⊕ — (CH2)3 — C6H4 — CH2 — CH(CO2H) — CH(CO2H) — CH2 — Ph, with Y⊖ counterion]

| Example No. | Q⊕ | Y⊖ | m/z |
|---|---|---|---|
| 21 | N-methylimidazolium | Cl⊖ | 421.5 (M⁺); ESI |
| 22 | H2N-C(=O)-CH2-[DABCO]⊕⊕ | 2 Cl⊖ | 508.6 (M⁺² − H⁺); ESI |
| 23 | H3N⊕-CH2CH2-[DABCO]⊕⊕ | 3 Cl⊖ | 508.3 (M⁺³ − 2H⁺); ESI |
| 24 | H3N⊕-CH2CH2-NH-C(=O)-CH2-[DABCO]⊕⊕ | 3 Cl⊖ | 551.3 (M⁺³ − 2H⁺); ESI |

TABLE 6

[Structure: Q⊕ — (CH2)7 — CH(CO2H) — CH(CO2H) — CH2 — Ph, with Y⊖ counterion]

| Example No. | Q⊕ | Y⊖ | m/z |
|---|---|---|---|
| 25 | N-methylimidazolium | Cl⊖ | 387.5 (M⁺); ESI |
| 26 | H2N-C(=O)-CH2-[DABCO]⊕⊕ | 2 Cl⊖ | 474.7 (M⁺² − H⁺); ESI |
| 27 | H3N⊕-CH2CH2-[DABCO]⊕⊕ | 3 Cl⊖ | 474.4 (M⁺³ − 2H⁺); ESI |

TABLE 6-continued

| Example No. | Q⊕ | Y⊖ | m/z |
|---|---|---|---|
| 28 | H₃N⊕–CH₂CH₂–NH–C(O)–CH₂–N⊕(DABCO)N⊕– | 3 Cl⊖ | 517.4 (M⁺³ − 2H⁺); ESI |

TABLE 7

| Example No. | Q⊕ | Y⊖ | m/z |
|---|---|---|---|

TABLE 7-continued

| 29 | MeN⟨imidazole⟩N⊕– | Cl⊖ | 469.3 (M⁺); ESI |
|---|---|---|---|

EXAMPLES 30–104

Additional compounds of the present invention can be prepared employing the procedures described herein. These are described in Tables 8–18.

TABLE 8

| Example No. | Q⊕ | Y⊖ |
|---|---|---|
| 30 | H₃N⊕–(CH₂)₃–N⊕(DABCO)N⊕– | 3 Cl⊖ |
| 31 | H₃N⊕–(CH₂)₅–N⊕(DABCO)N⊕– | 3 CH₃CO₂⊖ |

TABLE 8-continued
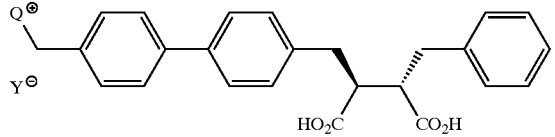
| Example No. | Q⊕ | Y⊖ |
|---|---|---|
| 32 | 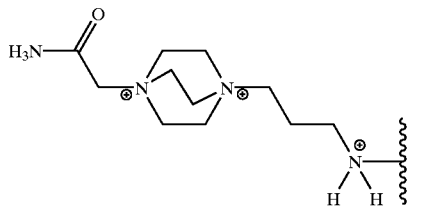 | 3 Cl⊖ |
| 33 | 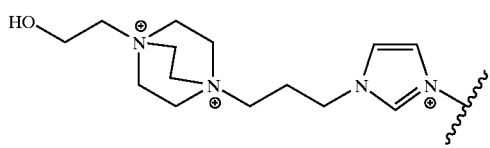 | 3 Cl⊖ |
| 34 | 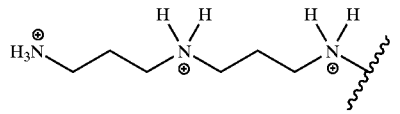 | 3 Cl⊖ |
| 35 | 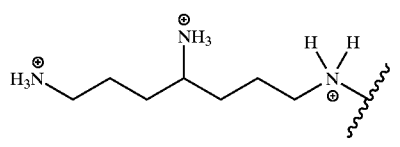 | 3 Cl⊖ |
| 36 | 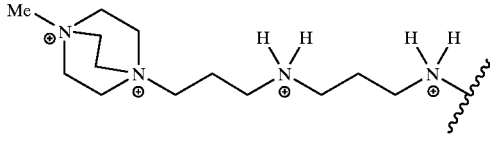 | 4 Cl⊖ |
| 37 | 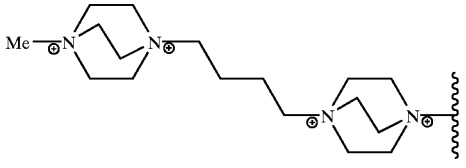 | 4 CH$_3$CO$_2$⊖ |
| 38 | 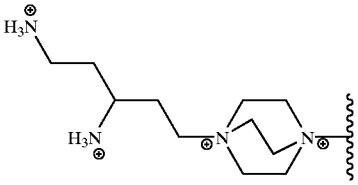 | 4 Cl⊖ |
| 39 | 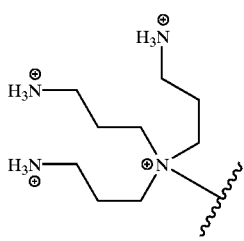 | 4 Cl⊖ |

TABLE 8-continued

| Example No. | Q⊕ | Y⊖ |
|---|---|---|
| 40 | (tetraamine chain structure) | 4 Cl⊖ |
| 41 | (bis-DABCO with propyl linker and acetamide) | 4 Cl⊖ |
| 42 | (guanidinium) | Cl⊖ |
| 43 | (N,N-dimethylamidinium) | Cl⊖ |
| 44 | (DABCO with aminoethyl substituent) | 3 Cl⊖ |
| 45 | (guanidine-propyl-DABCO) | 3 Cl⊖ |
| 46 | (tetraamine branched structure) | 4 Cl⊖ |
| 47 | (tris-imidazolium with methyl cap and propyl linkers) | 3 Cl⊖ |

TABLE 9

[Structure: biphenyl compound with Q⁺CH₂- group, Y⁻, and HO₂C/CO₂H benzyl groups]

| Example No. | Q⊕ | Y⊖ |
|---|---|---|
| 48 | N-methylimidazolium | Cl⊖ |
| 49 | H₂N-C(O)-CH₂-(diazabicyclo)⁺⁺ | 2 Cl⊖ |
| 50 | H₃N⁺-(CH₂)₃-(diazabicyclo)⁺⁺ | 3 Cl⊖ |
| 51 | H₃N⁺-CH₂CH₂-NH-C(O)-CH₂-(diazabicyclo)⁺⁺ | 3 Cl⊖ |
| 52 | branched triammonium (H,H-N⁺, Me,Me-N⁺, NH₃⁺) | 3 Cl⊖ |
| 53 | N-methyl-diazabicyclo⁺-propyl-diazabicyclo⁺⁺ | 3 Cl⊖ |

TABLE 10

[Structure: thiophene-phenyl compound with Q⁺CH₂CH₂- group, Y⁻, and HO₂C/CO₂H benzyl groups]

| Example No. | Q⊕ | Y⊖ |
|---|---|---|
| 54 | N-methylimidazolium | Cl⊖ |

TABLE 10-continued

| Example No. | Q⊕ | Y⊖ |
|---|---|---|
| 55 | H₂N-C(O)-CH₂-(diazabicyclo)⁺⁺ | 2 Cl⊖ |
| 56 | H₃N⁺-(CH₂)₃-(diazabicyclo)⁺⁺ | 3 Cl⊖ |
| 57 | H₃N⁺-CH₂CH₂-NH-C(O)-CH₂-(diazabicyclo)⁺⁺ | 3 Cl⊖ |
| 58 | branched triammonium (H,H-N⁺, Me,Me-N⁺, NH₃⁺) | 3 Cl⊖ |
| 59 | N-methyl-diazabicyclo⁺-propyl-diazabicyclo⁺⁺ | 4 Cl⊖ |

TABLE 11

[Structure: dibenzofuran compound with Q⁺CH₂- group, Y⁻, and HO₂C/CO₂H benzyl groups]

| Example No. | Q⊕ | Y⊖ |
|---|---|---|
| 60 | N-methylimidazolium | Cl⊖ |
| 61 | H₂N-C(O)-CH₂-(diazabicyclo)⁺⁺ | 2 Cl⊖ |

TABLE 11-continued
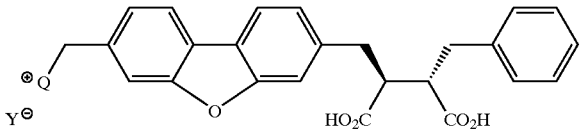
| Example No. | Q⊕ | Y⊖ |
|---|---|---|
| 62 | 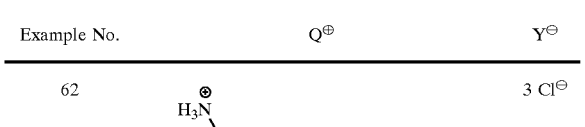 | 3 Cl⊖ |
| 63 | 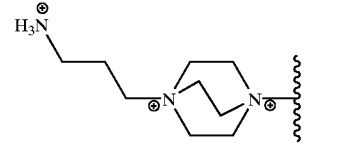 | 3 Cl⊖ |
| 64 | 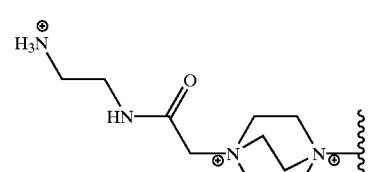 | 3 Cl⊖ |
| 65 | 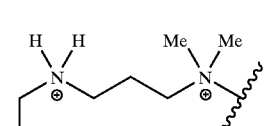 | 4 Cl⊖ |
TABLE 12
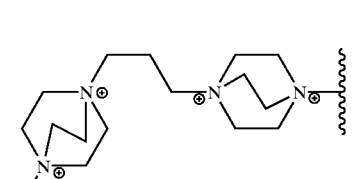
| Example No. | Q⊕ | Y⊖ |
|---|---|---|
| 66 | 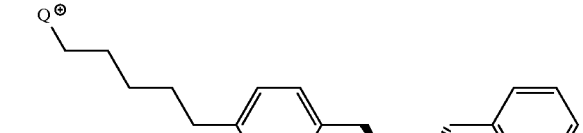 | Cl⊖ |
| 67 | 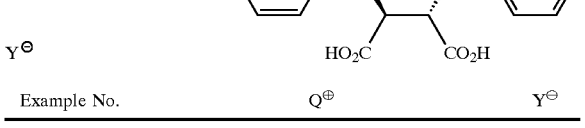 | 2 Cl⊖ |
TABLE 12-continued
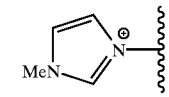
| Example No. | Q⊕ | Y⊖ |
|---|---|---|
| 68 | 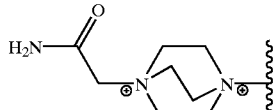 | 3 Cl⊖ |
| 69 | 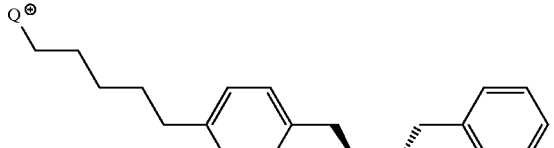 | 3 Cl⊖ |
| 70 | 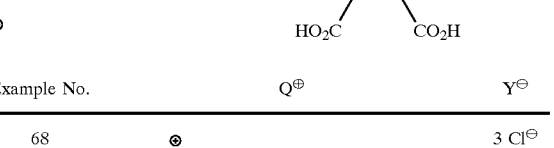 | 3 Cl⊖ |
| 71 | 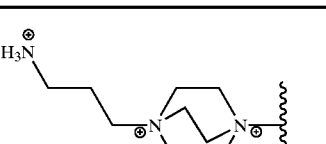 | 4 Cl⊖ |
TABLE 13
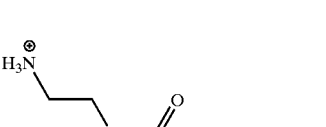
| Example No. | Q⊕ | Y⊖ |
|---|---|---|
| 72 | 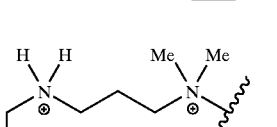 | Cl⊖ |
| 73 | 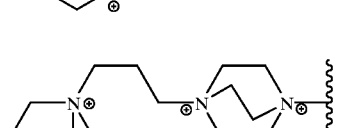 | 2 Cl⊖ |

TABLE 13-continued

Structure: Q⊕–(CH2)n–CH(CO2H)–CH(CH2Ph)–CO2H with Y⊖ counterion

| Example No. | Q⊕ | Y⊖ |
|---|---|---|
| 74 | H3N⊕–CH2CH2CH2–[DABCO]⊕⊕– | 3 Cl⊖ |
| 75 | H3N⊕–CH2CH2–NH–C(O)–CH2–[DABCO]⊕⊕– | 3 Cl⊖ |
| 76 | H2N⊕(H)–CH2CH2CH2–N⊕(Me)2– with pendant –CH2CH2CH2–NH3⊕ | 3 Cl⊖ |
| 77 | N-methyl-DABCO⊕–CH2CH2CH2–[DABCO]⊕⊕– | 4 Cl⊖ |

TABLE 14

Structure: Q⊕–CH2–(4,4′-biphenyl)–CH2–CH(CO2H)–CH(CH2-cyclohexyl)–CO2H with Y⊖ counterion

| Example No. | Q⊕ | Y⊖ |
|---|---|---|
| 78 | N-methylimidazolium– | Cl⊖ |
| 79 | H2N–C(O)–CH2–[DABCO]⊕⊕– | 2 Cl⊖ |
| 80 | H3N⊕–CH2CH2CH2–[DABCO]⊕⊕– | 3 Cl⊖ |

TABLE 14-continued

| Example No. | Q⊕ | Y⊖ |
|---|---|---|
| 81 | H3N⊕–CH2CH2–NH–C(O)–CH2–[DABCO]⊕⊕– | 3 Cl⊖ |
| 82 | H2N⊕(H)–CH2CH2CH2–N⊕(Me)2– with pendant –CH2CH2CH2–NH3⊕ | 3 Cl⊖ |
| 83 | N-methyl-DABCO⊕–CH2CH2CH2–[DABCO]⊕⊕– | 4 Cl⊖ |

TABLE 15

Structure: Q⊕–CH2CH2CH2–O–(4-phenylene)–CH2–CH(CO2H)–CH(CH2Ph)–CO2H with Y⊖ counterion

| Example No. | Q⊕ | Y⊖ |
|---|---|---|
| 84 | N-methylimidazolium– | Cl⊖ |
| 85 | H2N–C(O)–CH2–[DABCO]⊕⊕– | 2 Cl⊖ |
| 86 | H3N⊕–CH2CH2CH2–[DABCO]⊕⊕– | 3 Cl⊖ |

TABLE 15-continued

Structure: Q⊕–O–(CH2)3–C6H4(para)–CH2–CH(CO2H)–CH(CO2H)–CH2–C6H5 ; Y⊖

| Example No. | Q⊕ | Y⊖ |
|---|---|---|
| 87 | H3N⊕–CH2CH2–NH–C(=O)–CH2–N⊕(DABCO)N⊕–~ | 3 Cl⊖ |
| 88 | H2N⊕(CH2)3–N⊕H(CH2)3–N⊕Me2–~ with pendant –(CH2)3NH3⊕ | 3 Cl⊖ |
| 89 | Me–N⊕(DABCO)N⊕–(CH2)3–N⊕(DABCO)N⊕–~ | 4 Cl⊖ |

TABLE 16

Structure: Q⊕–O–(CH2)3–(naphthalene-2,6-diyl)–CH2–CH(CO2H)–CH(CO2H)–CH2–C6H5 ; Y⊖

| Example No. | Q⊕ | Y⊖ |
|---|---|---|
| 90 | MeN(imidazolium)–~ | Cl⊖ |
| 91 | H2N–C(=O)–CH2–N⊕(DABCO)N⊕–~ | 2 Cl⊖ |
| 92 | H3N⊕–(CH2)3–N⊕(DABCO)N⊕–~ | 3 Cl⊖ |

TABLE 16-continued

| Example No. | Q⊕ | Y⊖ |
|---|---|---|
| 93 | H3N⊕–CH2CH2–NH–C(=O)–CH2–N⊕(DABCO)N⊕–~ | 3 Cl⊖ |
| 94 | H2N⊕(CH2)3–N⊕H(CH2)3–N⊕Me2–~ with pendant –(CH2)3NH3⊕ | 3 Cl⊖ |
| 95 | Me–N⊕(DABCO)N⊕–(CH2)3–N⊕(DABCO)N⊕–~ | 4 Cl⊖ |

TABLE 17

Structure: Q⊕–O–(CH2)3–NH–C(=O)–C6H4(para)–CH2–CH(CO2H)–CH(CO2H)–CH2–C6H5 ; Y⊖

| Example No. | Q⊕ | Y⊖ |
|---|---|---|
| 96 | MeN(imidazolium)–~ | Cl⊖ |
| 97 | H2N–C(=O)–CH2–N⊕(DABCO)N⊕–~ | 2 Cl⊖ |

TABLE 17-continued
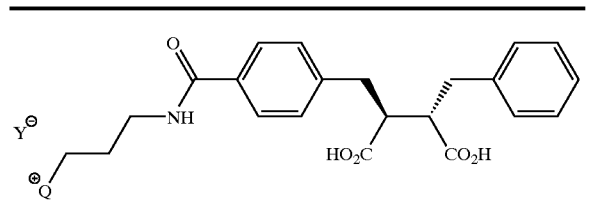
| Example No. | Q⊕ | Y⊖ |
|---|---|---|
| 98 | 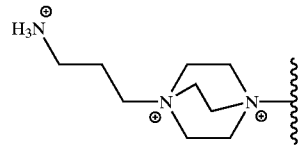 | 3 Cl⊖ |
| 99 | 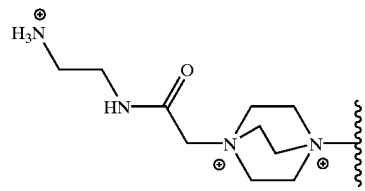 | 3 Cl⊖ |
TABLE 17-continued
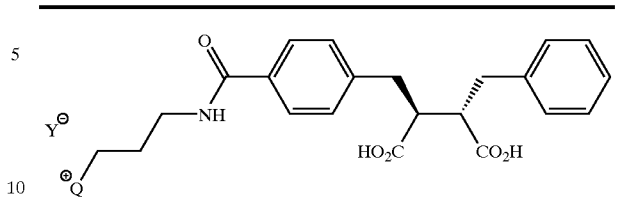
| Example No. | Q⊕ | Y⊖ |
|---|---|---|
| 100 | 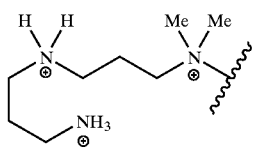 | 3 Cl⊖ |
| 101 | 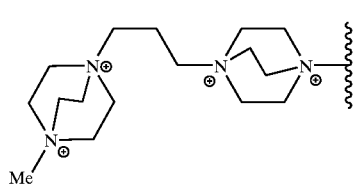 | 4 Cl⊖ |
TABLE 18
| Example No. |
|---|
| 102 |
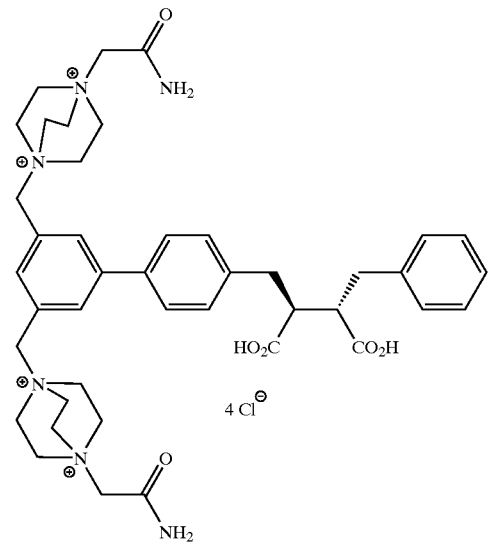

TABLE 18-continued

Example No.

103

104

BIOLOGICAL ACTIVITY

IMP-1 metallo-β-lactamase lacking the N-terminal 18 hydrophobic amino acids which encode the putative periplasmic signal sequence (EMBL access code PACATAAC6) was PCR amplified from plasmid DNA prepared from a carbapenem-resistant strain of Pseudomonas aeruginosa (CL5673). The PCR product was cloned into pET30a+ (Novegen) and expressed in E. coli BL21(DE3) after induction with 0.5 mM IPTG for 20 hours at room temperature in minimal media supplemented with casamino acids and 348 μM $ZnSO_4$. Soluble IMP-1 was purified from cell extracts by SP-Sepharose (Pharmacia) ion exchange and Superdex 75 (Pharmacia) size-exclusion chromatography. Soluble CcrA metallo-β-lactamase was cloned from an imipenem resistant clinical isolate of Bacteroides fragilis and was expressed and purified as described by Toney et al. [Protein Expr. Purif. 9 355 (1997)].

The $IC_{50}$ of succinate derivatives was determined following a 15 minute incubation at 37° C. with IMP-1 (0.75 nM in 50mM MOPS, pH 7) or CcrA (4 nM in 50 mM Mops pH 7). Using initial velocity as a measure of activity, inhibition was monitored spectrophotometrically at 490 nm in a Molecular Devices SPECTRAmax™ 250 96-well plate reader employing nitrocefin as the reporter substrate at approximately $K_m$ concentration (60 μM).

A laboratory strain of E.coli engineered to express IMP-1 was used to evaluate the ability of succinate derivatives to reverse metallo-β-lactamase-mediated carbapenem resistance in bacteria. Native IMP-1, which included the N-terminal periplasmic signal sequence, was PCR amplified from CNA isolated from a carbapenem resistant P. aeruginosa clinical isolate, CL56673, and cloned into the pET30a vector. The basal (uninduced) level of IMP-1 expressed when pET30a-IMP-1 was introduced into E. coli BL21 (DE3) resulted in 4-, 64- or 500-fold reduced sensitivity to impenem, meropenem or (1S,5R,6S)-1-methyl-2-{7-[4-(aminocarbonylmethyl)-1,4-diazoniabicyclo(2.2.2)octan-1-yl]methyl-fluoren-9-on-3-yl}-6-(1R-hydroxyethyl)-carbapen-2-em-3-carboxylate chloride (a carbapenem synthesized at Merck Research Laboratories) respectively. For example, the minimum inhibitory concentration (MIC) of (1S,5R,6S)-1-methyl-2-{7-[4-(aminocarbonylmethyl)-1,4-diazoniabicyclo(2.2.2)octan-1-yl]methyl-fluoren-9-on-3-yl}-6-(1R-hydroxyethyl)-carbapen-2-em-3-carboxylate chloride, was typically increased from 0.06–0.12 μg/ml to 16–32 μg/ml by the expression of IMP-1. To evaluate IMP-1 inhibitors, an overnight culture of E. coli BL2(DE3)/pET30a-IMP-1, grown 35° C. in LB broth (Difco) or Mueller Hinton broth (BBL) supplemented with kanamycin (50 μM/ml), was diluted to a final concentration of ~$10^5$ cells/ml in Mueller Hinton broth (BBL) containing a subinhibitory concentration (0.25×MIC) of the carbapenem, (1S,5R,6S)-1-methyl-2-{7-[4-(aminocarbonylmethyl)-1,4-diazoniabicyclo(2.2.2)octan-1-yl]methyl-fluoren-9-on-3-yl}-6-(1R-hydroxyethyl)carbapen-2-em-3-carboxylate chloride. Various concentrations of IMP-1 inhibitor were added to the bacterial growth medium and their capacity to effect a four-fold or greater increase in sensitivity to the carbapenem was monitored. The readout for antibacterial activity showed no visible growth after 20 hours incubation at 35° C.

Representative compounds of Formula I were tested as inhibitors against purified IMP-1 metallo-β-lactamase and found to be active in an $IC_{50}$ range of from about 0.1 nM to about 1000 nM. The ability of representative compounds of Formula I to potentiate the activity of the carbapenem antibiotic (1S,5R,6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)- carbapen-2-em-3-carboxylate chloride against an IMP-1 producing laboratory strain *E. coli* BL21(DE3)/pET30a-IMP-1 was tested. Compounds of Formula I in the concentration range of from about 0.003 μM to about 12.5 μM. were found to produce 4-fold increase in sensitivity to the carbapenem antibiotic (1S,5R,6S)-1-methyl-2-{7-[4-(aminocarbonylmethyl)-1,4-diazoniabicyclo(2.2.2)octan-1-yl]-methyl-fluoren-9-on-3-yl}-6-(1R-hydroxyethyl) carbapen-2-em-3-carboxylate chloride in an IMP-1 producing laboratory strain *E. coli* BL21(DE3)/pET30a-IMP-1.

What is claimed is:

1. A compound represented by formula I:

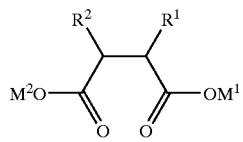

pharmaceutically acceptable salt, or solvate thereof, wherein:

$M^1$ and $M^2$ are independently selected from:
(a) hydrogen,
(b) pharmaceutically acceptable cation,
(c) pharmaceutically acceptable esterifying group; and
(d) a negative charge;

$R^1$ is (c)
(c) a group of the formula:

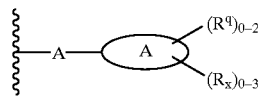

wherein
—A— represents a single bond, $C_1$ to $C_8$ straight, branched or unsaturated alkyl group optionally substituted with 1 to 2 $R_x$ groups and optionally interrupted by one of the following O, S, $SO_2$, —C(O)—, —C(O)—$NR^a$— and —$CO_2$—;

represents:
(1) a $C_6$ to $C_{14}$ aryl group;
(2) a $C_3$ to $C_{10}$ alicyclic group;
(3) a $C_3$ to $C_{14}$ heteroaryl group with 1 to 3 heteroatoms, 0 to 3 of which heteroatoms are nitrogen and 0 to 1 of which are oxygen or sulfur;
(4) a $C_3$ to $C_{10}$ heterocyclic group with 1 to 2 heteroatoms, 0 to 1 of which heteroatoms are nitrogen, and 0 to 2 of which are oxygen or sulfur;

$R^2$ is (d):
(d) a group of the formula:

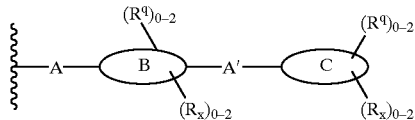

wherein:
—A— is as defined above;
A' is a single bond, O, S, or a $C_1$ to $C_6$ straight, branched saturated or unsaturated alkyl group optionally substituted with 1–2 $R_x$ groups and optionally interrupted by one of the following; groups O, S, $SO_2$, —C(O)—, —C(O)—$NR^a$— and —$CO_2$—;

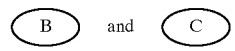 and 

are independently selected from:
(1) a $C_6$ to $C_{10}$ aryl group;
(2) a $C_3$ to $C_8$ alicyclic group;
(3) a $C_2$ to $C_9$ heteroaryl group with 1 to 3 heteroatoms, 0 to 3 of which heteroatoms are nitrogen and 0 to 1 of which are oxygen or sulfur; and
(4) a $C_3$ to $C_8$ heterocyclic group with 1 to 2 heteroatoms, 0 to 1 of which heteroatoms are nitrogen, and 0 to 2 of which are oxygen or sulfur;

provided that at least one $R^q$ group is present in $R^1$ or $R^2$, and that when more than one $R^q$ is present the total number of cationic nitrogen atoms does not exceed 8; the total number of cationic nitrogen atoms can be charged balanced by $M^1$ and $M^2$ or by $M^1$ and $M^2$ in combination with an appropriate number of $Y^-$; wherein:

each $R^q$ is —E—$Q^+Y^-$;
$Y^-$ is a pharmaceutically acceptable anionic group;
E is —$(CH_2)_m$—X—$(CH_2)_n$—;
m is 0 to 6;
n is 0 to 6 (but when E is attached to an aromatic ring n is 1–6);
X is a bond, O, S, $SO_2$, —C(O)—, —C(O)—N($R^a$)—, —C(O)O—, —CH=CH— or —C≡C—, provided that when X is O, S, —C(O)—N($R^a$)— or —C(O)O—, then n is 2 to 6
and $Q^+$, attached to the $(CH_2)_n$ terminus of E is:
(1) a cationic group selected from the following:

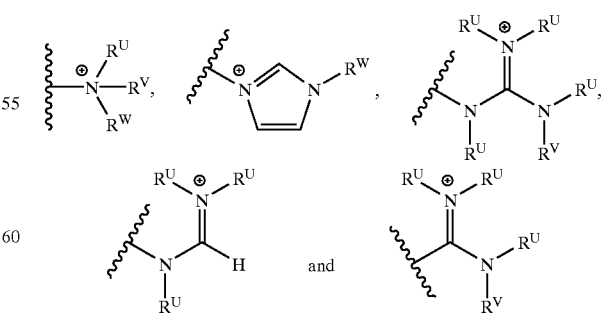

wherein:
$R^u$ and $R^v$ are independently hydrogen or $C_{1-6}$ alkyl optionally substituted with 1 to 2 $R^y$;

$R^w$ is hydrogen or $C_{1-6}$ alkyl optionally substituted with 1 to 2 $R_x$;

$R^u$ and $R^v$ when bonded to the same nitrogen atom may together be a $C_{3-6}$ alkyl radical, which when taken together with the intervening atoms form a ring;

two $R^u$ groups on separate nitrogen atoms may together comprise a $C_{2-5}$ alkyl radical, which when taken together with the intervening atoms form a ring;

$R^u$, $R^v$ and $R^w$ when bonded to the same nitrogen atom may together form a $C_{6-10}$ tertiary alkyl radical, which with $N^+$ forms a bicyclic ring;

(2) a dicationic group:

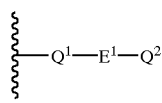

wherein:
$E^1$ is —$(CH_2)_p$—Z—$(CH_2)_r$—;
p and r are independently 1 to 4;
Z is a bond, O, S, SO$_2$, —C(O)—, —C(O)O—**, —CH=CH—, —C≡C— or

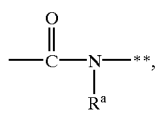

provided that when Z is O or S, p is 2 to 4 and r is 2 to 4 and when Z is

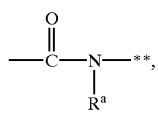

or —C(O)O—**, r is 2 to 4;
wherein ** denotes the atom which is bonded to the —$(CH_2)_r$— moiety of $E^1$ above;
$Q^1$ is selected from the following:

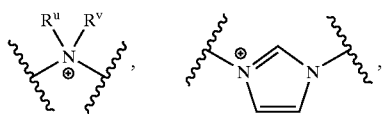

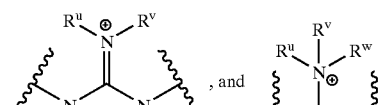

$Q^2$ is selected from the following:

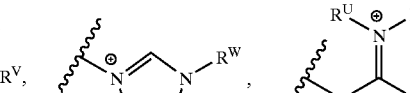

-continued

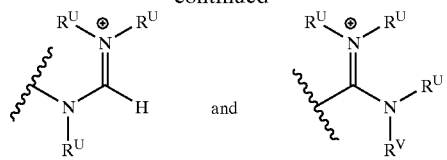

$R^u$, $R^v$ and $R^w$ are independently selected and defined as above,
and in addition, in the case where two $R^u$ groups on separate nitrogen atoms are joined to form a ring as defined above, two $R^v$ groups on the same two separate nitrogen atoms may also comprise a $C_{1-5}$ alkyl radical to form together with the intervening atoms a bicyclic ring; an example of such is:

(3) a tricationic group selected from the following:

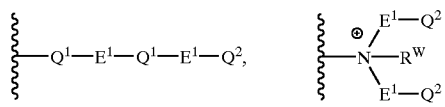

wherein:
each $E^1$ is as defined above, but selected independently;
each $Q^1$ is as defined above, but selected independently;
each $Q^2$ is as defined above, but selected independently;
$R^u$, $R^v$ and $R^w$ are defined as in the definition of $Q^+$ item (2) above and selected independently; or (4) a etracationic group selected from the following:

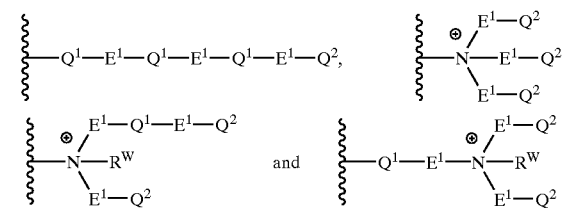

wherein:
each $E^1$ is as defined above, but selected independently;
each $Q^1$ is as defined above, but selected independently;
each $Q^2$ is as defined above, but selected independently;
$R^u$, $R^v$ and $R^w$ are defined as in the definition of $Q^+$ item (2) above and selected independently;
where each $R_x$ is independently selected from the group consisting of:
(a) F, Cl, Br, I,
(b) $CF_3$,
(c) $OR^b$,
(d) CN, (e) —C(O)—R$^c$,
(f) —S(O$_2$)—R$^f$,
(g) —C(O)—OR$^a$
(h) —O—C(O)—R$^c$,
(i) —S—R$^b$,
(j) —N(R$^a$)—C(O)—R$^c$, (k) 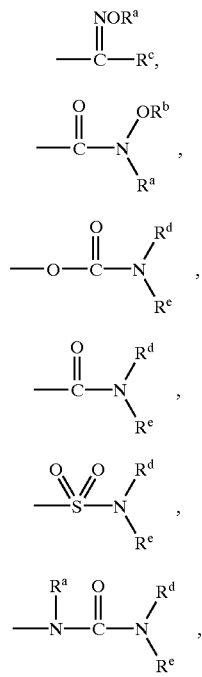

(l)

(m)

(n)

(o)

(p)

(q) —N(R$^a$)—C(O)—OR$^f$,
(r) —S(O)—R$^f$,
(s) —N(R$^a$)—S(O$_2$)—R$^f$,
(t) NO$_2$,
(u) C$_1$ to C$_8$ straight, branched or unsaturated alkyl optionally substituted with one of the substituents (a) through (t) above; and
(v) —CH$_2$-aryl wherein the aryl is optionally substituted with one of the substituents (a) through (t) above;
or two adjacent R$_x$ groups on an aromatic ring may consist of the following divalent moiety, —O—CH$_2$—;
wherein:
R$^a$ is H, C$_1$ to C$_6$ alkyl optionally substituted with R$^y$;
R$^b$ is H, C$_1$ to C$_6$ alkyl optionally substituted with R$^y$, CH$_2$-aryl, or aryl, said aryls optionally substituted with 1–2 R$^y$ groups;
R$^c$ is H, C$_1$ to C$_6$ alkyl optionally substituted with R$^y$, CF$_3$, or aryl, said aryl optionally substituted with 1–2 R$^y$ groups;
R$^d$ and R$^e$ are independently hydrogen, C$_1$ to C$_4$ alkyl optionally substituted with R$^y$, or R$^d$ and R$^e$ taken together may represent a 3 to 5-membered alkyl radical to form a ring, or R$^d$ and R$^e$ taken together may represent a 2 to 4-membered alkyl radical interrupted by O, S, SO or SO$_2$ to form a ring;
R$^f$ is C$_1$ to C$_6$ alkyl optionally substituted with R$^y$, or aryl, said aryl optionally substituted with 1–2 R$^y$ groups; and
R$^y$ is —OH, —OCH$_3$, OCONH$_2$, OCOCH$_3$, CHO, COCH$_3$, CO$_2$CH$_3$, CONH$_2$, CN, SOCH$_3$, SO$_2$CH$_3$, SO$_2$NH$_2$, F, Cl, Br, I or CF$_3$.

2. A compound in accordance with claim 1 wherein M$^1$ and M$^2$ are independently hydrogen or a negative charge and all other variables are as defined in claim 1.

3. A compound in accordance to claim 1 where R$^1$ represents (c) 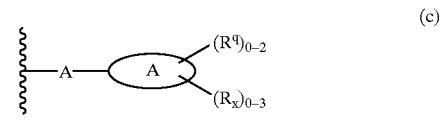

wherein at least one R$^q$ group is present and all other variables are defined in claim 1.

4. A compound in accordance to claim 1 where R$^2$ represents (d)

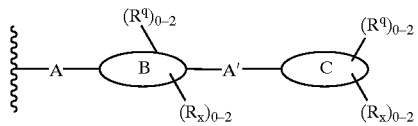

wherein at least one R$^q$ group is present and all other variables are defined in claim 1.

5. A compound in accordance with claim 1 wherein the relative and absolute stereochemistry is:

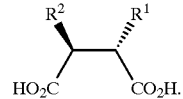

6. A compound in accordance with claim 5 wherein R$^1$ represents a group of the formula:

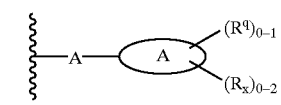

wherein A is (CH$_2$)$_{1-5}$ and

is phenyl, naphthyl, cyclohexyl or dibenzofuranyl, and all other variables are as defined in claim 1.

7. A compound in accordance with claim 5 wherein where R$^2$ represents a group of the formula:

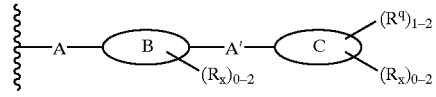

wherein
A is (CH$_2$)$_{1-3}$, A' is a single bond, —O— or (CH$_2$)$_{1-2}$ and

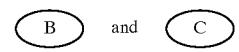

independently represent phenyl, thienyl, pyridyl, furanyl or cyclohexyl.

8. A compound in accordance with claim 5 where R$^1$ is a group of the formula:

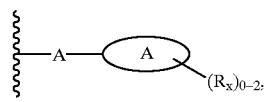

where A is $(CH_2)_{1-2}$ and

is phenyl, cyclopentyl or cyclohexyl and $R^2$ is a group of the formula:

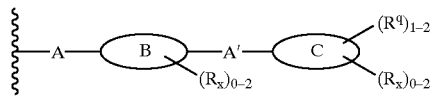

where A is $(CH_2)_{1-2}$, A' is a single bond,

is phenyl, thienyl or cyclohexyl and

is phenyl, thienyl or pyridyl, and all other variables are as defined in claim 1.

9. A compound according to claim 5 wherein $R^1$ is

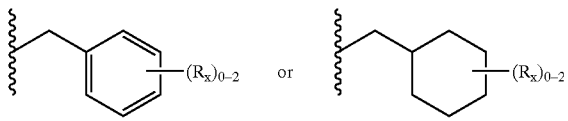

$R^2$ is

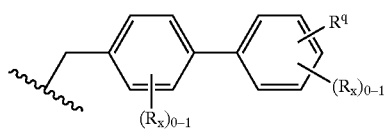

and all other variables are as defined in claim 1.

10. A compound according to claim 9 wherein $R^1$ is:

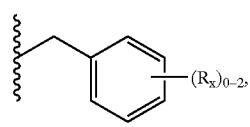

$R^2$ is:

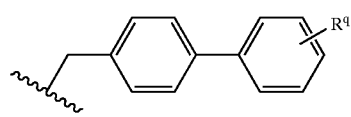

and all other variables are as defined in claim 1.

11. A compound according to claim 1 wherein 1 or 2 $R^q$ groups are present containing a total number of 2 to 6 cationic nitrogen atoms.

12. A compound according to claim 1 wherein a single Rq substituent is present containing a tricationic or tetracationic $Q^+$ group.

13. A compound according to claim 12 wherein $R^q$ is —E—$Q^+Y^-$ wherein E is $(CH_2)_{0-6}$ or —C(O)—N($R^a$)—$(CH_2)_{2-4}$— and $Q^+$ is a tricationic or tetracationic group and $Y^-$ and $R^a$ are as defined in claim 1.

14. A compound according to claim 12 wherein the tricationic Q+ group is selected from the group consisting of:

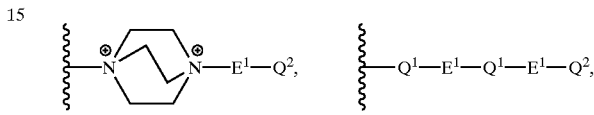

wherein $E^1$ is $(CH_2)_{2-4}$ or —$(CH_2)$—C(O)—N($R^a$)—$(CH_2)_{2-4}$— and $R^a$, $Q^1$ and $Q^2$ are as defined in claim 1.

15. A compound according to claim 14 wherein the tricationic $Q^+$ group is selected from:

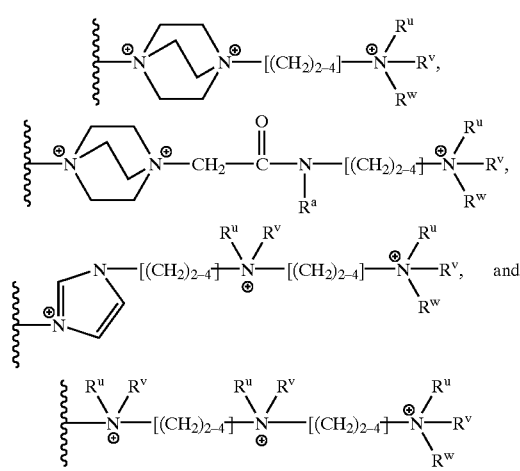

wherein $R^u$, $R^v$, and $R^w$ are defined in claim 1.

16. A compound according to claim 12 wherein the tetracationic $Q^+$ group is selected from the group consisting of:

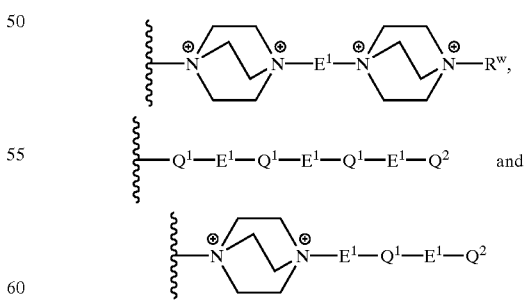

wherein $E^1$ is $(CH_2)_{2-4}$ or —$(CH_2)$—C(O)—N($R^a$)—$(CH_2)_{2-4}$— and $R^a$, $Q^1$, $Q^2$, and $R^w$ are as defined in claim 1.

17. A compound according to claim 16 wherein the tetracationic $Q^+$ group is selected from:

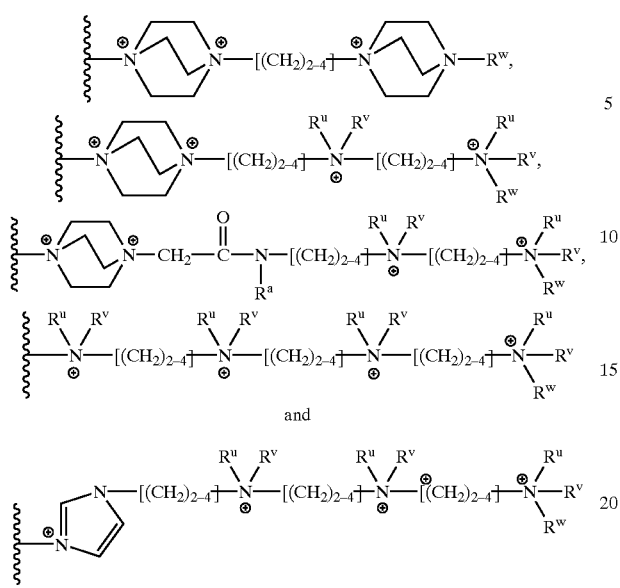
wherein $R^a$, $R^u$, $R^v$, and $R^w$ are described in claim 1.
18. A compound of the structural formula:
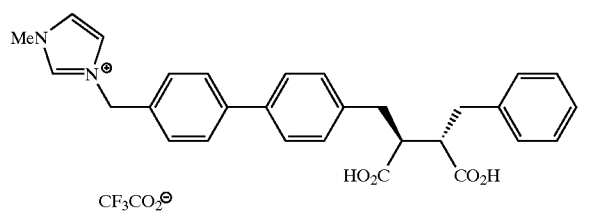
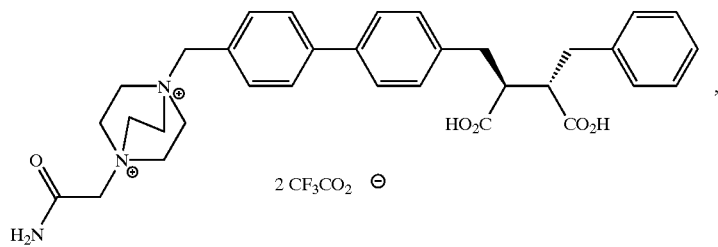
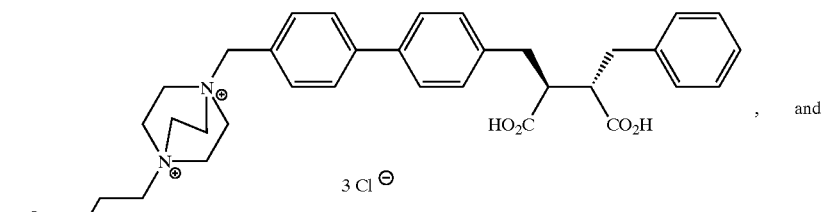
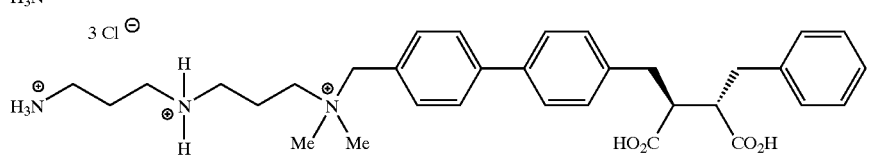
19. A compound represented by Tables 3 and 7:
TABLE 3
| Example No. | $Q^{\oplus}$ | $Y^{\ominus}$ |
|---|---|---|
| 5 | | 3 Cl$^{\ominus}$ |
| 6 | | 3 Cl$^{\ominus}$ |

TABLE 3-continued

[Structure: biphenyl with Q⊕/Y⊖ substituent, CH2-CH(CO2H)-CH(CO2H)-CH2-Ph]

| Example No. | Q⊕ | Y⊖ |
|---|---|---|
| 7 | [H3N⊕-CH2CH2CH2 and H3N⊕-CH2CH2CH2 groups on N⊕(Me)] | 3 Cl⊖ |
| 8 | [H2N⊕ with two propyl-NH3⊕ groups attached to DABCO-like bicyclic diammonium] | 4 Cl⊖ |
| 9 | [N-methylated bicyclic triammonium linked via propyl to DABCO diammonium] | 4 Cl⊖ |
| 10 | [3,4-dihydroxyphenyl-C(=O)-CH2- attached to DABCO diammonium] | 3 Cl⊖ |

TABLE 3-continued

[Structure: biphenyl with Q⊕/Y⊖ substituent, CH2-CH(CO2H)-CH(CO2H)-CH2-Ph]

| Example No. | Q⊕ | Y⊖ |
|---|---|---|
| 11 | [Me3N⊕-CH2CH2CH2- linked to DABCO diammonium] | 3 Cl⊖ |
| 12 | [DABCO diammonium-CH2CH2CH2- linked to DABCO diammonium] | 3 Cl⊖ |
| 13 | [H3N⊕-CH2CH2-NH-C(=O)-CH2- linked to DABCO diammonium] | 3 Cl⊖ |
| 14 | [DABCO mono-ammonium-(CH2)4- linked to DABCO diammonium] | 3 Cl⊖ |

TABLE 7

[Structure: biphenyl with Q⊕/Y⊖ substituent, CH2-CH(CO2H)-CH(CO2H)-CH2-phenyl-phenyl]

| Example No. | Q⊕ | Y⊖ | m/z |
|---|---|---|---|
| 29 | [N-methylimidazolium] | Cl⊖ | 469.3 (M⁺); ESI. |

20. A compound represented by Tables 8–10, 14 and 18:

TABLE 8

| Example No. | Q⊕ | Y⊖ |
|---|---|---|
| 30 | H₃N⁺–(CH₂)₃–[N⁺(DABCO)N⁺]–⟍ | 3 Cl⊖ |
| 31 | H₃N⁺–(CH₂)₅–[N⁺(DABCO)N⁺]–⟍ | 3 CH₃CO₂⊖ |
| 32 | H₃N–C(=O)–CH₂–[N⁺(DABCO)N⁺]–(CH₂)₃–N⁺H₂–⟍ | 3 Cl⊖ |
| 33 | HO–CH₂CH₂–[N⁺(DABCO)N⁺]–(CH₂)₃–(imidazolium)–⟍ | 3 Cl⊖ |
| 34 | H₃N⁺–(CH₂)₃–N⁺H₂–(CH₂)₃–N⁺H₂–⟍ | 3 Cl⊖ |
| 35 | H₃N⁺–(CH₂)₃–CH(N⁺H₃)–(CH₂)₃–N⁺H₂–⟍ | 3 Cl⊖ |
| 36 | Me–[N⁺(DABCO)N⁺]–(CH₂)₃–N⁺H₂–(CH₂)₃–N⁺H₂–⟍ | 4 Cl⊖ |
| 37 | Me–[N⁺(DABCO)N⁺]–(CH₂)₄–[N⁺(DABCO)N⁺]–⟍ | 4 CH₃CO₂⊖ |

TABLE 8-continued
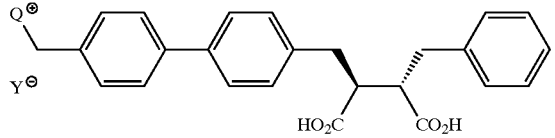
| Example No. | Q⊕ | Y⊖ |
|---|---|---|
| 38 | 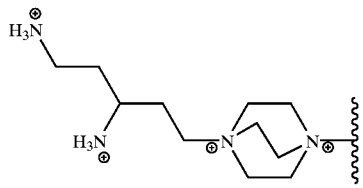 | 4 Cl⊖ |
| 39 | 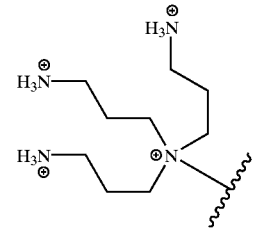 | 4 Cl⊖ |
| 40 | 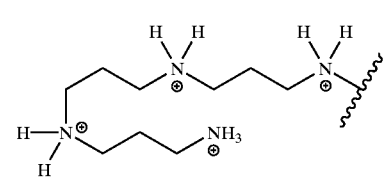 | 4 Cl⊖ |
| 41 | 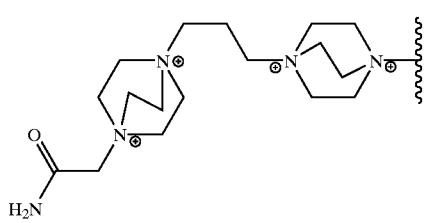 | 4 Cl⊖ |
| 42 | 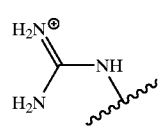 | Cl⊖ |
| 43 | 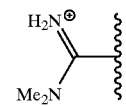 | Cl⊖ |
| 44 | 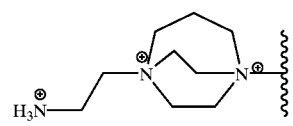 | 3 Cl⊖ |
| 45 | 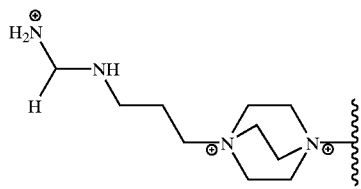 | 3 Cl⊖ |

TABLE 8-continued

| Example No. | Q⊕ | Y⊖ |
|---|---|---|
| 46 | (triamine structure with 3 ⊕NH₃ groups and one ⊕NH) | 4 Cl⊖ |
| 47 | (tris-imidazolium structure with Me-imidazolium linked by propyl chains) | 3 Cl⊖ |

TABLE 9

| Example No. | Q⊕ | Y⊖ |
|---|---|---|
| 48 | N-methylimidazolium | Cl⊖ |
| 49 | H₂N-C(=O)-CH₂-(DABCO⊕⊕) | 2 Cl⊖ |
| 50 | H₃N⊕-propyl-(DABCO⊕⊕) | 3 Cl⊖ |
| 51 | H₃N⊕-ethyl-NH-C(=O)-CH₂-(DABCO⊕⊕) | 3 Cl⊖ |
| 52 | (H₂N⊕)-propyl-N⊕(propyl-NH₃⊕)-propyl-NMe₂⊕ | 3 Cl⊖ |
| 53 | Me-(DABCO⊕⊕)-propyl-(DABCO⊕⊕) | 3 Cl⊖ |

TABLE 10

| Example No. | Q⊕ | Y⊖ |
|---|---|---|
| 54 | N-methylimidazolium | Cl⊖ |

TABLE 10-continued
(structural diagram at top)
| Example No. | $Q^{\oplus}$ | $Y^{\ominus}$ |
|---|---|---|
| 55 | 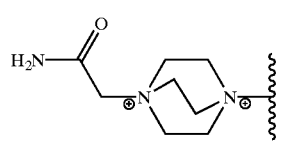 | 2 Cl$^{\ominus}$ |
| 56 | 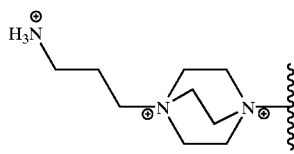 | 3 Cl$^{\ominus}$ |
| 57 | 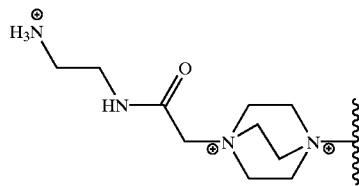 | 3 Cl$^{\ominus}$ |
| 58 | 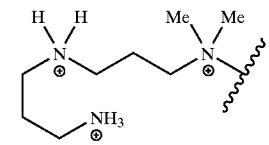 | 3 Cl$^{\ominus}$ |
| 59 | 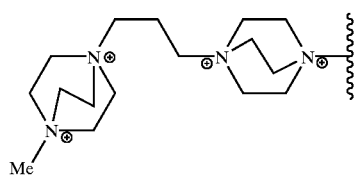 | 4 Cl$^{\ominus}$ |
TABLE 14
(structural diagram at top)
| Example No. | $Q^{\oplus}$ | $Y^{\ominus}$ |
|---|---|---|
| 78 | 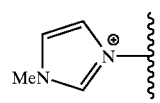 | Cl$^{\ominus}$ |
| 79 | 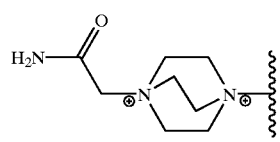 | 2 Cl$^{\ominus}$ |
| 80 | 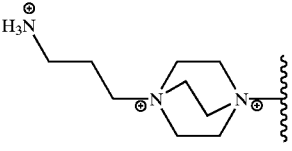 | 3 Cl$^{\ominus}$ |
| 81 | 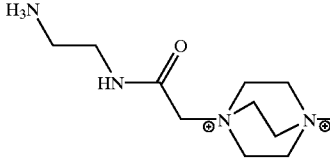 | 3 Cl$^{\ominus}$ |
| 82 | 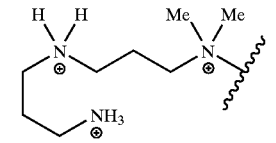 | 3 Cl$^{\ominus}$ |
| 83 | 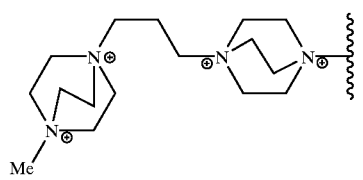 | 4 Cl$^{\ominus}$ |

TABLE 18

Example No.

102

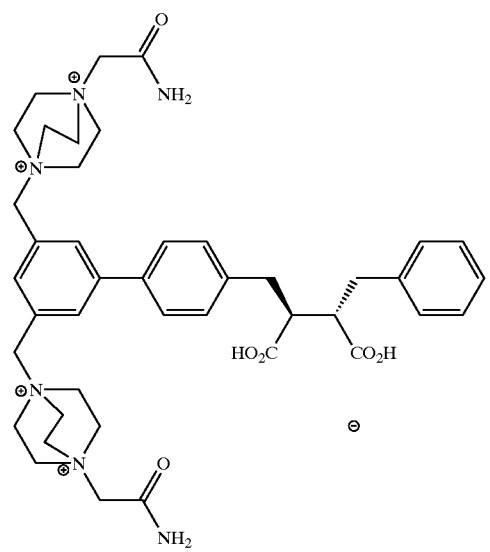

103

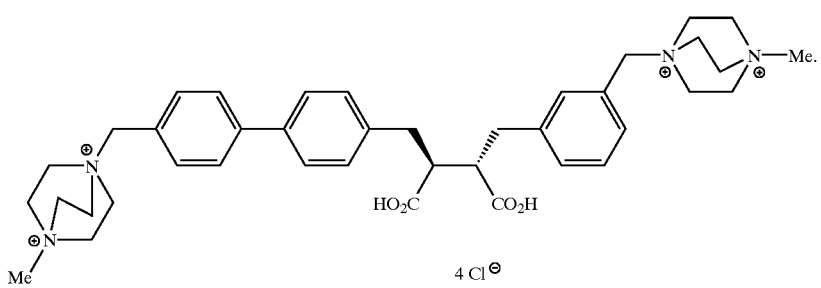

21. A pharmaceutical composition comprised of a compound in accordance with claim 1 in combination with a pharmaceutically acceptable carrier.

22. A pharmaceutical composition in accordance with claim 21 used in the manufacture of a medicament for the treatment of bacterial infections.

23. A pharmaceutical composition in accordance with claim 21 further comprising a β-lactam antibiotic.

24. A pharmaceutical composition in accordance with claim 23 wherein the β-lactam is a carbapenem antibiotic.

25. A composition according to claim 23 which further contains a serine β-lactamase inhibitor.

26. A composition according to claim 24 which further contains a DHP inhibitor.

27. A method of treating a bacterial infection comprising administering to a mammalian patient in need of such treatment a metallo-β-lactamase inhibitor compound as defined in claim 1 in combination with a pharmaceutically acceptable β-lactam antibiotic in an amount which is effective for treating a bacterial infection.

28. A method according to claim 27 wherein the β-lactam is a carbapenem antibiotic.

29. A method according to claim 28, which further contains a DHP inhibitor.

30. A method according to claim 29 wherein the DHP inhibitor is cilastatin.

31. A method according to claim 27 which further contains a serine β-lactamase inhibitor.

* * * * *

UNITED STATES PATENT AND TRADEMARK OFFICE
CERTIFICATE OF CORRECTION

PATENT NO.    : 6,630,510 B1                                     Page 1 of 1
DATED         : October 7, 2003
INVENTOR(S)   : James M. Balkovec et al.

It is certified that error appears in the above-identified patent and that said Letters Patent is hereby corrected as shown below:

<u>Column 94,</u>
Table 7, delete

" 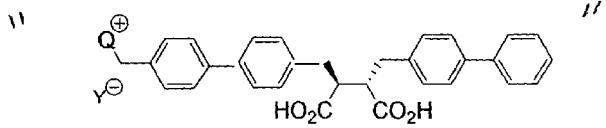 "

and insert in its place:

-- 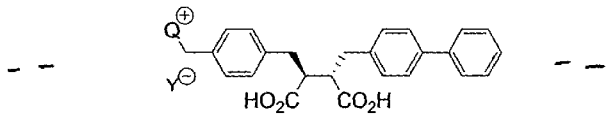 --

Signed and Sealed this

Third Day of February, 2004

JON W. DUDAS
*Acting Director of the United States Patent and Trademark Office*